US012626784B2

(12) United States Patent
Morris et al.

(10) Patent No.: US 12,626,784 B2
(45) Date of Patent: May 12, 2026

(54) COLORECTAL CANCER CONSENSUS MOLECULAR SUBTYPE CLASSIFIER CODESETS AND METHODS OF USE THEREOF

(71) Applicant: Board of Regents, The University of Texas System, Austin, TX (US)

(72) Inventors: Jeffrey Morris, Houston, TX (US); Scott Kopetz, Houston, TX (US); Dipen Maru, Houston, TX (US); David G. Menter, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 1129 days.

(21) Appl. No.: 17/600,598

(22) PCT Filed: Apr. 2, 2020

(86) PCT No.: PCT/US2020/026409
§ 371 (c)(1),
(2) Date: Sep. 30, 2021

(87) PCT Pub. No.: WO2020/206136
PCT Pub. Date: Oct. 8, 2020

(65) Prior Publication Data
US 2022/0180974 A1     Jun. 9, 2022

Related U.S. Application Data

(60) Provisional application No. 62/828,098, filed on Apr. 2, 2019.

(51) Int. Cl.
*G16B 40/20* (2019.01)
*C12Q 1/6886* (2018.01)
*G01N 33/574* (2006.01)
*G16B 25/00* (2019.01)

(52) U.S. Cl.
CPC ........... *G16B 40/20* (2019.02); *C12Q 1/6886* (2013.01); *G16B 25/00* (2019.02); *C12Q 2600/106* (2013.01); *C12Q 2600/112* (2013.01); *C12Q 2600/156* (2013.01); *C12Q 2600/158* (2013.01)

(58) Field of Classification Search
CPC ...... G16B 40/20; G16B 25/00; C12Q 1/6886; C12Q 2600/106; C12Q 2600/112; C12Q 2600/156; C12Q 2600/158; G01N 33/57419; G01N 2800/52
See application file for complete search history.

(56) References Cited

U.S. PATENT DOCUMENTS

2016/0208333 A1     7/2016  Schell et al.

FOREIGN PATENT DOCUMENTS

WO     WO 2013/052480         4/2013
WO     WO-2013052480 A1 *  4/2013    ........... C12Q 1/6886
WO     WO 2017/053192         3/2017
WO     WO 2017/114851         7/2017

OTHER PUBLICATIONS

Allegra, C. J. et al., "Bevacizumab in stage II-III colon cancer: 5-year update of the National Surgical Adjuvant Breast and Bowel Project C-08 trial," *Journal of Clinical Oncology*, 31.3 (2013): 359-364.
Al-Mulla, F, "Microarray-based CGH and copy number analysis of FFPE samples," *Methods Mol. Biol.*, 724 (2011): 131-145.
Barr, S. et al., "Bypassing cellular EGF receptor dependence through epithelial-to-mesenchymal-like transitions," *Clin. Exp. Metastasis*, 25 (2008): 685-693.
Budinska, E. et al., "Gene expression patterns unveil a new level of molecular heterogeneity in colorectal cancer," *Journal of Pathology*, 231 (2013): 63-76.
De Sousa, F. et al., "Poor-prognosis colon cancer is defined by a molecularly distinct subtype and develops from serrated precursor lesions," *Nature Medicine*, 19 (2013): 614-618.
Dienstmann, R. et al., "Consensus molecular subtypes and the evolution of precision medicine in colorectal cancer," *Nat. Rev. Cancer*, 17.2 (2017): 79-92.
Goel, G., "Evolving role of gene expression signatures as biomarkers in early-stage colon cancer," *J. Gastrointest. Cancer*, 45.4 (2014): 399-404.
Guinney, J. et al., "The Consensus Molecular Subtypes of Colorectal Cancer," *Nat Med*, 21.11 (2015): 1-33.
Kelley, R. K., Prognostic and predictive markers in stage II colon cancer: is there a role for gene expression profiling?, *Clin. Colorectal Cancer*, 10.2 (2011): 73-80.
Kennedy, R. D. et al., Development and independent validation of a prognostic assay for stage II colon cancer using formalin-fixed paraffin-embedded tissue, *Journal of Clinical Oncology*, 29.35 (2011): 4620-4626.
Kurniali. P. C. et al., "Management of locally advanced and metastatic colon cancer in elderly patients," *World Journal of Gastroenterology*, 20.8 (2014): 1910-1922.
Lenz, H-J. et al., "Impact of consensus molecular subtyping (CMS) on overall survival (OS) and progression free survival (PFS) in patients (pts) with metastatic colorectal cancer (mCRC): Analysis of CALGB/SWOG 80405 (Alliance)," *Journal of Clinical Oncology*, 35.15 (2017): Abstract 3511 ASCO.
Marisa, L. et al., "Clinical utility of colon cancer molecular subtypes: Validation of two main colorectal molecular classifications on the PETACC-8 phase III trial cohort," *Journal of Clinical Oncology*, 35.15 (2017): Abstract 3509 ASCO.
(Continued)

*Primary Examiner* — Misook Yu
*Assistant Examiner* — James Lyle McLellan
(74) *Attorney, Agent, or Firm* — pH IP Law

(57) ABSTRACT

Provided herein is a consensus molecular subtype (CMS) classifier for colorectal cancer patients. Also provided are methods of using the classifier to identify a clinically beneficial therapeutic regime for each patient as well as methods of treating a patient accordingly Custom Nanostring code sets, which work on formalin-fixed, paraffin-embedded samples, are provide for use in determining the CMS for a colorectal cancer patient.

17 Claims, 15 Drawing Sheets

Specification includes a Sequence Listing.

(56) References Cited

OTHER PUBLICATIONS

Marisa. L. et al., "Gene expression classification of colon cancer into molecular subtypes: characterization, validation, and prognostic value," *PLoS Med.*, 10.5 (2013): 1-13.

Missiaglia. E. et al., "Distal and proximal colon cancers differ in terms of molecular, pathological, and clinical features," *Annals of Oncology*, 25 (2014): 1995-2001.

Mittempergher, L. et al., "Gene expression profiles from formalin fixed paraffin embedded breast cancer tissue are largely comparable to fresh frozen matched tissue," *PLoS One*, 6.2 (2011): 1-15.

PCT International Preliminary Report on Patentability issued in International Patent Application No. PCT/US2020/026409, dated Oct. 14, 2021.

PCT International Search Report and Written Opinion issued in International Patent Application No. PCT/US2020/026409, dated Sep. 14, 2020.

Qiu, Y. et al., "A Distinct Metabolic Signature of Human Colorectal Cancer with Prognostic Potential," *Clinical Cancer Research*, 20. 8 (2014): 2136-2146.

Roepman. P. et al., "Colorectal cancer intrinsic subtypes predict chemotherapy benefit, deficient mismatch repair and epithelial-to-mesenchymal transition," *International Journal of Cancer*, 134 (2014): 552-562.

Sadanandam, A. et al., "A colorectal cancer classification system that associates cellular phenotype and responses to therapy," *Nat. Med.*, 19.5 (2013): 619-625.

Schlicker, A. et al., "Subtypes of primary colorectal tumors correlate with response to targeted treatment in colorectal cell lines," *BMC Medical Genomics*, 5:66 (2012): 1-15.

Stintzing, S. et al., "Consensus molecular subgroups (CMS) of colorectal cancer (CRC) and first-line efficacy of FOLFIRI plus cetuximab or bevacizumab in the FIRE3 (AIO KRK-0306) trial," *Journal of Clinical Oncology*, 35.15 (2017): Abstract 3510 ASCO.

Sveen, A. et al., "Colorectal Cancer Consensus Molecular Subtypes Translated to Preclinical Models Uncover Potentially Targetable Cancer Cell Dependencies," *Clinical Cancer Research*, 24.4 (2018): 794-806.

Taieb, J. et al., "Oxaliplatin, fluorouracil, and leucovorin with or without cetuximab in patients with resected stage III colon cancer (PETACC-8): an open-label, randomised phase 3 trial," *Lancet Oncol.*, 15 (2014): 862-873.

Thanki, K. et al., "Consensus Molecular Subtypes of Colorectal Cancer and their Clinical Implications," *Int Biol Biomed J*, 3.3 (2017): 1-9.

Tian, S. et al., "A robust genomic signature for the detection of colorectal cancer patients with microsatellite instability phenotype and high mutation frequency," *Journal of Pathology*, 228 (2012): 586-595.

Vinson, G. P. et al., "The Renin-Angiotensin System in The Breast and Breast Cancer," *Endocrine-Related Cancer*, 19 (2012): R1-R19.

Yaffee, P. et al., Review of systemic therapies for locally advanced and metastatic rectal cancer, *J. Gastrointest. Oncol.*, 6.2 (2015): 185-200.

* cited by examiner

SEQUENCE LISTING

```
<160> NUMBER OF SEQ ID NOS: 201

<210> SEQ ID NO 1
<211> LENGTH: 100
<212> TYPE: DNA
<213> ORGANISM: Homo sapiens

<400> SEQUENCE: 1
ttagctagaa gaatttcaag gaaaagaatt ctcagcagag ctcaagattg tagaaactca        60
gcagaagctg gtaaaaacat ggggagcccg gaggacaggc                             100

<210> SEQ ID NO 2
<211> LENGTH: 100
<212> TYPE: DNA
<213> ORGANISM: Homo sapiens

<400> SEQUENCE: 2
agttgaaaac aaggatatat cattggagca agtgttggat cttgtatgga atatggatgg        60
atcacttgta aggacagtgc ctgggaactg gtgtagctgc                             100

<210> SEQ ID NO 3
<211> LENGTH: 100
<212> TYPE: DNA
<213> ORGANISM: Homo sapiens

<400> SEQUENCE: 3
ccaacattga aagcaaagcg aggagagctt tccaaatact ttcggaccca aattgacagc        60
ctgtatgagc acatccagga ttaggataag gtacttaagt                             100

<210> SEQ ID NO 4
<211> LENGTH: 100
<212> TYPE: DNA
<213> ORGANISM: Homo sapiens

<400> SEQUENCE: 4
aaccagatga gaaaaaaatt aagaaattgc tcaagggaaa catttgtaaa tggatttgaa        60
agattgagcc aaattctgtt gtcagttcta agcatgcagt                             100

<210> SEQ ID NO 5
<211> LENGTH: 100
<212> TYPE: DNA
<213> ORGANISM: Homo sapiens

<400> SEQUENCE: 5
taaattttag tcagattttg cccaacctaa tgctctcagg gaaagcctct ggcaagtagc        60
tttctccttc agaggtctaa tttagtagaa aggtcatcca                             100

<210> SEQ ID NO 6
<211> LENGTH: 100
<212> TYPE: DNA
<213> ORGANISM: Homo sapiens

<400> SEQUENCE: 6
```

-continued

```
taaaggctac acacacatat ggagcacccc atcccacagc acattacatc cacctcactt     60
cacagaacgg agaacagagc agaaatgacc agaacacctt                          100

<210> SEQ ID NO 7
<211> LENGTH: 100
<212> TYPE: DNA
<213> ORGANISM: Homo sapiens

<400> SEQUENCE: 7
atacttgctg gggataccat aatgaacaaa acagacctgt tctccgctct tgaggaaatc     60
aaagacaaac acaggatatg gaataaaccc agaattatct                          100

<210> SEQ ID NO 8
<211> LENGTH: 100
<212> TYPE: DNA
<213> ORGANISM: Homo sapiens

<400> SEQUENCE: 8
gaaacatccc tttttgttga gaacctccct tgaatgtctg tcacactcac acctgacggg     60
atggttactg gattagagag tagatttggc acatcttttc                          100

<210> SEQ ID NO 9
<211> LENGTH: 100
<212> TYPE: DNA
<213> ORGANISM: Homo sapiens

<400> SEQUENCE: 9
accaagcttg tggacttcac cccaacaaaa ttgtaagcgt tgttaggttt ttgtgtaaga     60
ttcttgctgt agcgtggata gctgtgattg gtgagtcaac                          100

<210> SEQ ID NO 10
<211> LENGTH: 100
<212> TYPE: DNA
<213> ORGANISM: Homo sapiens

<400> SEQUENCE: 10
tgaagtcttt ccctggtgat ggtcccctgc cctgtctttc cagcatccac tctcccttgt     60
cctcctgggg gcatatctca gtcaggcagc ggcttcctga                          100

<210> SEQ ID NO 11
<211> LENGTH: 100
<212> TYPE: DNA
<213> ORGANISM: Homo sapiens

<400> SEQUENCE: 11
agcacctgct gctgcgattt aaagggaac tgtactactc gcagtgatag gtttgcagag      60
tgtgtgcttg gctgtggcag cctagcttgg agaagctgct                          100

<210> SEQ ID NO 12
<211> LENGTH: 100
<212> TYPE: DNA
<213> ORGANISM: Homo sapiens

<400> SEQUENCE: 12
gttcctaaac cagagtacga ggtccctggg aatttaagta gctacgcatt atctattatt     60
agactgcaag ttcctgcaat aactgcttag ttcacagccc                          100

<210> SEQ ID NO 13
<211> LENGTH: 100
```

<212> TYPE: DNA
<213> ORGANISM: Homo sapiens

<400> SEQUENCE: 13
ggcgttcagg cagccctgat ggaccgaagg ctctggtgtc tggtttggcc ccacagcagt        60
gtgggccgat cctgtttacc tcatacatcc ctgcactgtg                              100

<210> SEQ ID NO 14
<211> LENGTH: 100
<212> TYPE: DNA
<213> ORGANISM: Homo sapiens

<400> SEQUENCE: 14
cggggggcac caacacttgg agatttttcc ggaggggaga ggattttcta agggcacaga        60
gaatccattt tctacacatt aacttgagct gctggaggga                              100

<210> SEQ ID NO 15
<211> LENGTH: 100
<212> TYPE: DNA
<213> ORGANISM: Homo sapiens

<400> SEQUENCE: 15
gtcagtgcct gtcaaggctc cagtcctgct gagccaaagg ctttgtcatt cctttctctt        60
cctgtacatc tgagcagacc cactccagct ttctggtgtc                              100

<210> SEQ ID NO 16
<211> LENGTH: 100
<212> TYPE: DNA
<213> ORGANISM: Homo sapiens

<400> SEQUENCE: 16
gcctttggct aattgagtaa ttcccctcca gcactagaga ccgctcagtg ctcttactag        60
atgaactcag taacgccttg agctgggttg attgaggatg                              100

<210> SEQ ID NO 17
<211> LENGTH: 100
<212> TYPE: DNA
<213> ORGANISM: Homo sapiens

<400> SEQUENCE: 17
cagccgccaa ggacggcaag ctgcacttcg gaattgatcc tgacgatact actatcaccg        60
accttcccta agccgctgga agattgtatt ccagatgcta                              100

<210> SEQ ID NO 18
<211> LENGTH: 100
<212> TYPE: DNA
<213> ORGANISM: Homo sapiens

<400> SEQUENCE: 18
acctgcaagt tgattagaac tgcctttctt cccaggcttg acataggtat taagtcaaaa        60
ttacatgaaa cccagtggta aaaaagcctc tgaaagctgt                              100

<210> SEQ ID NO 19
<211> LENGTH: 100
<212> TYPE: DNA
<213> ORGANISM: Homo sapiens

<400> SEQUENCE: 19
aaatttggtt ttgaatgaac ctgcaaagca tcctgcagcg tgagcagctc ctccacctgg        60

-continued

```
agctccgaag catcttctca ggccaaagcg gcattacccg                        100

<210> SEQ ID NO 20
<211> LENGTH: 100
<212> TYPE: DNA
<213> ORGANISM: Homo sapiens

<400> SEQUENCE: 20
atatagtgta cggcaaaaga gtattaatcc actatctcta gtgcttgact ttaaatcagt    60
acagtacctg tacctgcacg gtcacccgct ccgtgtgtcg                        100

<210> SEQ ID NO 21
<211> LENGTH: 100
<212> TYPE: DNA
<213> ORGANISM: Homo sapiens

<400> SEQUENCE: 21
tattttaaga gactctatct taggagagct taagtgattg ggctgcagga agaagacatt    60
gtaacccagg aattaaaaat ggattcagat tgcctgattt                        100

<210> SEQ ID NO 22
<211> LENGTH: 100
<212> TYPE: DNA
<213> ORGANISM: Homo sapiens

<400> SEQUENCE: 22
attaaaaata taaaactgcg ttaaaggctc gattttgtat ctgcaggcag acacggatct    60
gagaatcttt attgagaaag agcacttaag agaatatttt                        100

<210> SEQ ID NO 23
<211> LENGTH: 100
<212> TYPE: DNA
<213> ORGANISM: Homo sapiens

<400> SEQUENCE: 23
gaagctggca catcttggaa ggtccgtcct gctcggcttt tcgcttgaac attcccttga    60
tctcatcagt tctgagcggg tcatggggca acacggttag                        100

<210> SEQ ID NO 24
<211> LENGTH: 100
<212> TYPE: DNA
<213> ORGANISM: Homo sapiens

<400> SEQUENCE: 24
tctctgagga gtaatttatg ctctagcact ccctttcctc tagatcggcc tgaggctggg    60
acattacatg aaatcacacc cttgctgggc ttaatccctt                        100

<210> SEQ ID NO 25
<211> LENGTH: 100
<212> TYPE: DNA
<213> ORGANISM: Homo sapiens

<400> SEQUENCE: 25
aggatataga agcagcagaa aagtcactac agaccaggat tcacccactt ccacggcctg    60
aggtggtttc tcttgagact cgttactggg catcagtaga                        100

<210> SEQ ID NO 26
<211> LENGTH: 100
<212> TYPE: DNA
<213> ORGANISM: Homo sapiens
```

-continued

<400> SEQUENCE: 26
ggagctccat ctgatccact ggaactccac tctgtttggc agcattgatg aggctgtggg    60
gaagccgcac ggaatcgcca tcattgctct gtttgttcag                          100

<210> SEQ ID NO 27
<211> LENGTH: 100
<212> TYPE: DNA
<213> ORGANISM: Homo sapiens

<400> SEQUENCE: 27
aactcattga gtttctgagc agcttccaaa aagaaaggac ggatgatgag cagttcgctg    60
acgagaagaa ctacttgatt aaacagatcc gagacttgaa                          100

<210> SEQ ID NO 28
<211> LENGTH: 100
<212> TYPE: DNA
<213> ORGANISM: Homo sapiens

<400> SEQUENCE: 28
agtttacata agagaatatc actccgatgg tcggtttctg actgtcacgc taagggcaac    60
tgtaaactgg aataataatg cactcgcaac caggtaaact                          100

<210> SEQ ID NO 29
<211> LENGTH: 100
<212> TYPE: DNA
<213> ORGANISM: Homo sapiens

<400> SEQUENCE: 29
cccttgaaca ggtgaaagct ggaatagaag ctcattcgga agccaaaacc agtggactcc    60
tgtgggctgg attggcactg ctgtccattc agggtggggc                          100

<210> SEQ ID NO 30
<211> LENGTH: 100
<212> TYPE: DNA
<213> ORGANISM: Homo sapiens

<400> SEQUENCE: 30
gaggcggcgc tggaggactg tatgggcaag ttgcagctgc tggtggccat aaacagtact    60
tccttgactc acatgctgcc cgttcagatc tgcgagaagt                          100

<210> SEQ ID NO 31
<211> LENGTH: 100
<212> TYPE: DNA
<213> ORGANISM: Homo sapiens

<400> SEQUENCE: 31
agggctttgt ggaggacagg ccttgccctc aagaacgtcg tacctgacgc tgagcctgtc    60
atgagaatgc aacaggagca aaccaagtgt tgctgtgaca                          100

<210> SEQ ID NO 32
<211> LENGTH: 100
<212> TYPE: DNA
<213> ORGANISM: Homo sapiens

<400> SEQUENCE: 32
agctgaacga cgtcatcggc ctctaggttc cctcattccc cgcgcccttc ccgcccggca    60
ccccacttct gtatacataa acggccaagg tgtgtgcccg                          100

-continued

<210> SEQ ID NO 33
<211> LENGTH: 100
<212> TYPE: DNA
<213> ORGANISM: Homo sapiens

<400> SEQUENCE: 33
taaagatttg tctgatgcca ttgagcaaac ctttcagagg agaaatagtg aaaccaaagt      60
gcgacgtagc acgaggctac agaaggattt agaaaacgaa                            100

<210> SEQ ID NO 34
<211> LENGTH: 100
<212> TYPE: DNA
<213> ORGANISM: Homo sapiens

<400> SEQUENCE: 34
ttcttctgcc cgaagggtaa gtggtgcgtc cagcttacac aatcataatt caaaggttgg      60
tgggcaatgt aatacttaat taaaataatg atggaagagc                            100

<210> SEQ ID NO 35
<211> LENGTH: 100
<212> TYPE: DNA
<213> ORGANISM: Homo sapiens

<400> SEQUENCE: 35
caggaattgg gaggcctagg gtgggcatga aagcttggga agcactgtcg tctctcagac      60
aggcgtccta aagacctcta ggctggaagc ttgggcttgc                            100

<210> SEQ ID NO 36
<211> LENGTH: 100
<212> TYPE: DNA
<213> ORGANISM: Homo sapiens

<400> SEQUENCE: 36
ctcagccttg tttgtactgt atgccttcag cattgcctag gaacacgaag cacgatcagt      60
ccatcccaga gggaccggag ttatgacaag ctttccaaat                            100

<210> SEQ ID NO 37
<211> LENGTH: 100
<212> TYPE: DNA
<213> ORGANISM: Homo sapiens

<400> SEQUENCE: 37
ccccacagat gactccaagg aagctcagat gcctgcagtc attaggtttt agcgtcccat      60
gagccttggt atcaagaggc cacaagagtg ggaccccagg                            100

<210> SEQ ID NO 38
<211> LENGTH: 100
<212> TYPE: DNA
<213> ORGANISM: Homo sapiens

<400> SEQUENCE: 38
tcaagtttag gcctttgtcc agaggtgcaa aatgcaggag cagagagtgt ggattctcag      60
ccaggtcctt ggcacgcctc ctcaggcaag gatgtgcctg                            100

<210> SEQ ID NO 39
<211> LENGTH: 100
<212> TYPE: DNA
<213> ORGANISM: Homo sapiens

<400> SEQUENCE: 39

-continued

```
gaggcttctg ctcgcatacc tgagcagctt gatgtgactg ctcgtggagt ttatgcccca      60
gaggatgtgt acaggttccg gccgactagt gtgggggaat                          100

<210> SEQ ID NO 40
<211> LENGTH: 100
<212> TYPE: DNA
<213> ORGANISM: Homo sapiens

<400> SEQUENCE: 40
actcaccagt cttgctttgg agtgagcaga agagaatgac tattttacgt ggagcatcat      60
tgtgtgactg ttgacctgga cagtcccaag ggctatgcag                          100

<210> SEQ ID NO 41
<211> LENGTH: 100
<212> TYPE: DNA
<213> ORGANISM: Homo sapiens

<400> SEQUENCE: 41
cccagacttg tgttctcttg cgtcccttgg actgcctgtt gattgatgga aagtgtctgc      60
actgacactt ttcgtcagta gtctgtagtt tcgtggcctc                          100

<210> SEQ ID NO 42
<211> LENGTH: 100
<212> TYPE: DNA
<213> ORGANISM: Homo sapiens

<400> SEQUENCE: 42
tgacggatgt ggaagccaca cgtgaggctg tggtgcgtgc ctcgaacctg cccatgtcag      60
tgatcattgt gggtgtgggt ggtgctgact ttgaggccat                          100

<210> SEQ ID NO 43
<211> LENGTH: 100
<212> TYPE: DNA
<213> ORGANISM: Homo sapiens

<400> SEQUENCE: 43
cccctgctgc tgcccaagcc gctgggcctt tttaattgcc aaactgctct cttcatcagc      60
tcagcacatg ctttaagaaa gcaaaaccaa aaaaaaaaaa                          100

<210> SEQ ID NO 44
<211> LENGTH: 100
<212> TYPE: DNA
<213> ORGANISM: Homo sapiens

<400> SEQUENCE: 44
ctgagctggg agaagtgatt aagggagtga aaccagccca ctgtgagaag accaccgtgt      60
tcaagtcttt gggaatggca gtggaagaca cagttgcagc                          100

<210> SEQ ID NO 45
<211> LENGTH: 100
<212> TYPE: DNA
<213> ORGANISM: Homo sapiens

<400> SEQUENCE: 45
ggagagaaaa agcaaatggt atgccacaag atcactctga tttgagaaaa gggaggaggg      60
gaagatagtc tgaatggaaa tctgaaatac ggaatgtttt                          100

<210> SEQ ID NO 46
```

<211> LENGTH: 100
<212> TYPE: DNA
<213> ORGANISM: Homo sapiens

<400> SEQUENCE: 46
tttgtggcaa aaatacttcc taggtggtgc tgggtacttc ttgttgcatc ctgtcaggag      60
gcagataatg ctggtgcctc tctattggta atgttaagac                          100

<210> SEQ ID NO 47
<211> LENGTH: 100
<212> TYPE: DNA
<213> ORGANISM: Homo sapiens

<400> SEQUENCE: 47
gaaatcaaca acaactcaaa agaagtgaat tggaacttac acaaaaatga acacctagaa      60
aaacctaaca aataggcctg cctacaatat tctcattatt                          100

<210> SEQ ID NO 48
<211> LENGTH: 100
<212> TYPE: DNA
<213> ORGANISM: Homo sapiens

<400> SEQUENCE: 48
tgctggccgc cctggttcat atttgagttt aattgtactg accctggacc cagataagca      60
gcaactttgt gtctttgggg tcacagaaca ttttgggca                          100

<210> SEQ ID NO 49
<211> LENGTH: 100
<212> TYPE: DNA
<213> ORGANISM: Homo sapiens

<400> SEQUENCE: 49
aatgtctagt tgttctatat tataaccaca tttgcgctct atgcaagccc ttggaacaga      60
acatactcat cttcatgtag gacctatgaa aattgtctat                          100

<210> SEQ ID NO 50
<211> LENGTH: 100
<212> TYPE: DNA
<213> ORGANISM: Homo sapiens

<400> SEQUENCE: 50
agagacattc actattaatg aagtaaccct tgggcatgac tccaatccca gaattgctca      60
ctgagcgcta tgccaccgaa gcgttgacct gaacatatta                          100

<210> SEQ ID NO 51
<211> LENGTH: 100
<212> TYPE: DNA
<213> ORGANISM: Homo sapiens

<400> SEQUENCE: 51
aattctccat aaaatgggct ttcctctgtc tgccatcctc agagtctggg gtgggagtgt      60
ggacttagga aaacaatata aaggacatcc tcatcatcac                          100

<210> SEQ ID NO 52
<211> LENGTH: 100
<212> TYPE: DNA
<213> ORGANISM: Homo sapiens

<400> SEQUENCE: 52
ttaatcaagg gagatacacc tatcagatgt ttaaaataac aacactaccc actgaaatca      60

-continued

```
gggcatatag aatcattcag ctaaagagtg acttctatga                              100

<210> SEQ ID NO 53
<211> LENGTH: 100
<212> TYPE: DNA
<213> ORGANISM: Homo sapiens

<400> SEQUENCE: 53
aagtattcgt attctcttca tcccagtctg attgcatagc cacactgccc ggcacgccac        60
atccacccct gtctgcacat gagttgttct gacaacagcg                             100

<210> SEQ ID NO 54
<211> LENGTH: 100
<212> TYPE: DNA
<213> ORGANISM: Homo sapiens

<400> SEQUENCE: 54
gctgtgcttg agacttaggt acttttctca cgtggacaca ctgatcccat cccatattgc        60
atcttggaag agatggatat caagtacact ttggtagctg                             100

<210> SEQ ID NO 55
<211> LENGTH: 100
<212> TYPE: DNA
<213> ORGANISM: Homo sapiens

<400> SEQUENCE: 55
aggccaacct gtcccaagtg gccgaccatc tggatcacat caaggaggtg gcaggagcca        60
gagccgtggg ttttggtggg gactttgatg gtgttccaag                             100

<210> SEQ ID NO 56
<211> LENGTH: 100
<212> TYPE: DNA
<213> ORGANISM: Homo sapiens

<400> SEQUENCE: 56
tatatggctg ggatttgaaa agaaaaataa tcagccgtgg ggccaatttt ttaactcaga        60
tcttgctgag accaggagca tctgatttaa caggaagttt                             100

<210> SEQ ID NO 57
<211> LENGTH: 100
<212> TYPE: DNA
<213> ORGANISM: Homo sapiens

<400> SEQUENCE: 57
gctcaaggtg gaagtcttca gacagacagt ggccgaccag gtgctagtag gaagctactg        60
tgtcttcagc aatcagggag ggctggtgca tcccaagact                             100

<210> SEQ ID NO 58
<211> LENGTH: 100
<212> TYPE: DNA
<213> ORGANISM: Homo sapiens

<400> SEQUENCE: 58
ggttggtgtg ctgaggtgtt agagagggac catgtgtcac ttgtgctttg ctcttgtccc        60
acgtgtcttc cactttgcat atgagccgtg aactgtgcat                             100

<210> SEQ ID NO 59
<211> LENGTH: 100
<212> TYPE: DNA
```

-continued

<213> ORGANISM: Homo sapiens

<400> SEQUENCE: 59

```
tttttggcta ctgcaaaaat ctattcagca agaaggtatc agctgcatac cttgcacagt      60
ggagctgact acctataaac tctccctaag gcatttgttt                           100
```

<210> SEQ ID NO 60
<211> LENGTH: 100
<212> TYPE: DNA
<213> ORGANISM: Homo sapiens

<400> SEQUENCE: 60

```
tgagaaccaa agcaaccaca aatgcataaa tgcataattt atggtcttca accaaggcca      60
cataataacc cagttaactt actctttaac caggaatatt                           100
```

<210> SEQ ID NO 61
<211> LENGTH: 100
<212> TYPE: DNA
<213> ORGANISM: Homo sapiens

<400> SEQUENCE: 61

```
gtggctgctt cacttagatg cagtgagaca catagttggt gttccgattt tcacatcctt      60
ccatgtattt atcttgaaga gataagcaca gaagagaagg                           100
```

<210> SEQ ID NO 62
<211> LENGTH: 100
<212> TYPE: DNA
<213> ORGANISM: Homo sapiens

<400> SEQUENCE: 62

```
tactttaaca ccttaaaggg agaagcaaac atttccttct tcagctgact ggcaatggcc      60
ctttaactgc aataggaaga aaaaaaaaaa ggtttgtgtg                           100
```

<210> SEQ ID NO 63
<211> LENGTH: 100
<212> TYPE: DNA
<213> ORGANISM: Homo sapiens

<400> SEQUENCE: 63

```
gctttgatga atacatgaag gagctaggag tgggaatagc tttgcgaaaa atgggcgcaa      60
tggccaagcc agattgtatc atcacttgtg atggtaaaaa                           100
```

<210> SEQ ID NO 64
<211> LENGTH: 100
<212> TYPE: DNA
<213> ORGANISM: Homo sapiens

<400> SEQUENCE: 64

```
ttttcagtga tttcctctga agcagctgca ctgatacatt tgggagttgg tggcttgact      60
ttgtccataa ggggcgtggc cacttcacat gatggcgggc                           100
```

<210> SEQ ID NO 65
<211> LENGTH: 100
<212> TYPE: DNA
<213> ORGANISM: Homo sapiens

<400> SEQUENCE: 65

```
aaattcaatg gtgggataga attaggtcag gaaatggaag ttgttccaat ggtgtgagaa      60
ctaggagaca agatgattca ctttattatt taaaccaagc                           100
```

<210> SEQ ID NO 66
<211> LENGTH: 100
<212> TYPE: DNA
<213> ORGANISM: Homo sapiens

<400> SEQUENCE: 66
ggaaactctt ctctgacttg gggagttcct acgcaaaaca actgggcttc cgggacagct        60
gggtcttcat aggagccaaa gacctcaggg gtaaaagccc                               100

<210> SEQ ID NO 67
<211> LENGTH: 100
<212> TYPE: DNA
<213> ORGANISM: Homo sapiens

<400> SEQUENCE: 67
acagctgtga ttttgttgga cagcaagtat tatggccaaa gccagtttct tggcatttca        60
aaaataatgc aataaaaact agttgaggtt agctgaggct                               100

<210> SEQ ID NO 68
<211> LENGTH: 100
<212> TYPE: DNA
<213> ORGANISM: Homo sapiens

<400> SEQUENCE: 68
tctctgttgc cggatgctgt ctagggcctg ttagttgcta tttccttgcc tccgctcccc        60
ttcccactag ccttctaact accttttatt ctcggctcca                               100

<210> SEQ ID NO 69
<211> LENGTH: 100
<212> TYPE: DNA
<213> ORGANISM: Homo sapiens

<400> SEQUENCE: 69
aaaaagaaaa gtcaggcacc ccaccttaga cctcgtatgc ttgatcctgt gagattgatg        60
tttgtggctg gaggtggatt tcatgccctg tggtgtttac                               100

<210> SEQ ID NO 70
<211> LENGTH: 100
<212> TYPE: DNA
<213> ORGANISM: Homo sapiens

<400> SEQUENCE: 70
ttcatcgtct gtcaggtgga gatgaagaga aatggtgcat gtaaagtgct cagcatctgt        60
gcttagcagg ccatagtctc cctgcctcct ttttcttgag                               100

<210> SEQ ID NO 71
<211> LENGTH: 100
<212> TYPE: DNA
<213> ORGANISM: Homo sapiens

<400> SEQUENCE: 71
ccacacagat accccacgtt ctatataagg aggaaaacgg gaaagaatat aaagttaaaa        60
aaaagcctcc ggtttccact actgtgtaga ctcctgcttc                               100

<210> SEQ ID NO 72
<211> LENGTH: 100
<212> TYPE: DNA
<213> ORGANISM: Homo sapiens -continued

<400> SEQUENCE: 72
aaataggagc ttaagaaaga acattttgcc tgattgagaa gcacaactga aaccagtagc      60
cgctggggtg ttaatggtag cattcttctt ttggcaatac                           100

<210> SEQ ID NO 73
<211> LENGTH: 100
<212> TYPE: DNA
<213> ORGANISM: Homo sapiens

<400> SEQUENCE: 73
tgagaagatc ggaacagctc cttactctga ggaagttgat tcttatttga tggtggtatt      60
gtgaccactg aattcactcc agtcaacaga ttcagaatga                           100

<210> SEQ ID NO 74
<211> LENGTH: 100
<212> TYPE: DNA
<213> ORGANISM: Homo sapiens

<400> SEQUENCE: 74
agctgtcacg tttgtgaaat ccctccagac tacatgcatg cttacctaac agtttgaaat      60
agtattgatc tactgctggt aaccctgctt gatggcagca                           100

<210> SEQ ID NO 75
<211> LENGTH: 100
<212> TYPE: DNA
<213> ORGANISM: Homo sapiens

<400> SEQUENCE: 75
aaaatgttta tccactcttg aagccactcc acaccatcgt gggctatgga agaatgaaaa      60
acctattgga tgaaaatgtc tgcttggatc agggacccgt                           100

<210> SEQ ID NO 76
<211> LENGTH: 100
<212> TYPE: DNA
<213> ORGANISM: Homo sapiens

<400> SEQUENCE: 76
tggtacttgt ttcaccatac ttcattcaga ccagtgaaag agtagtgcat ttaattggag      60
tatctaaagc cagtggcagt gtatgctcat acttggacag                           100

<210> SEQ ID NO 77
<211> LENGTH: 100
<212> TYPE: DNA
<213> ORGANISM: Homo sapiens

<400> SEQUENCE: 77
atggaaggat ataagtatcc agtatatggt gtccagtggc atccagagaa agcaccttat      60
gagtggaaga atttggatgg catttcccat gcacctaatg                           100

<210> SEQ ID NO 78
<211> LENGTH: 100
<212> TYPE: DNA
<213> ORGANISM: Homo sapiens

<400> SEQUENCE: 78
ggtgtatacc ctacagaaat gtgtacatgt gttcatccag agacatgctc taaatcttca      60
caaaaacact ctccataata accccgaaca ggaaagcacc                           100

```
<210> SEQ ID NO 79
<211> LENGTH: 100
<212> TYPE: DNA
<213> ORGANISM: Homo sapiens

<400> SEQUENCE: 79
acatgggttg acatgcacac aacaccattt tcattcagta tgaaccttga ggctgctgcc      60 attttccac ttaaccaaac cagcctgaag gtgaacctcg                            100

<210> SEQ ID NO 80
<211> LENGTH: 100
<212> TYPE: DNA
<213> ORGANISM: Homo sapiens

<400> SEQUENCE: 80
aattgaaatt cacactgcaa gtgaatcctg caacaaaaat gagggtgacc ctgctctccc      60
aacccatgga gacctatgaa ggggatgtgc tgggggtcca                           100

<210> SEQ ID NO 81
<211> LENGTH: 100
<212> TYPE: DNA
<213> ORGANISM: Homo sapiens

<400> SEQUENCE: 81
ggggttttgc tctgtgtgtt tcatatccaa cggcaatact tgcagggggga cagagtcctc      60 taaatactcc aatcctgcgg tttttacaaa cataaagggg                           100

<210> SEQ ID NO 82
<211> LENGTH: 100
<212> TYPE: DNA
<213> ORGANISM: Homo sapiens

<400> SEQUENCE: 82
gtggtgacag ctgccaccat gcaaagcaaa ctgatccaaa aaggaaatga cagaccaaat      60
ggcgaggtga aaagtgaact ctgtgagagt cttgaaacca                           100

<210> SEQ ID NO 83
<211> LENGTH: 100
<212> TYPE: DNA
<213> ORGANISM: Homo sapiens

<400> SEQUENCE: 83
agttctactt cagtttgata aggctataaa tgcagcactg gctcagaggg tcaggaacag      60
agtcaatttc aggggctctc taaatacgta cagattctgc                           100

<210> SEQ ID NO 84
<211> LENGTH: 100
<212> TYPE: DNA
<213> ORGANISM: Homo sapiens

<400> SEQUENCE: 84
aggcagcagg gataagaagc caaaaaccca gacgggtagc cagctataaa aaaggcactc      60
tggaatactt gcagctgaat accacagaca aggagagcac                           100

<210> SEQ ID NO 85
<211> LENGTH: 100
<212> TYPE: DNA
<213> ORGANISM: Homo sapiens

<400> SEQUENCE: 85
```

-continued

```
ctcttggctt ggtctctacc ctcactacct cagttctcaa taacttagtg aatcactgcc      60
ctcctcaaag ccatttccac tcagctcttt ccagagaatt                           100

<210> SEQ ID NO 86
<211> LENGTH: 100
<212> TYPE: DNA
<213> ORGANISM: Homo sapiens

<400> SEQUENCE: 86
gtatccttct cacaaagtag agaccaagag aaaaactcat tgattgggtt tctacttctt      60
tcaaggactc aggaaatttc actttgaact gaggccaagt                           100

<210> SEQ ID NO 87
<211> LENGTH: 100
<212> TYPE: DNA
<213> ORGANISM: Homo sapiens

<400> SEQUENCE: 87
tccacgtgag tgaggataaa gactgggctg ccaaggagga ctcctcataa acattgacaa      60
attgctctgc cccgcctgtg atcccagacg actcctgcag                           100

<210> SEQ ID NO 88
<211> LENGTH: 100
<212> TYPE: DNA
<213> ORGANISM: Homo sapiens

<400> SEQUENCE: 88
actggtggct ttataagaag aggaaaagag aactgagcta gcatgcccag cccacagaga      60
gcctccacta gagtgatgct aagtggaaat gtgaggtgca                           100

<210> SEQ ID NO 89
<211> LENGTH: 100
<212> TYPE: DNA
<213> ORGANISM: Homo sapiens

<400> SEQUENCE: 89
gggagtggtg ggagcagcgg cggcggcggc aatagtttca gcttcagcag cgccagcagt      60
cttagtagca gcagcaccag tgcgggttgc gccagcagcc                           100

<210> SEQ ID NO 90
<211> LENGTH: 100
<212> TYPE: DNA
<213> ORGANISM: Homo sapiens

<400> SEQUENCE: 90
accagcctgc tctccgcagg cccactgtcc ttgggtttaa tgacgtctct tctctgtgga      60
acttcacgat tccttcccac ggtcaactcg ggacctccca                           100

<210> SEQ ID NO 91
<211> LENGTH: 100
<212> TYPE: DNA
<213> ORGANISM: Homo sapiens

<400> SEQUENCE: 91
aatcctctgg agagatggaa gtggactaag tcttaatttt accttcacat taattcaaac      60
cgtgcaagta accacggggt ccatctttta catctggtac                           100

<210> SEQ ID NO 92
<211> LENGTH: 100
```

```
<212> TYPE: DNA
<213> ORGANISM: Homo sapiens

<400> SEQUENCE: 92
gacagagtgg ctgccaaaaa ctcgctggag gcccatgtct tccatgtgaa aggttctttg      60
caagaggaaa gccttaggga caagattccc gaagaggaca                           100

<210> SEQ ID NO 93
<211> LENGTH: 100
<212> TYPE: DNA
<213> ORGANISM: Homo sapiens

<400> SEQUENCE: 93
gcagggtgta tacctgcgca ttgggaactt gctggaaccc ctgatgcatt ttccttgaga      60
gcaggggtac ttccgccttg ccgttagctt gtggagaacg                           100

<210> SEQ ID NO 94
<211> LENGTH: 100
<212> TYPE: DNA
<213> ORGANISM: Homo sapiens

<400> SEQUENCE: 94
tggtagcaat aaatgcttca ggcccacatg atgctgatta gttctcagtt ttcattcagt      60
tcacaatata accaccattc ctgccctccc tgccaagggt                           100

<210> SEQ ID NO 95
<211> LENGTH: 100
<212> TYPE: DNA
<213> ORGANISM: Homo sapiens

<400> SEQUENCE: 95
tgcatattta tataatctct gacttgtaat ggaccctgac tggaatgtga tccctcagga      60
acttagtagc ctgagtcttt cagtagacta cactgcccag                           100

<210> SEQ ID NO 96
<211> LENGTH: 100
<212> TYPE: DNA
<213> ORGANISM: Homo sapiens

<400> SEQUENCE: 96
cctgagttgc tggcattggg aggccagtta ctggaaagga atggaaaaaa gaagcctcca      60
aaagggaaaa acttctgaca atatgatgct gtgcgagaaa                           100

<210> SEQ ID NO 97
<211> LENGTH: 100
<212> TYPE: DNA
<213> ORGANISM: Homo sapiens

<400> SEQUENCE: 97
gtagcctttg tcccttcatg cctttcaatt ctgagtggga ggaaaagcaa acatcaaaac      60
agtgcttcag ccaaattcca tatgtaatgc cattgggaga                           100

<210> SEQ ID NO 98
<211> LENGTH: 100
<212> TYPE: DNA
<213> ORGANISM: Homo sapiens

<400> SEQUENCE: 98
aaatgagcct tttgtggcca cccagtcatc tgcctgcgtg gatggccctg caaaccattg      60
```

-continued agcgtaggat ttgttgcatt atgctagagc accagggtca                            100

<210> SEQ ID NO 99
<211> LENGTH: 100
<212> TYPE: DNA
<213> ORGANISM: Homo sapiens

<400> SEQUENCE: 99
cagccgcagt tggtgctgtg atggccgtga agtgtcctgg gcctcccgag gcctctgaca      60
aataaacaag ccatgagtgg tgaggacaca gtctccttac                            100

<210> SEQ ID NO 100
<211> LENGTH: 100
<212> TYPE: DNA
<213> ORGANISM: Homo sapiens

<400> SEQUENCE: 100
gggttgtcct ggctctgggg agagagacgg agcctttagt acagctatct gctggctcta      60
aaccttctac gcctttgggc cgagcactga atgtcttgta                            100

<210> SEQ ID NO 101
<211> LENGTH: 100
<212> TYPE: DNA
<213> ORGANISM: Homo sapiens

<400> SEQUENCE: 101
tttggcttcc ggctggggca gcatcgaacc agagaatttc tcatttccag atgatctcca      60
gtgtgtggac ctcaaaatcc tgcctaatga tgagtgcaaa                            100

<210> SEQ ID NO 102
<211> LENGTH: 100
<212> TYPE: DNA
<213> ORGANISM: Homo sapiens

<400> SEQUENCE: 102
agccagaatg tgttagaact ctggctgaac atttcatctc ctgtgagtca gaagggcttt      60
atttctccct ttgatggggc cccttcttct ttctggtgct                            100

<210> SEQ ID NO 103
<211> LENGTH: 100
<212> TYPE: DNA
<213> ORGANISM: Homo sapiens

<400> SEQUENCE: 103
ggcgcctagt gtagccatcg agggacttga cttgtgtgtg tttctgaagt gttcgagggt      60
accaggagag ctggcgatga ctgaactgct gatggacaaa                            100

<210> SEQ ID NO 104
<211> LENGTH: 100
<212> TYPE: DNA
<213> ORGANISM: Homo sapiens

<400> SEQUENCE: 104
ttggtgtatt aaaatgactg aatatgaaca ttaaggactc catgaacctg ggctaatggg      60
agactgtaga gaaaatgaaa aaagatccac cagaggacat                            100

<210> SEQ ID NO 105
<211> LENGTH: 100
<212> TYPE: DNA
<213> ORGANISM: Homo sapiens -continued

```
<400> SEQUENCE: 105
aagatacagc aacaatcatt gctactgact tgttcaaccc cttagttaca ctgtatgatc      60
aacatataac aagatacagt ggaatggccc atacagtata                           100

<210> SEQ ID NO 106
<211> LENGTH: 100
<212> TYPE: DNA
<213> ORGANISM: Homo sapiens

<400> SEQUENCE: 106
ttggagataa atgaaataac tggacacaca ctcacacaag taacaccaca gcagacctcg      60
gagtactgct aagtgtacct gtgtcaaatc cgcacaggac                           100

<210> SEQ ID NO 107
<211> LENGTH: 100
<212> TYPE: DNA
<213> ORGANISM: Homo sapiens

<400> SEQUENCE: 107
attttggaga tccctggtcc agaattccat ttaccttctg ggccagatac caccagaatg      60
cccgctccag attccctcag acctttgccg gtcccattat                           100

<210> SEQ ID NO 108
<211> LENGTH: 100
<212> TYPE: DNA
<213> ORGANISM: Homo sapiens

<400> SEQUENCE: 108
tcttggagac taaaaagcag tggacttaat cggttgaccc tactgtggat tggtgggttt      60
cggggtgaag caagttcact acagcatcaa tagaaagtca                           100

<210> SEQ ID NO 109
<211> LENGTH: 100
<212> TYPE: DNA
<213> ORGANISM: Homo sapiens

<400> SEQUENCE: 109
agtgaaggcc atcgttacct tgggatctgc caggctgggg tgttttcggt atctgctgtt      60
cacagctctc cactgtaatc cgaatacttt gccagtgcac                           100

<210> SEQ ID NO 110
<211> LENGTH: 100
<212> TYPE: DNA
<213> ORGANISM: Homo sapiens

<400> SEQUENCE: 110
tttactagaa attcagccga aaagaagaga aatgaagaaa tacttctgga tccaaaggtt      60
cgtcactgga tcagccttaa gaaagtctct atgtgtgcta                           100

<210> SEQ ID NO 111
<211> LENGTH: 100
<212> TYPE: DNA
<213> ORGANISM: Homo sapiens

<400> SEQUENCE: 111
gacaggacag agagacagag cagccctgca ctgtttccc tccaccacag ccatcctgtc       60
cctcattggc tctgtgcttt ccactataca cagtcaccgt                           100
```

<210> SEQ ID NO 112
<211> LENGTH: 100
<212> TYPE: DNA
<213> ORGANISM: Homo sapiens

<400> SEQUENCE: 112
agttttgtgt cagcttccag ctctctgcag ctatcctaat tcagccagta aggttcagtc        60
ttcttgctca ggctcctgaa gggttgattc tcctgataga                             100

<210> SEQ ID NO 113
<211> LENGTH: 100
<212> TYPE: DNA
<213> ORGANISM: Homo sapiens

<400> SEQUENCE: 113
ggttgtgctg aaacagctct tctgagaact tccaaccacc catgctctaa cctggagaca        60
gccatcccct gcctcagaat aagtaccaat tcgtagtaca                             100

<210> SEQ ID NO 114
<211> LENGTH: 100
<212> TYPE: DNA
<213> ORGANISM: Homo sapiens

<400> SEQUENCE: 114
cagggctgca tctgcaaagg ggcgtcggac aagtgcagct gctgcgcctg atgctgggac        60
agccccgctc ccagatgtaa agaacgcgac ttccacaaac                             100

<210> SEQ ID NO 115
<211> LENGTH: 100
<212> TYPE: DNA
<213> ORGANISM: Homo sapiens

<400> SEQUENCE: 115
gacaaaaatg tgtactgtgt aagccttgca aacaaaaaac aacaaaaaag aagcagcagc        60
agcagcctgc tgtgtggcat ctgaactttt ataaaggttt                             100

<210> SEQ ID NO 116
<211> LENGTH: 100
<212> TYPE: DNA
<213> ORGANISM: Homo sapiens

<400> SEQUENCE: 116
gcttataccc aggctgtagc caactaccaa cgtgcctgtt tgtttgttgc tctttccttc        60
tctccatcat agtctgggtg ccagcgccct gaagctccgt                             100

<210> SEQ ID NO 117
<211> LENGTH: 100
<212> TYPE: DNA
<213> ORGANISM: Homo sapiens

<400> SEQUENCE: 117
actcattttc aagttatgga aatgtgtttg tggcatatag gactgtgggg tctgtgtgtg        60
tagtgagagt gtgtagccac tattataact ggaatttaat                             100

<210> SEQ ID NO 118
<211> LENGTH: 100
<212> TYPE: DNA
<213> ORGANISM: Homo sapiens

<400> SEQUENCE: 118

-continued

```
tccatagtct gtctcctcac atctgttagt attgacacag cacagacacc acaagccatc     60
aggttcttca tggggcaggt gaaatacttc taccccatgg                         100

<210> SEQ ID NO 119
<211> LENGTH: 100
<212> TYPE: DNA
<213> ORGANISM: Homo sapiens

<400> SEQUENCE: 119
ccacctccgg ggaggggcac agggctccag atagtaagca cttaaggcaa acagtggatg     60
gcaccaactt ttaaaggtga ctctattaat ggcttcacct                         100

<210> SEQ ID NO 120
<211> LENGTH: 100
<212> TYPE: DNA
<213> ORGANISM: Homo sapiens

<400> SEQUENCE: 120
atgagtctgt aggagcaagg gcacaaactg cagctgtgag tgcgtgtgtg tgatttggtg     60
taggtaggtc tgtttgccac ttgatggggc ctgggtttgt                         100

<210> SEQ ID NO 121
<211> LENGTH: 100
<212> TYPE: DNA
<213> ORGANISM: Homo sapiens

<400> SEQUENCE: 121
ttacatgatg tcaatagtga tggattcctg gatgaacaag aattagaagc cctatttact     60
aaagagttgg agaaagtata tgaccctaaa aatgaagagg                         100

<210> SEQ ID NO 122
<211> LENGTH: 100
<212> TYPE: DNA
<213> ORGANISM: Homo sapiens

<400> SEQUENCE: 122
actttctctg atctgctgtg atccactgaa aatgtgctgg ggtttgttct gctgtcactg     60
tttatgctgc tggaacttag cactgtcttg atttgaagca                         100

<210> SEQ ID NO 123
<211> LENGTH: 100
<212> TYPE: DNA
<213> ORGANISM: Homo sapiens

<400> SEQUENCE: 123
ggccagagac aggaatgtaa ggattggcaa ctgtgttacc tttcaagttt atctcaataa     60
ccaggtcatc agggacccat tgttctcttc agaaccctat                         100

<210> SEQ ID NO 124
<211> LENGTH: 100
<212> TYPE: DNA
<213> ORGANISM: Homo sapiens

<400> SEQUENCE: 124
gttcctggaa ggtgacgtga aagatcactg tgcagcagca atcttgactt ctggaacaat     60
tgccatttgg gacttacttc tcggtcagtg tactgccctc                         100

<210> SEQ ID NO 125
```

-continued

```
<211> LENGTH: 100
<212> TYPE: DNA
<213> ORGANISM: Homo sapiens

<400> SEQUENCE: 125
gtaagaacac caaccaacca aggtttaagt gattaatagg cttgagcacc gggtggcaga      60
tgttctatgc agtgtggttc aagtttcttt gaccgcactt                          100

<210> SEQ ID NO 126
<211> LENGTH: 100
<212> TYPE: DNA
<213> ORGANISM: Homo sapiens

<400> SEQUENCE: 126
tacctgaaca cttgtactct tgaagtcaca acaaaataat gatgagcttt tcacatcacc      60
tttatggttt caatccctag ctcaaagctt cctggaatct                          100

<210> SEQ ID NO 127
<211> LENGTH: 100
<212> TYPE: DNA
<213> ORGANISM: Homo sapiens

<400> SEQUENCE: 127
gccttgtgtg tggagagctt tctatcttac caagtggtag ggctaaaaga acaacagcct      60
ttttggtagt cacatagcag aatgatcaga gttacattgc                          100

<210> SEQ ID NO 128
<211> LENGTH: 100
<212> TYPE: DNA
<213> ORGANISM: Homo sapiens

<400> SEQUENCE: 128
agttcaagaa gaatttgaca ttgacatgga tgcaccagag acagaacgtg cagcggtggc      60
cattcagtct cagttcagaa aattccagaa gaagaaggct                          100

<210> SEQ ID NO 129
<211> LENGTH: 100
<212> TYPE: DNA
<213> ORGANISM: Homo sapiens

<400> SEQUENCE: 129
tgatcaagat agtagtatta ttacacaaga aacttggtct gcagtctgga agcttgtctg      60
ctctatagaa atgaaaatgc agcatgaagt tgacattgtg                          100

<210> SEQ ID NO 130
<211> LENGTH: 100
<212> TYPE: DNA
<213> ORGANISM: Homo sapiens

<400> SEQUENCE: 130
acctctggct taccacatac actatgctaa agtcatcagc cactgctact acatcttgcc      60
agaaggtttc cctcgccaac aaacagttga aatttaaggg                          100

<210> SEQ ID NO 131
<211> LENGTH: 100
<212> TYPE: DNA
<213> ORGANISM: Homo sapiens

<400> SEQUENCE: 131
ctggggaacc ttcagccctg gatgcagggc cttatcgcgg tggccgtgtt cctggtcctc      60
```

-continued

```
gttgcaatcg cctttgcagt caaccacttc tggtgccagg                     100

<210> SEQ ID NO 132
<211> LENGTH: 100
<212> TYPE: DNA
<213> ORGANISM: Homo sapiens

<400> SEQUENCE: 132
acatccctcg gaggaaaaga agagtttgtt gccaccactg agagcaccac agagaccaaa      60
gaacccaaga aggcaaaaag gtcatccaag gaggaagccg                     100

<210> SEQ ID NO 133
<211> LENGTH: 100
<212> TYPE: DNA
<213> ORGANISM: Homo sapiens

<400> SEQUENCE: 133
tggcacctct ggatttatgc aggaagtgcc aactctaatt tcttttatgc catcacactg      60
accttcaacg ttgggcagat cctgctcatc tctgattact                     100

<210> SEQ ID NO 134
<211> LENGTH: 100
<212> TYPE: DNA
<213> ORGANISM: Homo sapiens

<400> SEQUENCE: 134
taaagaaagg gagagaaaga gaagctatat agagaaaagg aaaccactga atcaaagaga      60
gagctccttt gatttcaaag ggatgtcctc agtgtctgac                     100

<210> SEQ ID NO 135
<211> LENGTH: 100
<212> TYPE: DNA
<213> ORGANISM: Homo sapiens

<400> SEQUENCE: 135
atagaaagta gagctgtgta ttaaattaga ctgtgtctct ctgatacctt tacactactg      60
agaatagcat ggttttggcc atgtaaacca attttcaaag                     100

<210> SEQ ID NO 136
<211> LENGTH: 100
<212> TYPE: DNA
<213> ORGANISM: Homo sapiens

<400> SEQUENCE: 136
ctgattgaat tacagactgc gaacaacggc tttcagaatg agggacttcc atcagactct      60
aatgataata gtagcacaaa ttgaaaactt ccccaaagct                     100

<210> SEQ ID NO 137
<211> LENGTH: 100
<212> TYPE: DNA
<213> ORGANISM: Homo sapiens

<400> SEQUENCE: 137
tttcttctac cagacccttc tggtgccaga tcctcttctc aaagctggga ttacaggtgt      60
gagcatagtg agaccttggc gctacaaaat aaagctgttc                     100

<210> SEQ ID NO 138
<211> LENGTH: 100
<212> TYPE: DNA
```

<213> ORGANISM: Homo sapiens

<400> SEQUENCE: 138
agcaaccaag catgaacttg attaagacca gaagtttggg agatgagtcc tggcattatg        60
tctaggacta aagcagtggc tttgtatagc aagctgagta                             100

<210> SEQ ID NO 139
<211> LENGTH: 100
<212> TYPE: DNA
<213> ORGANISM: Homo sapiens

<400> SEQUENCE: 139
caaggagccc tttgtaggac cagtgttctt agtagcgcgc tttgggcagt gtggctgtgt        60
agtgcatagc tacctctgca aggtgataac taagccggca                             100

<210> SEQ ID NO 140
<211> LENGTH: 100
<212> TYPE: DNA
<213> ORGANISM: Homo sapiens

<400> SEQUENCE: 140
cttccttaga aataggttct ggtagcttct gtgcctgggt agtatcagac cagtgggagt        60
aaaccgagtg ttaagtgtca aggtgagaaa gcctcacatt                             100

<210> SEQ ID NO 141
<211> LENGTH: 100
<212> TYPE: DNA
<213> ORGANISM: Homo sapiens

<400> SEQUENCE: 141
gaaatgtgga caaggaggga catttgcata ctcctactgt ctgtgtggtc acagctagtt        60
tctgtcagct gggctctctg ggagaaagct ggctgttgtc                             100

<210> SEQ ID NO 142
<211> LENGTH: 100
<212> TYPE: DNA
<213> ORGANISM: Homo sapiens

<400> SEQUENCE: 142
tcactacatt aacatgcaag agagagagaa gccttgttac atttcctgct atttaacaaa        60
ctgtccaatt aggtcagcaa gcctgttagg gccttcactg                             100

<210> SEQ ID NO 143
<211> LENGTH: 100
<212> TYPE: DNA
<213> ORGANISM: Homo sapiens

<400> SEQUENCE: 143
gtataagtgc ccaagtaatt cactacagcc taaagccttg cctttgtaat ttgacttctg        60
acatgttggc aatcaaagca tgcacttgta acaatgaaaa                             100

<210> SEQ ID NO 144
<211> LENGTH: 100
<212> TYPE: DNA
<213> ORGANISM: Homo sapiens

<400> SEQUENCE: 144
atgaggaggc tcctcctggt caccagcctg gtggttgtgc tgctgtggga ggcaggtgca        60
gtcccagcac ccaaggtccc tatcaagatg caagtcaaac                             100

```
<210> SEQ ID NO 145
<211> LENGTH: 100
<212> TYPE: DNA
<213> ORGANISM: Homo sapiens

<400> SEQUENCE: 145
attgggagtc tgtttgttcc aatgggttga gctgtctttg tcgtggagat ctggaacttt     60
gcacatgtca ctactgggga ggtgttcctg ctctagcttc                          100

<210> SEQ ID NO 146
<211> LENGTH: 100
<212> TYPE: DNA
<213> ORGANISM: Homo sapiens

<400> SEQUENCE: 146
ggaaggagac agacttatta ctagatgatt cgctggtgtc catctttggg aatcgacgtc     60
tcaagaggtt ctccatggtg gtacaggatg gcatagtgaa                          100

<210> SEQ ID NO 147
<211> LENGTH: 100
<212> TYPE: DNA
<213> ORGANISM: Homo sapiens

<400> SEQUENCE: 147
aagaaaagga aagaggatgt gggtcaaata aaacaccgca tggatgttga ttggtgaata     60
ctggtgtaag aaaagggagc tcaggaattt ttattactgt                          100

<210> SEQ ID NO 148
<211> LENGTH: 100
<212> TYPE: DNA
<213> ORGANISM: Homo sapiens

<400> SEQUENCE: 148
agcttgaact ctgtagcctc tcaaatgaag aaggtggctg ttatttagga ctctgtggaa     60
agcaaatcac agtgctgttt ttaatgcctg agaaatgcac                          100

<210> SEQ ID NO 149
<211> LENGTH: 100
<212> TYPE: DNA
<213> ORGANISM: Homo sapiens

<400> SEQUENCE: 149
tactgtccaa gttctttctc aagaaaccac atctggttca gaagagtgtc aagttggact     60
ctttgaactc tgttgctgtc tgagcaatcg tggtgcctag                          100

<210> SEQ ID NO 150
<211> LENGTH: 100
<212> TYPE: DNA
<213> ORGANISM: Homo sapiens

<400> SEQUENCE: 150
aaaagttaga aaacaaaaca aaacagaagt aagataaata gccagaagac cttggcgaca     60
ccacccggcc ctggtagtta aaaaaaagta acaataataa                          100

<210> SEQ ID NO 151
<211> LENGTH: 100
<212> TYPE: DNA
<213> ORGANISM: Homo sapiens
```

-continued

```
<400> SEQUENCE: 151
atgaagcgaa tggaacagtg tgtggagaag acacaaatcc ctgatactgt caatggtgga         60
aattctggaa acttggatgg ggaaaagcca ccagagaaga                               100

<210> SEQ ID NO 152
<211> LENGTH: 100
<212> TYPE: DNA
<213> ORGANISM: Homo sapiens

<400> SEQUENCE: 152
ctgggctgct tctggcccaa tgcagaggtg gacaggttct tcctggcagt gcatggccgc         60
tacttcagga gctgccccat ctcaggcagg gccgtgcggg                               100

<210> SEQ ID NO 153
<211> LENGTH: 100
<212> TYPE: DNA
<213> ORGANISM: Homo sapiens

<400> SEQUENCE: 153
gtagggcagc acagcagagc aggacatgga tgaaatacta ggaatatgca cagtggggca         60
gtgtgggggc ttctcagtaa tggagaacag ttggtgaaac                               100

<210> SEQ ID NO 154
<211> LENGTH: 100
<212> TYPE: DNA
<213> ORGANISM: Homo sapiens

<400> SEQUENCE: 154
ctctgggcat gtctgctaca aatggacaag attatttcag aggtcactga agactgtgat         60
tacatgcacc tgccttagaa ggtaggattt tcttcccagg                               100

<210> SEQ ID NO 155
<211> LENGTH: 100
<212> TYPE: DNA
<213> ORGANISM: Homo sapiens

<400> SEQUENCE: 155
cccgctgtaa acaggtggaa aaggccaagg ttgaagttgg tgtggccacg gcgcttggaa         60
tcctggttgt tgctggatgc tcttttgcga ttaggagata                               100

<210> SEQ ID NO 156
<211> LENGTH: 100
<212> TYPE: DNA
<213> ORGANISM: Homo sapiens

<400> SEQUENCE: 156
tccatatacc tttcaaccta ataagtaact gtgagatgta cagaaaggtg ttcttacatg         60
aagaagggtg tgaaggctga acaatcatgg atttttctga                               100

<210> SEQ ID NO 157
<211> LENGTH: 100
<212> TYPE: DNA
<213> ORGANISM: Homo sapiens

<400> SEQUENCE: 157
aacgaatgca acaagcgcca acacttcctg tgcaagtacc gaccatagag caagaatcaa         60
gattctgcta actcctgcac agccccgtcc tcttcctttc                               100
```

-continued

```
<210> SEQ ID NO 158
<211> LENGTH: 100
<212> TYPE: DNA
<213> ORGANISM: Homo sapiens

<400> SEQUENCE: 158
atggataaga agatcaagga tgttctcaac agtctagagt acagtccctc tcctataagc      60
aagaagctct cgtgtgctag tgtcaaaagc caaggcagac                           100

<210> SEQ ID NO 159
<211> LENGTH: 100
<212> TYPE: DNA
<213> ORGANISM: Homo sapiens

<400> SEQUENCE: 159
ctccatcttt tggaccaagc agttcctttg gggtgtgggg tgagtgctgt tcccagacaa      60
gaaaccaaac cttttcggt tgctgctggg tatggtgact                            100

<210> SEQ ID NO 160
<211> LENGTH: 100
<212> TYPE: DNA
<213> ORGANISM: Homo sapiens

<400> SEQUENCE: 160
gagtcccaga gaggtagaaa ggaggaattt ctgctggact ttatctgggc agaggaagga      60
tggaatgaag gtagaaaagg cagaattaca gctgagcggg                           100

<210> SEQ ID NO 161
<211> LENGTH: 100
<212> TYPE: DNA
<213> ORGANISM: Homo sapiens

<400> SEQUENCE: 161
tgccctgttc cccaagcttg tcaatgttta gagatactat tcgggttgct aaagccatta      60
ttcatagaaa atttctgccc ctacagaagt gtgtgcatgg                           100

<210> SEQ ID NO 162
<211> LENGTH: 100
<212> TYPE: DNA
<213> ORGANISM: Homo sapiens

<400> SEQUENCE: 162
gcttcctgag agctgtctag gtctgtatcc cagattgttg cttaatgaca tctgacagat      60
gcattgtttt ctgaaatcag cttaagacac caattgtggc                           100

<210> SEQ ID NO 163
<211> LENGTH: 100
<212> TYPE: DNA
<213> ORGANISM: Homo sapiens

<400> SEQUENCE: 163
ggactaaacc tgagaatctc gatttcattg aagttaatgt cagcttgccc aggttcaaac      60
tggaagagag ttacactctc aactccgacc tcgcccgcct                           100

<210> SEQ ID NO 164
<211> LENGTH: 100
<212> TYPE: DNA
<213> ORGANISM: Homo sapiens

<400> SEQUENCE: 164
```

-continued

```
ggatcctgac actggagggc agctgtcttg tgcattactt gtgtttccag caccaaagtt      60
gtgggacatg ttgctgtaga ctgctgcgca gtcctgggtg                           100

<210> SEQ ID NO 165
<211> LENGTH: 100
<212> TYPE: DNA
<213> ORGANISM: Homo sapiens

<400> SEQUENCE: 165
ggagaggtga aaagataaaa agcctccttc aaggttaggt tcaggttctg ttttccattt      60
aacctcatgt gccataaagc tgcccaggca caccagagcc                           100

<210> SEQ ID NO 166
<211> LENGTH: 100
<212> TYPE: DNA
<213> ORGANISM: Homo sapiens

<400> SEQUENCE: 166
ttttaagagg gttgaattct tccatcaggt gaacgaaaaa ggcaacaaag taataaatca      60
gtgaatgtgg ccggcagctg tgtttagccc ctccagatgg                           100

<210> SEQ ID NO 167
<211> LENGTH: 100
<212> TYPE: DNA
<213> ORGANISM: Homo sapiens

<400> SEQUENCE: 167
ccgactcatc gagacaacat gcccagttat cagggagtcc tgtgtcacaa ggtctgtctc      60
tgccattgta agcaagtgcc ttgggcgagc tggcctctgc                           100

<210> SEQ ID NO 168
<211> LENGTH: 100
<212> TYPE: DNA
<213> ORGANISM: Homo sapiens

<400> SEQUENCE: 168
ccagggtggg tgggactgag caggatggat tttcttttga taaaagagtc gatgcctgaa      60
agagaaacca tttccttgat tgtgtaagga acttgctgga                           100

<210> SEQ ID NO 169
<211> LENGTH: 100
<212> TYPE: DNA
<213> ORGANISM: Homo sapiens

<400> SEQUENCE: 169
ttgtcactct gaaacctgat gcaacagtgg aatccatgta aaactctctg tgcatctaaa      60
tacttctgga gggcgacaga ttcatgccac ggataaatga                           100

<210> SEQ ID NO 170
<211> LENGTH: 100
<212> TYPE: DNA
<213> ORGANISM: Homo sapiens

<400> SEQUENCE: 170
ggtagttgta actgctaata aaaccagtga ctagaatata agggaggtaa aaaggacaag      60
atagattaat agcctaaata aagagaaaag cctgatgcct                           100

<210> SEQ ID NO 171
<211> LENGTH: 100
```

-continued

```
<212> TYPE: DNA
<213> ORGANISM: Homo sapiens

<400> SEQUENCE: 171
gcctgggtct gtgtcacctg gggcagtgtg dataatgttt agttctgtga cactgttttt      60
tgggggtggc acctggttct ccgatgcctg ggctggtgtc                           100

<210> SEQ ID NO 172
<211> LENGTH: 100
<212> TYPE: DNA
<213> ORGANISM: Homo sapiens

<400> SEQUENCE: 172
ccaaacaaaa tgaaggatta tttacaggag aagcactact gaaagattga gaaccctgca      60
tcttgcactt tgggaataag aacaagagat tgaaatacag                           100

<210> SEQ ID NO 173
<211> LENGTH: 100
<212> TYPE: DNA
<213> ORGANISM: Homo sapiens

<400> SEQUENCE: 173
ctcttctgca agagagccgt ctgcacttcc tgtagcataa agatgaagat gccttctaag      60
aaatttggac acatccctgt ctacacactg ggctttgaga                           100

<210> SEQ ID NO 174
<211> LENGTH: 100
<212> TYPE: DNA
<213> ORGANISM: Homo sapiens

<400> SEQUENCE: 174
ggaaatgctt ctccaccaaa taagggcttt ttcccctatt taaggagcca gatggattga      60
aagatgtgga aataggcagc tgtagatctt gatcttccag                           100

<210> SEQ ID NO 175
<211> LENGTH: 100
<212> TYPE: DNA
<213> ORGANISM: Homo sapiens

<400> SEQUENCE: 175
aacacttgaa ccatggacaa gactctctca agatggcaaa tggctaattg aggttctgaa      60
gttcttcagt acattgctgt aggtcctgag gccagggatt                           100

<210> SEQ ID NO 176
<211> LENGTH: 100
<212> TYPE: DNA
<213> ORGANISM: Homo sapiens

<400> SEQUENCE: 176
atgttctcct gatgtagctt gagatataaa ggaaaggccc tgcacaggtg gctgtttctt      60
gtctgttatg tcagaggaac agtcctgttc agaaaggggc                           100

<210> SEQ ID NO 177
<211> LENGTH: 100
<212> TYPE: DNA
<213> ORGANISM: Homo sapiens

<400> SEQUENCE: 177
acctggtata tcaagtctct gttagtacta ttggcatttaa gaagacttta ccattatttc     60
```

-continued

```
agtgctaggc attattgatt aggtcttggc tccactgttt                     100

<210> SEQ ID NO 178
<211> LENGTH: 100
<212> TYPE: DNA
<213> ORGANISM: Homo sapiens

<400> SEQUENCE: 178
acaaagactc ttcttgcgtc tctgcttcag gtaacttcaa catctccgct gatgagccta      60
taactgtgac acctcctgac tcacaatcat atatctccgt                     100

<210> SEQ ID NO 179
<211> LENGTH: 99
<212> TYPE: DNA
<213> ORGANISM: Homo sapiens

<400> SEQUENCE: 179
gggaccacct ggtattctgt attttcactg gccatattgg aagcagttct agttgcattg      60
tattgagttg tgctggcagt agtttccatg cctgtcaat                       99

<210> SEQ ID NO 180
<211> LENGTH: 100
<212> TYPE: DNA
<213> ORGANISM: Homo sapiens

<400> SEQUENCE: 180
gttcagactg cacggggagg aagttaaagg ctcctagcag gtcctgaatc cagagacaaa      60
aatgctgtgc cttctccaga gtcttatgca gtgcctggga                     100

<210> SEQ ID NO 181
<211> LENGTH: 100
<212> TYPE: DNA
<213> ORGANISM: Homo sapiens

<400> SEQUENCE: 181
tgagtaacag taaagttcat ttatatgtcc atacctagaa gaccagtgca aatactttga      60
gagcacctgg gtctacagga cataattggc atctaaatcc                     100

<210> SEQ ID NO 182
<211> LENGTH: 100
<212> TYPE: DNA
<213> ORGANISM: Homo sapiens

<400> SEQUENCE: 182
cagtgtgtgt tcattgtaaa cacttttggg aaagggctaa acatgtgagg cctggagata      60
gttgctaagt tgctaggaac atgtggtggg actttcatat                     100

<210> SEQ ID NO 183
<211> LENGTH: 100
<212> TYPE: DNA
<213> ORGANISM: Homo sapiens

<400> SEQUENCE: 183
agacggctac atcgacccgg aggagctggc tgagattttc agggcctccg gggagcacgt      60
gacggacgag gagatcgaat ctctgatgaa agacggcgac                     100

<210> SEQ ID NO 184
<211> LENGTH: 100
<212> TYPE: DNA
<213> ORGANISM: Homo sapiens
```

-continued

```
<400> SEQUENCE: 184
cacccagcca gtggtcgagc actgccccgc cgccaaagtc tgcagaatgt gagatgaggt      60
tctcaaggtc acaggcccca gtcccagcct gggggctggc                          100

<210> SEQ ID NO 185
<211> LENGTH: 100
<212> TYPE: DNA
<213> ORGANISM: Homo sapiens

<400> SEQUENCE: 185
agaccccaac tcactgcagt tcatctgaac aacctgagct cctgggccgg ggtggaagga      60
gggggataaa cctaaggccc tgatccaaag cagcctgttg                          100

<210> SEQ ID NO 186
<211> LENGTH: 100
<212> TYPE: DNA
<213> ORGANISM: Homo sapiens

<400> SEQUENCE: 186
aggaggccaa ggagctcttg gagtccaggc tgagggtctt gaagaaggaa ctggaggact      60
gtgaggtgtt ccggtccacg gaaaagaagg agagcaagga                          100

<210> SEQ ID NO 187
<211> LENGTH: 100
<212> TYPE: DNA
<213> ORGANISM: Homo sapiens

<400> SEQUENCE: 187
attttaatag atgtcattgc ttcaagtcta acggcgccgg gaggcctgtt tgagggaaaa      60
cattagtttg aaaaatcccc gttcccttca tccactgccc                          100

<210> SEQ ID NO 188
<211> LENGTH: 100
<212> TYPE: DNA
<213> ORGANISM: Homo sapiens

<400> SEQUENCE: 188
ttaatttcag tcagtcaata gatggcatcc ctcatcaggg ttgccagatg gtgataacag      60
tgtaaggcct tgggtctaag gcatccacga ctggaaggga                          100

<210> SEQ ID NO 189
<211> LENGTH: 100
<212> TYPE: DNA
<213> ORGANISM: Homo sapiens

<400> SEQUENCE: 189
tacctaatgt cattcactaa catggaagag ttgtgaaaat tctagagtgc tgtaaatcct      60
tggcatacac tatgacaaac aacttcatta ctctcccacc                          100

<210> SEQ ID NO 190
<211> LENGTH: 100
<212> TYPE: DNA
<213> ORGANISM: Homo sapiens

<400> SEQUENCE: 190
agagttcaca ctatataaaa cccaacagct tcaactattg ccctttcaac agttttgcca      60
ctgaccggat agaaacggtt tcagtctctg gatggatgtg                          100
```

```
<210> SEQ ID NO 191
<211> LENGTH: 100
<212> TYPE: DNA
<213> ORGANISM: Homo sapiens

<400> SEQUENCE: 191
ggaagtgttg ctctcattgt gtgactcagt gctgctgtcc atcccatgga aacatgggca        60
caatcaagta tttgtccagc ctattgcagg cttttcctga                              100

<210> SEQ ID NO 192
<211> LENGTH: 100
<212> TYPE: DNA
<213> ORGANISM: Homo sapiens

<400> SEQUENCE: 192
agaaaccttg gggatgatgg atatgctttt tgccaccatg agaaggaagg aaggcacttc        60
tgtgttggaa cacacatctg atggatttcc agagaataag                              100

<210> SEQ ID NO 193
<211> LENGTH: 100
<212> TYPE: DNA
<213> ORGANISM: Homo sapiens

<400> SEQUENCE: 193
gaatgttttg tctgttgccg tcagccgaac tttgttatgg agggagcagc ctcacacaag        60
cagaaacact cctgtggatg gtattgtagc atgtattgtt                              100

<210> SEQ ID NO 194
<211> LENGTH: 100
<212> TYPE: DNA
<213> ORGANISM: Homo sapiens

<400> SEQUENCE: 194
cgcaagagtg cgtctcggac agcgaatgcg ccgacaacct caagtgctgc agcgcgggct        60
gtgccacctt ctgctctctg cccaatgata aggagggttc                              100

<210> SEQ ID NO 195
<211> LENGTH: 100
<212> TYPE: DNA
<213> ORGANISM: Homo sapiens

<400> SEQUENCE: 195
tgcctccagt tttaggtcct ttagtttgct tctgtaagca acgggaacac ctgctgaggg        60
ggctctttcc ctcatgtata cttcaagtaa gatcaagaat                              100

<210> SEQ ID NO 196
<211> LENGTH: 100
<212> TYPE: DNA
<213> ORGANISM: Homo sapiens

<400> SEQUENCE: 196
caaagcctgg cctcgccgct cgggagcttt gccatctgag ccacgcctcc tccaggccat        60
gctccttgaa cttggaaatg tcaaccggag cccttacacc                              100

<210> SEQ ID NO 197
<211> LENGTH: 100
<212> TYPE: DNA
<213> ORGANISM: Homo sapiens

<400> SEQUENCE: 197
```

-continued

```
ggttagtgaa gacaaatgtc ttaagaggct gcgatgtcta ggttgggctt gtgacttctt          60
agtggcctag ccttcttgat ggcaccttga aagtgaactt                                100

<210> SEQ ID NO 198
<211> LENGTH: 100
<212> TYPE: DNA
<213> ORGANISM: Homo sapiens

<400> SEQUENCE: 198
aagtcaccct gcagccaggc gaatacatca caaaagtctt tgtcgccttc caagctttcc          60
tccggggtat ggtcatgtac accagcaagg accgctattt                                100

<210> SEQ ID NO 199
<211> LENGTH: 100
<212> TYPE: DNA
<213> ORGANISM: Homo sapiens

<400> SEQUENCE: 199
taatccatac tggaaagaaa ccttacaaat gtagtgattg tgggaagtcc tttagtgtgc          60
gcccaaacct cttcagacat caaattatcc atactaagga                                100

<210> SEQ ID NO 200
<211> LENGTH: 100
<212> TYPE: DNA
<213> ORGANISM: Homo sapiens

<400> SEQUENCE: 200
gcgtgtgttt acctatatgg agtagctcgc agagatcaca gaaatgcttg cagcctaagg          60
cagggttttc agaccgtggg tcccagccca tttagtaaaa                                100

<210> SEQ ID NO 201
<211> LENGTH: 100
<212> TYPE: DNA
<213> ORGANISM: Homo sapiens

<400> SEQUENCE: 201
ggactggttt gaacacaggg tgtgcagatg gggaggggt actggccttg ggcctcctat           60
gatgcagaca tggtgaattt aattcaagga ggaggagaat                                100
```

COLORECTAL CANCER CONSENSUS MOLECULAR SUBTYPE CLASSIFIER CODESETS AND METHODS OF USE THEREOF

REFERENCE TO RELATED APPLICATIONS

The present application is a national phase application under 35 U.S.C. § 371 of International Application No. PCT/US2020/026409, filed Apr. 2, 2020, which claims the priority benefit of U.S. provisional application No. 62/828,098, filed Apr. 2, 2019, the entire contents of each of which are incorporated herein by reference.

REFERENCE TO A SEQUENCE LISTING

The instant application contains a Sequence Listing, which has been submitted in ASCII format via EFS-Web and is hereby incorporated by reference in its entirety. Said ASCII copy, created on Mar. 27, 2020, is named UTFCP1374WO_ST25.txt and is 46.2 kilobytes in size.

BACKGROUND

1. Field

The present invention relates generally to the fields of medicine and oncology. More particularly, it concerns compositions and methods for classifying colorectal cancer as well as using such classification in treating patients having colorectal cancer.

2. Description of Related Art

Colorectal cancer is the third most common cancer and a leading cause of cancer death worldwide. Patients with stage III colon cancer have a 60 to 70% chance of remaining disease-free, with slightly over 50% relative risk reduction with the use of adjuvant 5-FU and oxaliplatin-based regimens. As a result, approximately 1 in 5 patients derive benefit with adjuvant treatment, and for the remaining four patients, the use of adjuvant therapy results in added toxicity with no benefit. Many low-risk stage III patients may opt for single agent 5-FU therapy given the modest absolute risk reduction and added toxicity from oxaliplatin. Conversely, the early identification of high-risk patients allows a more informed discussion about the risks and benefits of adjuvant therapy and a more risk-adapted patient management. Many efforts have been made to identify reliable risk factors to assess individual risk of these patients, including the use of gene expression signatures.

Current efforts in the NCI Colon Cancer Task Force of the GI Steering Committee are focused on identification of high-risk stage III colon cancer and efforts to escalate intensity of adjuvant chemotherapy. This was identified as one of the top three priorities for CRC research in 2015-2016 by the Colon Cancer Task Force. This current push recognizes that there are many high-risk stage III patients that are not being adequately treated with the current regimens given their high recurrence rate. Conversely, international efforts are ongoing to identify the proper intensity of adjuvant therapy including discussions about over-utilization of oxaliplatin for low-risk stage III patients (as exemplified by the CALGB 80702 study of 3 months of FOLFOX chemotherapy instead of 6 months) and treatment intensification (in the ECOG EA2153 study to escalate to FOLFOXIRI in high-risk patients) (Kurniali et al., 2014; Yaffee et al., 2015).

Several reviews have reiterated the importance of prognostication in stage III colon cancer, given the increased recognition of long-term toxicities and heterogeneity of outcomes in the population (Goel et al., 2014; Kelley et al., 2011).

The two most commonly utilized popular and commercially available assays are Oncotype DX (Genomic Health Inc.) and Coloprint (Agendia Inc.). These assays were developed as prognostic biomarkers in stage II and III colon cancers. The Coloprint assay in validation studies demonstrated a five-year relapse-free survival rate for low risk patients of 87.6% for high-risk patients of 67.2% (Kennedy et al., 2011). The hazard ratio in the multivariate model was 2.69 (P=0.003). While this assay provides strong prognostic information, the assay requires fresh frozen tissue for analysis. Although a prospective study is ongoing, the fresh tissue requirement precludes practical application in the community. Efforts to transfer this signature from an Agilent array to formalin fixed paraffin embedded samples using the same platform have not been successful and are no longer being pursued. The Oncotype DX assay in contrast has been designed to utilize FFPE samples and utilizes a 13-gene RT-PCR technique that is more robust to sample degradation. In the validation cohorts for this assay the interquartile range was fairly narrow in the continuous recurrence score and resulted in a hazard ratio of 1.38 (P=0.004) (Goel et al., 2014). A second validation looking at the NSABP C07 study utilized tertiles of risk and identified only as an 8%-9% difference in absolute risk between the groups in stage III colon cancer. Other tools have not been as well studied and have similarly poor performance in multivariate overall survival models in mixed cohorts of stage II and III colon cancer (Mittempergher et al., 2011; Kelley et al., 2011). As such, there is a clear need for better tools to prognosticate stage III patients to help with implementation of value-based patient management decisions.

SUMMARY

Provided herein is a gene set and customized list of gene probes for use in classifying patients with colorectal cancer into one of four consensus molecular subtypes (CMS) (as defined by Guinney et al., (2015)) based on either fresh frozen (FF) or formalin-fixed paraffin embedded (FFPE) samples taken from the patient's primary tumor, applicable in the single sample clinical setting. This can be used to identify patients with poor prognosis to target for more aggressive therapy as well as identify subsets of patients for administration of novel targeted therapy based on CMS-specific biology.

In one embodiment, provided herein are methods of classifying a cancer status of a subject having colorectal cancer, comprising: (a) obtaining a tumor sample from the subject; (b) measuring an expression level of a plurality of genes in the tumor sample, wherein each gene in the plurality of genes is selected from Table 1; (c) generating an expression profile based on a comparison between the expression level of the plurality of genes in the sample from the subject and a corresponding expression level obtained from a reference sample derived from a different subject having a known cancer status; and (d) categorizing the cancer status of the subject based on the expression profile. In some aspects, step (c) comprises applying a weighted support vector machine to the expression level of the plurality of genes.

In some aspects, the plurality of genes comprises 75 genes selected from Table 1. In some aspects, the plurality of genes comprises 80, 85, 90, 95, 100, 105, 110, 115, 120, 125, 130, 135, 140, 145, 150, 155, 160, 165, 170, 175, 180, 185, 190, or 195 genes selected from Table 1. In some aspects, the plurality of genes comprises all 200 genes selected from Table 1. In some aspects, the plurality of genes comprises the 75-gene classifier from Table 1. In some aspects, wherein the plurality of genes comprises the 100-gene classifier from Table 1. In some aspects, the cancer status is categorized as CMS1, CMS2, CMS3, CMS4. The CMS classification may be determined based on a weighted support vector machine applied to these gene sets, which gives a probability of each CMS type for the sample, and classification occurring if the probability is greater than, for example, 0.50 for any CMS type.

In some aspects, if the cancer is a CMS1 cancer, then the following genes tend to be downregulated compared to a reference sample derived from a healthy subject and/or another CMS subtype: ATP9A, WFDC2, VAV3, CEBPA, LEFTY1, DIDO1, CHN2, PRAP1, FITM2, NOL4L, SHLD1, FAM84A, DACH1, ABAT, DPEP1, ARID3A, PRR15, ATP10B, PLCB1, QPRT, AMACR, DAPK2, FRZB, PRDX5, MYRIP, GNG4, ILDR1, GRM8, GUCY2C, HUNK, GPR153, ASCL2, GPR143, PBX1, PCP4, ACSL5, OTULINL, PPP1R14D, RNF43, PRLR, GPCPD1, SHROOM4, PTPRO, ACE2, TSPAN6, TNNC2, CACNA1D, SLC30A2, CAB39L, PPP1R14C, AXIN2, IMMP2L, CTTNBP2, SPIRE2, RETNLB, GGH, NR1I2, GYG2, SEMASA, CDHR1, MAGED1, and HEPH. In some aspects, if the cancer is a CMS1 cancer, then the following genes tend to be upregulated compared to a reference sample derived from a healthy subject and/or another CMS subtype: ENO2, KCTD1, TRNP1, NUCB2, SLC25A37, ERRFI1, MCUB, RARRES3, TFAP2A, SLC4A11, APOL1, IFIT3, ZWINT, DEPDC1, PAK6, TNS4, PRC1, CDCA2, TMEM64, HSPA4L, GTF2A2, KCNK1, ASPH, MT2A, PNP, ADGRG6, RAB27B, BST2, DOCK5, TRIM7, USP14, and SOCS6.

In some aspects, if the cancer is a CMS2 cancer, then the following genes tend to be downregulated compared to a reference sample derived from a healthy subject and/or another CMS subtype: RAMP1, CDC42EP2, CTSE, ENO2, PALLD, KCTD1, HLA-E, TRNP1, NEDD9, NUCB2, SLC25A37, ERRFIL MCUB, PPP3CA, RARRES3, TCN1, TFAP2A, MLPH, SLC4A11, REG4, APOL1, LMO4, and CREB3L1. In some aspects, if the cancer is a CMS2 cancer, then the following genes tend to be upregulated compared to a reference sample derived from a healthy subject and/or another CMS subtype: VAV3, CEBPA, CHN2, PRAP1, FITM2, NOL4L, SHLD1, DACH1, ABAT, DPEP1, ARID3A, PRR15, QPRT, AMACR, DAPK2, PRDX5, MYRIP, GNG4, GRM8, HUNK, ASCL2, GPR143, ACSL5, OTULINL, PPP1R14D, RNF43, PRLR, GPCPD1, SHROOM4, PTPRO, ACE2, TSPAN6, TNNC2, CACNA1D, SLC30A2, CAB39L, PPP1R14C, AXIN2, IMMP2L, CTTNBP2, SPIRE2, GGH, NR1I2, GYG2, SEMASA, CDHR1, FARP1, CEL, TOMM34, PIGU, FAM122B, EREG, MAPRE1, ZDHHC23, CKAP2, SESN1, EIF6, MLLT3, PITX2, EPB41L4B, NDFIP2, PDP1, PPP1R3D, PCMTD2, UPF3A, SRPK1, CDCA7, ANKRD27, DPM1, CPNE1, and JADE3.

In some aspects, if the cancer is a CMS3 cancer, then the following genes tend to be downregulated compared to a reference sample derived from a healthy subject and/or another CMS subtype: SLCO2B1, AHNAK2, LDLRAD3, ZCCHC24, OSTM1, IFIT3, MPP1, CSGALNACT2, RBMS1, and CYTH3. In some aspects, if the cancer is a CMS3 cancer, then the following genes tend to be upregulated compared to a reference sample derived from a healthy subject and/or another CMS subtype: WFDC2, RETNLB, NEDD9, TCN1, MLPH, REG4, CREB3L1, MRAP2, ZG16B, SAMD5, BCL2L15, PIGR, ST6GALNAC1, SLC9A2, FAM3D, RNF183, CRYM, CDC42EP5, SERPINB1, TMEM61, GALNT8, FOXA2, KLK1, HES2, FBXO34, MAP2K6, RAP1GAP, XBP1, CA8, and ASRGL1.

In some aspects, if the cancer is a CMS4 cancer, then the following genes tend to be downregulated compared to a reference sample derived from a healthy subject and/or another CMS subtype: PDZK1IP1, CCNO, ANP32B, AGR2, CENPE, POLD3, POP1, KIF2C, ZWINT, MRAP2, TC2N, ZG16B, FABP5 PLCH1, NCAPH, GFPT1, SAMD5, BCL2L15, PIGR, CARMIL1, DEPDC1, ASF1B, ST6GALNAC1, PAK6, RAN, SLC9A2, UGT8, PALB2, UTP15, TNS4, TNFRSF11A, PRC1, and ARHGAP32. In some aspects, if the cancer is a CMS4 cancer, then the following genes tend to be upregulated compared to a reference sample derived from a healthy subject and/or another CMS subtype: PBX1, PCP4, PALLD, AHNAK2, ZCCHC24, CSGALNACT2, RBMS1, CYTH3, PDZD2, HLX, DACT1, ZNF415, C3orf14, and ZSCAN18.

In some aspects, if the cancer is a CMS1 or CMS3 cancer, then the following genes tend to be upregulated compared to a reference sample derived from a healthy subject and/or a CMS2 or CMS4 cancer: GALNT5, FUT8, SLCO1B3, and CEP192. In some aspects, if the cancer is a CMS1 or CMS4 cancer, then the following genes tend to be upregulated compared to a reference sample derived from a healthy subject and/or a CMS2 or CMS3 cancer: ACSL5, OTULINL, PPP1R14D, and RNF43. In some aspects, if the cancer is a CMS2 or CMS3 cancer, then the expression of ESRP1 is upregulated compared to a reference sample derived from a healthy subject and/or a CMS1 or CMS4 cancer. In some aspects, if the cancer is a CMS2 or CMS4 cancer, then the expression of HOXD11 is upregulated compared to a reference sample derived from a healthy subject and/or a CMS1 or CMS3 cancer.

In some aspects, the expression level of the plurality of genes is measured by detecting a level of mRNA transcribed from the plurality of genes. In some aspects, the expression level is measured using nanostring probes. In certain aspects, the nanostring probes hybridize to the target sequence listed in Table 1 for each of the plurality of genes. In some aspects, the expression level of the plurality of genes is measured by detecting a level of cDNA produced from reverse transcription of mRNA transcribed from the plurality of genes. In some aspects, the expression level of the plurality of genes is measured by detecting a level of polypeptide encoded by the plurality of genes. In some aspects, the sample is a formalin-fixed, paraffin-embedded sample. In some aspects, the sample is a fresh frozen sample.

In some aspects, the methods further comprise reporting the cancer status of the subject. In some aspects, the reporting comprises preparing a written or electronic report. In some aspects, the methods further comprise providing the report to the subject, a doctor, a hospital, or an insurance company.

In one embodiment, provided herein are methods of assessing a likelihood of a subject having colorectal cancer exhibiting a clinically beneficial response to treatment, the method comprising: (a) obtaining a cancer status determined according to the method of any one of the present embodiments; and (b) assessing a likelihood of the cancer exhibiting a clinically beneficial response to treatment based on the cancer status.

In some aspects, the methods further comprise reporting whether the subject is likely to exhibit a clinically beneficial response to treatment. In some aspects, reporting comprises preparing a written or electronic report. In some aspects, the methods further comprise providing the report to the subject, a doctor, a hospital or an insurance company.

In some aspects, if the subject is determined to have a CMS1 cancer, then the subject is likely to exhibit a clinically beneficial response to treatment with HSP90 inhibitors, bevacizumab, atorvastatin, 2-methoxyestradiol, indibulin, tipifarnib, or disulfiram. In some aspects, if the subject is determined to have a CMS2 cancer, then the subject is likely to exhibit a clinically beneficial response to treatment with cetuximab, EGFR inhibitors, or HER2 inhibitors. In some aspects, if the subject is determined to have a CMS3 cancer, then the subject is likely to exhibit a clinically beneficial response to treatment with cetuximab, EGFR inhibitors, or HER2 inhibitors. In some aspects, if the subject is determined to have a CMS4 cancer, then the subject is likely to exhibit a clinically beneficial response to treatment with HSP90 inhibitors, bevacizumab, atorvastatin, 2-methoxyestradiol, indibulin, tipifarnib, or disulfiram.

In one embodiment, provided herein are methods of treating a patient having colorectal cancer, the method comprising obtaining a cancer status determined according to the method of any one of the present embodiments and administering an anti-cancer therapy to the subject. In some aspects, the anti-cancer therapy is a chemotherapy, a radiation therapy, a hormonal therapy, a targeted therapy, an immunotherapy or a surgical therapy.

In some aspects, if the subject is determined to have a CMS1 cancer, then administering HSP90 inhibitors, bevacizumab, atorvastatin, 2-methoxyestradiol, indibulin, tipifarnib, or disulfiram. In some aspects, if the subject is determined to have a CMS2 cancer, then administering cetuximab, an EGFR inhibitor, or a HER2 inhibitor. In some aspects, if the subject is determined to have a CMS3 cancer, then administering cetuximab, an EGFR inhibitor, or a HER2 inhibitor. In some aspects, if the subject is determined to have a CMS4 cancer, then administering HSP90 inhibitors, bevacizumab, atorvastatin, 2-methoxyestradiol, indibulin, tipifarnib, or disulfiram.

In one embodiment, provided herein are compositions comprising a set of nanostring probes that hybridize to the target sequence for at least 75 of the genes listed in Table 1. In some aspects, the compositions comprise nanostring probes that hybridize to the target sequence for at least 80, 85, 90, 95, 100, 110, 120, 130, 140, 150, 160, 170, 180, or 190 of the genes listed in Table 1. In some aspects, the compositions comprise nanostring probes that hybridize to the target sequence for all 100 of the genes in the 100 gene set listed in Table 1. In some aspects, the composition comprises nanostring probes that hybridize to the target sequences for all 100 genes in the 100 gene set listed in Table 1. In some aspects, the composition comprises nanostring probes that hybridize to the target sequences for at least 100, 110, 120, 130, 140, 150, 160, 170, 180, 185, 190, or 195 of the genes in the 200 gene set listed in Table 1. In some aspects, the composition comprises nanostring probes that hybridize to the target sequences for all 200 genes in the 200 gene set listed in Table 1.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, the variation that exists among the study subjects, or a value that is within 10% of a stated value.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4A—Histogram of sample-wise Spearman correlation of paired FF/FFPE values across all 472 CMS genes on Nanostring assay, with threshold of 0.75 marked with red vertical line.

DETAILED DESCRIPTION

Figure 1:
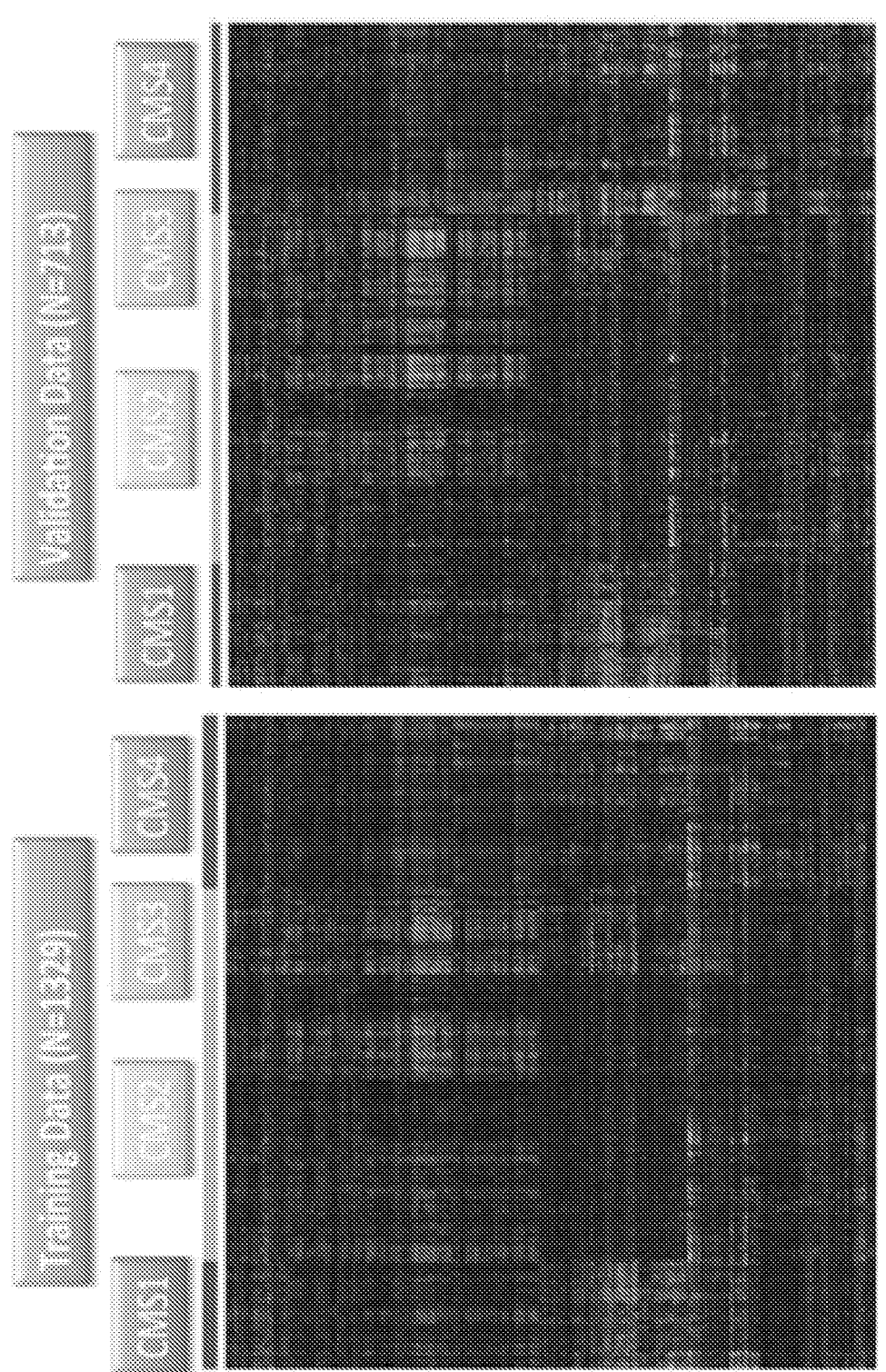
FIG. 1. Persistence of Structure in CMS groups. Heatmap of top 472 genes (rows) for discriminating CMS (columns) for independent training and validation cohorts, with columns sorted within CMS and rows sorted by clustering genes in the training data.

Using a network analysis combining information across six previously published subtyping systems and 4,151 samples from 18 studies, Guinney et al. (2015) found that colorectal cancer patients tend to cluster within four consensus molecular subtypes (CMS) that appear to have different molecular characteristics based on RNA expression data from fresh frozen colorectal cancer patient samples. These CMS provide prognostic information, provide predictive information for current treatments, and allow for the partitioning of the disease into biologically distinct subgroups that can be characterized and investigated to discover new subtype-specific precision therapy strategies. In order to realize this potential, reliable methods to classify patients into CMS based on formalin-fixed paraffin-embedded (FFPE) samples from primary colorectal cancers are essential. As such, provided herein are novel custom-designed Nanostring code sets that yield accurate CMS classifications for FFPE samples based on mRNA and/or non-coding RNA (e.g., miRNA) expression.

First, a CMS classifier for fresh frozen (FF) samples was constructed and validated using data from the colorectal cancer subtyping consortium (CRCSC; Guinney et al., 2015). A rigorous, detailed investigation was performed to get an optimized predictor in which numerous classification approaches were compared. The best predictor was chosen based on cross-validation of a training data set, and then its classification accuracy was assessed in a validation data set as a function of the number of genes in the model, with genes ranked according to a multi-class boosting algorithm. Custom Nanostring code sets were designed based on the best probes for the genes in this classifier, and then these code sets were run on 152 paired FF/FFPE samples, with 78 from patients among the consensus cohort in Guinney et al. (2015) and 74 others for which an Affymetrix classifier was also run on FF samples to obtain pseudo-gold standard CMS. The Nanostring FFPE-based classifier was developed by first identifying a subset of genes with high correlation between FF and FFPE samples, using a subset of the CRCSC data set to retrain the FF-based classifier based on this reduced set of genes, and then transforming the measurements of the Nanostring FFPE assay to the scale of the Affymetrix FF data from the CRCSC samples so that classifier could be directly applied. This strategy allowed for efficient use of available information, taking advantage of the large CRCSC data set to train a stable model and using the smaller paired FF/FFPE data to select the genes with high correlation across the two sample types and assess classification accuracy on FFPE samples by comparing with the gold standard CMS. The performance of the classifier was validated on multiple platforms, including Affymetrix, RNAseq, and Nanostring FF or FFPE.

Based on cross-validation, the best classifier was found to be a weighted support vector machine, which had outstanding CMS predictive accuracy in the validation data set (>0.93) for models with at least 75 genes. To move forward, a 472-gene model was chosen that had 4-group CMS classification accuracy of 95.9%, an improvement over the classifiers presented in Guinney et al. (2015) (94.2% and 93.2% for random forest and single sample classifier, respectively), and custom Nanostring codesets were designed based on the optimal Affymetrix probe for each gene along with 28 housekeeping genes with high expression, low variance, and non-differential expression across CMS. The gene expression values from the Nanostring codesets were found to be reproducible (median CV=0.11), and 100/472 codesets had a FF/FFPE correlation of at least 0.80, reproducibly across cohorts. The resulting Nanostring FFPE-based classifier based on this 100-gene signature had four-group classification accuracy of 80.4%, with samples classified with higher confidence having greater accuracy, but with performance stable across mRNA quality/quantity. The Nanostring classifier also performed well on FF samples, with four-group classification accuracy of 81.0%.

This Nanostring FFPE-based CMS can be used to stratify patient samples by CMS to administer CMS-based precision therapy strategies.

I. Consensus Molecular Subtypes for Colon Cancer

The inventors have participated in an international consortium (CRCSC) whose primary goal was to identify consensus molecular subtypes of colorectal cancer, based on an aggregative network analysis of RNA expression and independent of patient treatments or outcomes. Through an unprecedented level of data sharing across eighteen CRC gene expression data sets (n=4,151 patients) and analytical collaboration, this group identified four consensus molecular subtypes (CMS), each with its own distinguishing characteristics (Guinney et al., 2015; Dienstmann et al., 2017). CMS1 (Immune, 17.5%) is characterized by enrichment in hypermutation, hypermethylation, microsatellite instability, and immune activation. CMS2 (Canonical, 42%) demonstrates canonical CRC characteristics, including epithelial differentiation, MYC and WNT activation, and high levels of chromosomal instability. CMS3 (Metabolic, 13%) is epithelial and showed high levels of metabolic dysregulation, with higher rates of KRAS mutation. CMS4 (Mesenchymal, 27.5%) shows characteristics of epithelial mesenchymal transition (EMT), activation of TGFβ, angiogenesis, and prominent reactive stroma. These subtypes were persistently present in all data sets, were reproducible, and robustly defined independent of the assay used to measure RNA expression. While certain molecular patterns are enriched within specific subgroups (BRAF, MSI, KRAS), these mutations do not fully recapitulate the subtypes and substantial heterogeneity remains within many molecular subtypes, as epitomized by KRAS mutation. The consensus subgroups do substantially incorporate subgroups previously defined by closely related tumors that do not carry the alteration in question (so-called MSI-like, and BRAF-like gene expression signatures) (Missiaglia et al., 2014; Tian et al., 2012).

Prognostic significance of CMS4: Despite the fact that these subgroups were discovered based on global biology, and not any prognostic or predictive considerations, these CMS have been found to have potential prognostic and predictive value in precision therapy strategies. First, CMS4 has potential as a prognostic biomarker for stage II-III that can be useful to stratify patients for clinical trials or select patients for more aggressive treatment. Guinney et al. (2015) showed that CMS4 (mesenchymal) demonstrates clearly worse progression free and overall survival in stage II-III patients relative to other CMS and has the potential to identify a subset of poor prognosis patients for more aggressive or alternative therapy. These results were affirmed in the PETACCIII study (Marisa et al., 2017). Patients with Stage III have a 60%-70% chance of remaining disease free, with a >50% relative risk reduction with use of adjuvant 5-FU and oxaliplatin-based regimens. Clinical information on 475 stage III patients from seven clinical cohorts was used to define the CMS groups, with an individual median follow-up time of 4.9y (range 0.5y-16.7y). Based on Cox regression, CMS4 patients had higher risk of death than non-CMS4 patients (HR=2.26, p<0.001, 95% CI 1.41-3.61) after adjusting for known prognostic factors: age, pT, pN, gender, and MSI status. Stage III CMS4 patients had a 5-year survival rate of 0.53 (95% CI 0.44-0.64), while non-CMS4 patients' 5-year survival rate was 0.74 (95% CI 0.68-0.79). For stage II-III patients, CMS4 also had higher recurrence risk than non-CMS4 (H=1.73, p=0.002, 95% CI 1.22-2.46). This is consistent with three studies that have shown similar poor prognosis in stage II and III colon cancer with mesenchymal signatures (Marisa et al., 2013; Roepman et al., 2014; Budinska et al., 2013).

Better performance than OncotypeDX Colon: As the Oncotype DX is the most commonly studied gene expression assay, a prognostic score was constructed based on the published genes and algorithm (Kennedy et al., 2011) using expression data from these samples. Dichotomizing these scores (High=top 25%, Low=bottom 75%), only marginal significance (HR=1.69, p=0.02, 95% CI 1.09-2.62) was found after multivariate analysis, similar to prior independent validation in clinical trials (HR=1.34). CMS4 remained an independent prognostic factor even after adjusting for OncotypeDX score in addition to prognostic factors: age, pT, pN, gender, and MSI status (HR=2.27). From these results, the CMS4 subgroup was found to be associated with worse overall survival for stage III colon cancer, and represents a robust, clinically meaningful assay. CMS1 also is a potentially poor prognostic group for metastatic or post-relapse CRC patients. Guinney et al. (2015) showed that CMS1 (Immune) patients had worse overall survival than CMS2-4 after relapse, and this agreed with results from two large clinical trials showing that for metastatic patients, CMS1 patients had significantly worse survival than patients in the other CMS groups (Stintzing et al., 2017; Lenz et al., 2017). Given these results, CMS1 may be a subgroup to target for more aggressive treatment following relapse.

Potential CMS-based targeted therapy strategies: In addition, there have been extensive efforts in the past several years in the CRC research and pharmaceutical communities to understand the specific molecular biological characteristics of each CMS and put this information to work to find whether CMS represent subgroups differentially responding to existing therapies, or to develop CMS-specific therapy strategies designed to target the CMS-specific biological characteristics. There is also evidence of the potential of CMS being predictive of response to existing therapies. Mesenchymal features have been associated with resistance to adjuvant chemotherapy (Roepman et al., 2014). For example, CMS4 may be predictive in determining oxaliplatin benefit in C-07, where patients are randomized to 5-FU+/−oxaliplatin. Preclinical experiments demonstrate that mesenchymal transition is associated with reduced dependence of EGFR signaling (Barr et al., 2008). In certain high-risk subgroups, cetuximab may improve outcomes in the adjuvant setting (Taieb et al., 2014). In the metastatic setting, preliminary data demonstrate a statistically significant impact of CMS4 on cetuximab sensitivity in a single agent study (HR 2.0, P=0.03, in KRAS wild type). Results from the randomized CALGB/SWOG 80405 study (Lenz et al., 2017) found that CMS1 KRASwt patients had longer OS and PFS on FOLFOX/FOLFIRI+bevacizumab than FOLFOX/FOLFIRI+cetuximab, and that CMS2 KRASwt patients had longer OS on FOLFOX/FOLFIRI+cetuximab than FOLFOX/FOLFIRI+bevacizumab, while results from the randomized FIRE3 study (Stinzing et al., 2017) found that CMS4 KRASwt patients with FOLFIRl+cetuximab had significantly improved OS and PFS than patients given FOLFIRI+bevacizumab. Together, these suggest that CMS may be useful for selecting patients for cetuximab therapy. Similarly, the CMS impact is being explored in randomized studies of regorafenib, where increased benefit in CMS3 was seen in the CORRECT study (HR 0.29, P=0.01) with validation planned in the CONCUR study. Similarly, irinotecan (PETACC-3) and ziv-aflibercept (VELOUR) differential efficacy is being explored, and positive results would prompt increased need for a CMS assay to validate and apply to the clinic. Collectively, these demonstrate the substantial predictive benefit that CMS can provide for CRC therapy.

Another exciting application of CMS is the potential of identifying new CMS-specific targeted therapies that may be discovered after deeply characterizing the distinct molecular biology underlying the various CMS. As CMS-specific targets and preclinical models are developed, there is potential for CMS to lead to the discovery of new precision therapy strategies that would have been missed without consideration of CMS. For example, suppose there is a treatment targeting the biology of one of the less prevalent CMS (e.g., CMS3 at <15%) that has a dramatic response rate (e.g., 33%) among CMS3, but no response in other CMS. Absent CMS, this treatment would appear to have little to no activity in the overall CRC cohort (e.g., <5% in our example) and may not be further studied, thus missing an extremely effective targeted therapy for a sizable subset of CRC patients. Incorporation of CMS in studies will allow the identification any such potential targeted therapies and offers hope of CMS-driven precision therapy strategies in the future.

Need for clinical CMS classifier device: In order to realize these potential benefits from CMS, it is necessary to have a robust, reliable classifier to discern a CRC patient's CMS from their primary tumor tissue. Guinney et al. (2015) presented a Random Forest (RF) classifier that involved 5,973 genes and was built primarily using microarrays designed for use with fresh frozen (FF) samples. No efforts were made in that paper to build or optimize a more parsimonious classifier using fewer genes. A 5,973-gene classifier is not practical for clinical use, and more importantly the widespread clinical adoption and use of tissue-based markers is practical only through the use of FFPE tissue, as FF samples are generally not available in a community practice setting. The poor reproducibility of microarray-based genetic signatures between FF and FFPE has been a major challenge in moving gene expression signatures into a standard of care setting in colon cancer (Al-Mulla et al., 2011) and other solid tumors (Al-Mulla et al., 2011; Maes et al., 2013; Wood et al., 2010; Wright et al., 2003; Xue et al., 2015). Formalin fixation induces protein-nucleic acid crosslinks modifying the RNA and high temperature during the tissue embedding accelerates and strengthens these crosslinks (Dietel et al., 2013; Jacobs et al., 2012a; Jacobs et al., 2012b; Potluri et al., 2015). Long-term storage in paraffin blocks leads to fragmentation of RNA and DNA (Dietel et al., 2013). These factors and others lead to discordant measurements between FF and FFPE samples, and this effect can vary by gene or by probe location. Nanostring nCounter platform for gene expression analysis has shown flexibility and reproducibility with low quality RNA from FFPE tissue samples (Veldman-Jones, et al., 2015). Guinney et al. (2015) presented another classifier intended for use with single samples (single sample predictor, SSP), but this classifier is also primarily trained and validated on fresh frozen samples, and involves 693 genes, more than one would ideally want to use in a clinical assay.

II. Summary of FFPE-Based Classifier Development

Summary of CMS Classifier: A CMS classifier has been developed that can be applied to FF or FFPE samples and obtains accurate CMS classifications for individual patient samples. This assay utilizes custom Nanostring code sets that have a strong FF/FFPE correlation such that they are appropriate for use with each sample type. This algorithm can also successfully classify FF samples using other gene expression platforms, including Affymetrix arrays and RNAseq, and the ideas can be applied to other platforms including HTG and any others that emerge. As detailed below, extensive studies have been performed to validate this classifier, first in the FF setting for Affymetrix or RNAseq data, and then in the FFPE and FF setting using Nanostring code sets.

Development and validation of 472-gene FF-based classifier: A rigorous study was performed to identify a parsimonious, robust, and reliable CMS classifier primarily for fresh frozen (FF) samples using training and validation data from the colorectal subtyping consortium (CRCSC) used in Guinney et al. (2015). The model was trained using a data set consisting of 1,329 samples from 12 studies, and validated in a cohort of 1,329 samples from 14 studies that included subsets to test out-of-sample predictive accuracy (383 samples from two studies), RNAseq accuracy (189 samples from one data set), and Affymetrix accuracy (713 samples from 11 studies). The CMS signal was remarkably consistent across these two data sets (FIG. 1). In these validation data, a 472-gene classifier was found to have 96.3% 4-class accuracy in the validation data set, with similar levels of accuracy in the Affymetrix, RNAseq, and out-of-sample subsets. This classifier gives a probability for each CMS, with the CMS with the highest probability chosen, and the probability for the chosen CMS being called the classification confidence. A vast majority (75%-80%) of samples were classified with high confidence (>90%), and these were nearly always classified correctly, with 1,076/1,078 (99.8%) of the samples in the validation data correctly classified, and many of the "incorrectly" classified samples with lower degrees of confidence in fact appeared to have evidence of being a mixture of CMS (which is expected in 15%-20% of samples according to Guinney et al. (2015)), and in those cases, the gold standard CMS was nearly always among those with substantial probabilities.

Development and validation of 100-gene FFPE-based classifier: Next, a custom Nanostring code sets was designed based on the list of 472 genes from this classifier. These code sets were run on 85 paired FF/FFPE samples that were part of the CRCSC data set and so had gold standard CMS calls, and 73 others for which Affymetrix FF samples were also run to get pseudo-gold standard CMS calls. Rather than building a de novo classifier from this relatively small study with 158 samples, a strategy was used to select a subset of 100 genes having concordant signals in paired FF and FFPE measurements, and then the CMS classifier was retrained using the 1,329 samples in the CRCSC training data set and these 100 genes, using sample-specific quantile normalization to deal with the single-sample setting, and then applying this classifier to the Nanostring data. A subset of 100 genes/probe sets (see Table 1) with high Spearman correlation across paired FF/FFPE values (median=0.730) demonstrated that this correlation is consistently high across batches and thus a characteristic of the gene and probe set, and this set of genes was used to define the classifier. This classifier demonstrated 80% 4-class accuracy for FFPE samples, with this accuracy increasing to 86% and 89% for samples classified with high levels of confidence (80% and 90% confidence respectively). This performance was robust to measures of RNA quality.

TABLE 1

200-gene FFPE-based classifier. One asterisk next to the Gene Name indicates inclusion in the 100-gene FFPE-based classifier and two asterisks indicates inclusion in the 75-gene FFPE-based classifier.

| Gene Name | Accession | Position | Target Sequence |
|---|---|---|---|
| ABAT** | NM_000663.4 | 5004-5103 | TTAGCTAGAAGAATTTCAAGGAAAAGAAT TCTCAGCAGAGCTCAAGATTGTAGAAACT CAGCAGAAGCTGGTAAAAACATGGGGAGC |

TABLE 1-continued 200-gene FFPE-based classifier. One asterisk next to the Gene Name
indicates inclusion in the 100-gene FFPE-based classifier and two
asterisks indicates inclusion in the 75-gene FFPE-based classifier.

| Gene Name | Accession | Position | Target Sequence |
|---|---|---|---|
| | | | CCGGAGGACAGGC<br>(SEQ ID NO: 1) |
| ACE2** | NM_021804.2 | 2958-3057 | AGTTGAAAACAAGGATATATCATTGGAGC<br>AAGTGTTGGATCTTGTATGGAATATGGAT<br>GGATCACTTGTAAGGACAGTGCCTGGGAA<br>CTGGTGTAGCTGC<br>(SEQ ID NO: 2) |
| ACSL5 | NM_203379.1 | 2110-2209 | CCAACATTGAAAGCAAAGCGAGGAGAGCT<br>TTCCAAATACTTTCGGACCCAAATTGACA<br>GCCTGTATGAGCACATCCAGGATTAGGAT<br>AAGGTACTTAAGT<br>(SEQ ID NO: 3) |
| ADGRG6** | NM_001032394.2 | 6230-6329 | AACCAGATGAGAAAAAAATTAAGAAATTG<br>CTCAAGGGAAACATTTGTAAATGGATTTG<br>AAAGATTGAGCCAAATTCTGTTGTCAGTT<br>CTAAGCATGCAGT<br>(SEQ ID NO: 4) |
| AGR2** | XM_005249581.3 | 1213-1312 | TAAATTTTAGTCAGATTTTGCCCAACCTA<br>ATGCTCTCAGGGAAAGCCTCTGGCAAGTA<br>GCTTTCTCCTTCAGAGGTCTAATTTAGTA<br>GAAAGGTCATCCA<br>(SEQ ID NO: 5) |
| AHNAK2 | NM_138420.2 | 17559-17658 | TAAAGGCTACACACACATATGGAGCACCC<br>CATCCCACAGCACATTACATCCACCTCAC<br>TTCACAGAACGGAGAACAGAGCAGAAATG<br>ACCAGAACACCTT<br>(SEQ ID NO: 6) |
| AMACR** | 236365_at.1 | 68-167 | ATACTTGCTGGGGATACCATAATGAACAA<br>AACAGACCTGTTCTCCGCTCTTGAGGAAA<br>TCAAAGACAAACACAGGATATGGAATAAA<br>CCCAGAATTATCT<br>(SEQ ID NO: 7) |
| ANKRD27 | NM_032139.2 | 4001-4100 | GAAACATCCCTTTTTGTTGAGAACCTCCC<br>TTGAATGTCTGTCACACTCACACCTGACG<br>GGATGGTTACTGGATTAGAGAGTAGATTT<br>GGCACATCTTTTC<br>(SEQ ID NO: 8) |
| ANP32B* | NM_006401.2 | 1297-1396 | ACCAAGCTTGTGGACTTCACCCCAACAAA<br>ATTGTAAGCGTTGTTAGGTTTTTGTGTAA<br>GATTCTTGCTGTAGCGTGGATAGCTGTGA<br>TTGGTGAGTCAAC<br>(SEQ ID NO: 9) |
| APOL1 | NM_001136540.1 | 2465-2564 | TGAAGTCTTTCCCTGGTGATGGTCCCCTG<br>CCCTGTCTTTCCAGCATCCACTCTCCCTT<br>GTCCTCCTGGGGGCATATCTCAGTCAGGC<br>AGCGGCTTCCTGA<br>(SEQ ID NO: 10) |
| ARHGAP10 | NM_024605.3 | 2733-2832 | AGCACCTGCTGCTGCGATTTTAAAGGGAA<br>CTGTACTACTCGCAGTGATAGGTTTGCAG<br>AGTGTGTGCTTGGCTGTGGCAGCCTAGCT<br>TGGAGAAGCTGCT<br>(SEQ ID NO: 11) |
| ARHGAP32 | XM_011543075.1 | 6479-6578 | GTTCCTAAACCAGAGTACGAGGTCCCTGG<br>GAATTTAAGTAGCTACGCATTATCTATTA<br>TTAGACTGCAAGTTCCTGCAATAACTGCT<br>TAGTTCACAGCCC<br>(SEQ ID NO: 12) |
| ARID3A* | NM_005224.2 | 2401-2500 | GGCGTTCAGGCAGCCCTGATGGACCGAAG<br>GCTCTGGTGTCTGGTTTGGCCCCACAGCA<br>GTGTGGGCCGATCCTGTTTACCTCATACA<br>TCCCTGCACTGTG<br>(SEQ ID NO: 13) |

TABLE 1-continued 200-gene FFPE-based classifier. One asterisk next to the Gene Name
indicates inclusion in the 100-gene FFPE-based classifier and two
asterisks indicates inclusion in the 75-gene FFPE-based classifier.

| Gene Name | Accession | Position | Target Sequence |
|---|---|---|---|
| ASCL2** | NM_005170.2 | 1471-1570 | CGGGGGGCACCAACACTTGGAGATTTTTC CGGAGGGGAGAGGATTTTCTAAGGGCACA GAGAATCCATTTTCTACACATTAACTTGA GCTGCTGGAGGGA (SEQ ID NO: 14) |
| ASF1B** | NM_018154.2 | 1134-1233 | GTCAGTGCCTGTCAAGGCTCCAGTCCTGC TGAGCCAAAGGCTTTGTCATTCCTTTCTC TTCCTGTACATCTGAGCAGACCCACTCCA GCTTTCTGGTGTC (SEQ ID NO: 15) |
| ASPH** | NM_001164751.1 | 1918-2017 | GCCTTTGGCTAATTGAGTAATTCCCCTCC AGCACTAGAGACCGCTCAGTGCTCTTACT AGATGAACTCAGTAACGCCTTGAGCTGGG TTGATTGAGGATG (SEQ ID NO: 16) |
| ASRGL1* | NM_025080.3 | 1141-1240 | CAGCCGCCAAGGACGGCAAGCTGCACTTC GGAATTGATCCTGACGATACTACTATCAC CGACCTTCCCTAAGCCGCTGGAAGATTGT ATTCCAGATGCTA (SEQ ID NO: 17) |
| ATP1OB | NM_025153.2 | 7038-7137 | ACCTGCAAGTTGATTAGAACTGCCTTTCT TCCCAGGCTTGACATAGGTATTAAGTCAA AATTACATGAAACCCAGTGGTAAAAAAGC CTCTGAAAGCTGT (SEQ ID NO: 18) |
| ATP9A** | NM_006045.2 | 7093-7192 | AAATTTGGTTTTGAATGAACCTGCAAAGC ATCCTGCAGCGTGAGCAGCTCCTCCACCT GGAGCTCCGAAGCATCTTCTCAGGCCAAA GCGGCATTACCCG (SEQ ID NO: 19) |
| AXIN2** | NM_004655.3 | 3902-4001 | ATATAGTGTACGGCAAAAGAGTATTAATC CACTATCTCTAGTGCTTGACTTTAAATCA GTACAGTACCTGTACCTGCACGGTCACCC GCTCCGTGTGTCG (SEQ ID NO: 20) |
| BCL2L15* | NM_001010922.2 | 3364-3463 | TATTTTAAGAGACTCTATCTTAGGAGAGC TTAAGTGATTGGGCTGCAGGAAGAAGACA TTGTAACCCAGGAATTAAAAATGGATTCA GATTGCCTGATTT (SEQ ID NO: 21) |
| BCL6 | NM_001130845.1 | 3109-3208 | ATTAAAAATATAAAACTGCGTTAAAGGCT CGATTTTGTATCTGCAGGCAGACACGGAT CTGAGAATCTTTATTGAGAAAGAGCACTT AAGAGAATATTTT (SEQ ID NO: 22) |
| BST2** | NM_004335.2 | 561-660 | GAAGCTGGCACATCTTGGAAGGTCCGTCC TGCTCGGCTTTTCGCTTGAACATTCCCTT GATCTCATCAGTTCTGAGCGGGTCATGGG GCAACACGGTTAG (SEQ ID NO: 23) |
| C20orf196 | NM_152504.2 | 987-1086 | TCTCTGAGGAGTAATTTATGCTCTAGCAC TCCCTTTCCTCTAGATCGGCCTGAGGCTG GGACATTACATGAAATCACACCCTTGCTG GGCTTAATCCCTT (SEQ ID NO: 24) |
| C3orf14** | NM_001291942.1 | 271-370 | AGGATATAGAAGCAGCAGAAAAGTCACTA CAGACCAGGATTCACCCACTTCCACGGCC TGAGGTGGTTTCTCTTGAGACTCGTTACT GGGCATCAGTAGA (SEQ ID NO: 25) |

TABLE 1-continued 200-gene FFPE-based classifier. One asterisk next to the Gene Name
indicates inclusion in the 100-gene FFPE-based classifier and two
asterisks indicates inclusion in the 75-gene FFPE-based classifier.

| Gene Name | Accession | Position | Target Sequence |
|---|---|---|---|
| CA8 | NM_004056.4 | 662-761 | GGAGCTCCATCTGATCCACTGGAACTCCA CTCTGTTTGGCAGCATTGATGAGGCTGTG GGGAAGCCGCACGGAATCGCCATCATTGC TCTGTTTGTTCAG (SEQ ID NO: 26) |
| CAB39L** | NM_001287339.1 | 1087-1186 | AACTCATTGAGTTTCTGAGCAGCTTCCAA AAAGAAAGGACGGATGATGAGCAGTTCGC TGACGAGAAGAACTACTTGATTAAACAGA TCCGAGACTTGAA (SEQ ID NO: 27) |
| CACNA1D | NM_000720.3 | 7282-7381 | AGTTTACATAAGAGAATATCACTCCGATG GTCGGTTTCTGACTGTCACGCTAAGGGCA ACTGTAAACTGGAATAATAATGCACTCGC AACCAGGTAAACT (SEQ ID NO: 28) |
| CCDC109B* | NM_017918.4 | 741-840 | CCCTTGAACAGGTGAAAGCTGGAATAGAA GCTCATTCGGAAGCCAAAACCAGTGGACT CCTGTGGGCTGGATTGGCACTGCTGTCCA TTCAGGGTGGGGC (SEQ ID NO: 29) |
| CCNO | NM_021147.4 | 1122-1221 | GAGGCGGCGCTGGAGGACTGTATGGGCAA GTTGCAGCTGCTGGTGGCCATAAACAGTA CTTCCTTGACTCACATGCTGCCCGTTCAG ATCTGCGAGAAGT (SEQ ID NO: 30) |
| CDC42EP2 | NM_006779.3 | 1779-1878 | AGGGCTTTGTGGAGGACAGGCCTTGCCCT CAAGAACGTCGTACCTGACGCTGAGCCTG TCATGAGAATGCAACAGGAGCAAACCAAG TGTTGCTGTGACA (SEQ ID NO: 31) |
| CDC42EP5 | NM_145057.2 | 775-874 | AGCTGAACGACGTCATCGGCCTCTAGGTT CCCTCATTCCCCGCGCCCTTCCCGCCCGG CACCCCACTTCTGTATACATAAACGGCCA AGGTGTGTGCCCG (SEQ ID NO: 32) |
| CDCA2** | XM_011544419.1 | 2904-3003 | TAAAGATTTGTCTGATGCCATTGAGCAAA CCTTTCAGAGGAGAAATAGTGAAACCAAA GTGCGACGTAGCACGAGGCTACAGAAGGA TTTAGAAAACGAA (SEQ ID NO: 33) |
| CDCA7* | NM_031942.4 | 2093-2192 | TTCTTCTGCCCGAAGGGTAAGTGGTGCGT CCAGCTTACACAATCATAATTCAAAGGTT GGTGGGCAATGTAATACTTAATTAAAATA ATGATGGAAGAGC (SEQ ID NO: 34) |
| CDHR1** | NM_033100.3 | 4941-5040 | CAGGAATTGGGAGGCCTAGGGTGGGCATG AAAGCTTGGGAAGCACTGTCGTCTCTCAG ACAGGCGTCCTAAAGACCTCTAGGCTGGA AGCTTGGGCTTGC (SEQ ID NO: 35) |
| CEBPA | NM_004364.4 | 2055-2154 | CTCAGCCTTGTTTGTACTGTATGCCTTCA GCATTGCCTAGGAACACGAAGCACGATCA GTCCATCCCAGAGGGACCGGAGTTATGAC AAGCTTTCCAAAT (SEQ ID NO: 36) |
| CEL** | NM_001807.4 | 2236-2335 | CCCCACAGATGACTCCAAGGAAGCTCAGA TGCCTGCAGTCATTAGGTTTTAGCGTCCC ATGAGCCTTGGTATCAAGAGGCCACAAGA GTGGGACCCCAGG (SEQ ID NO: 37) |

TABLE 1-continued 200-gene FFPE-based classifier. One asterisk next to the Gene Name
indicates inclusion in the 100-gene FFPE-based classifier and two
asterisks indicates inclusion in the 75-gene FFPE-based classifier.

| Gene Name | Accession | Position | Target Sequence |
|---|---|---|---|
| CENPE* | NM_001813.2 | 8080-8179 | TCAAGTTTAGGCCTTTGTCCAGAGGTGCA AAATGCAGGAGCAGAGAGTGTGGATTCTC AGCCAGGTCCTTGGCACGCCTCCTCAGGC AAGGATGTGCCTG (SEQ ID NO: 38) |
| CEP192 | NM_032142.3 | 7347-7446 | GAGGCTTCTGCTCGCATACCTGAGCAGCT TGATGTGACTGCTCGTGGAGTTTATGCCC CAGAGGATGTGTACAGGTTCCGGCCGACT AGTGTGGGGGAAT (SEQ ID NO: 39) |
| CHN2 | NM_001293081.1 | 2191-2290 | ACTCACCAGTCTTGCTTTGGAGTGAGCAG AAGAGAATGACTATTTTACGTGGAGCATC ATTGTGTGACTGTTGACCTGGACAGTCCC AAGGGCTATGCAG (SEQ ID NO: 40) |
| CKAP2 | NM_001098525.2 | 2785-2884 | CCCAGACTTGTGTTCTCTTGCGTCCCTTG GACTGCCTGTTGATTGATGGAAAGTGTCT GCACTGACACTTTTCGTCAGTAGTCTGTA GTTTCGTGGCCTC (SEQ ID NO: 41) |
| CPNE1** | NM_001198863.1 | 1426-1525 | TGACGGATGTGGAAGCCACACGTGAGGCT GTGGTGCGTGCCTCGAACCTGCCCATGTC AGTGATCATTGTGGGTGTGGGTGGTGCTG ACTTTGAGGCCAT (SEQ ID NO: 42) |
| CREB3L1* | NM_052854.2 | 2554-2653 | CCCCTGCTGCTGCCCAAGCCGCTGGGCCT TTTTAATTGCCAAACTGCTCTCTTCATCA GCTCAGCACATGCTTTAAGAAAGCAAAAC CAAAAAAAAAAAA (SEQ ID NO: 43) |
| CRYM | NM_001014444.2 | 833-932 | CTGAGCTGGGAGAAGTGATTAAGGGAGTG AAACCAGCCCACTGTGAGAAGACCACCGT GTTCAAGTCTTTGGGAATGGCAGTGGAAG ACACAGTTGCAGC (SEQ ID NO: 44) |
| CSGALNACT2 | NM_018590.4 | 3013-3112 | GGAGAGAAAAAGCAAATGGTATGCCACAA GATCACTCTGATTTGAGAAAAGGGAGGAG GGGAAGATAGTCTGAATGGAAATCTGAAA TACGGAATGTTTT (SEQ ID NO: 45) |
| CTSE | NM_001910.2 | 2071-2170 | TTTGTGGCAAAAATACTTCCTAGGTGGTG CTGGGTACTTCTTGTTGCATCCTGTCAGG AGGCAGATAATGCTGGTGCCTCTCTATTG GTAATGTTAAGAC (SEQ ID NO: 46) |
| CTTNBP2** | NM_033427.2 | 5010-5109 | GAAATCAACAACAACTCAAAAGAAGTGAA TTGGAACTTACACAAAAATGAACACCTAG AAAAACCTAACAAATAGGCCTGCCTACAA TATTCTCATTATT (SEQ ID NO: 47) |
| CYTH3 | NM_004227.3 | 3967-4066 | TGCTGGCCGCCCTGGTTCATATTTGAGTT TAATTGTACTGACCCTGGACCCAGATAAG CAGCAACTTTGTGTCTTTGGGGTCACAGA ACATTTTGGGGCA (SEQ ID NO: 48) |
| DACH1** | NM_080759.4 | 4909-5008 | AATGTCTAGTTGTTCTATATTATAACCAC ATTTGCGCTCTATGCAAGCCCTTGGAACA GAACATACTCATCTTCATGTAGGACCTAT GAAAATTGTCTAT (SEQ ID NO: 49) |

TABLE 1-continued 200-gene FFPE-based classifier. One asterisk next to the Gene Name
indicates inclusion in the 100-gene FFPE-based classifier and two
asterisks indicates inclusion in the 75-gene FFPE-based classifier.

| Gene Name | Accession | Position | Target Sequence |
|---|---|---|---|
| DACT1 | NM_001079520.1 | 3351-3450 | AGAGACATTCACTATTAATGAAGTAACCC TTGGGCATGACTCCAATCCCAGAATTGCT CACTGAGCGCTATGCCACCGAAGCGTTGA CCTGAACATATTA (SEQ ID NO: 50) |
| DAPK2 | NM_014326.3 | 1364-1463 | AATTCTCCATAAAATGGGCTTTCCTCTGT CTGCCATCCTCAGAGTCTGGGGTGGGAGT GTGGACTTAGGAAAACAATATAAAGGACA TCCTCATCATCAC (SEQ ID NO: 51) |
| DEPDC1** | NM_001114120.2 | 3455-3554 | TTAATCAAGGGAGATACACCTATCAGATG TTTAAAATAACAACACTACCCACTGAAAT CAGGGCATATAGAATCATTCAGCTAAAGA GTGACTTCTATGA (SEQ ID NO: 52) |
| DIDO1** | NM_022105.4 | 2238-2337 | AAGTATTCGTATTCTCTTCATCCCAGTCT GATTGCATAGCCACACTGCCCGGCACGCC ACATCCACCCCTGTCTGCACATGAGTTGT TCTGACAACAGCG (SEQ ID NO: 53) |
| DOCK5** | NM_024940.6 | 6148-6247 | GCTGTGCTTGAGACTTAGGTACTTTTCTC ACGTGGACACACTGATCCCATCCCATATT GCATCTTGGAAGAGATGGATATCAAGTAC ACTTTGGTAGCTG (SEQ ID NO: 54) |
| DPEP1** | NM_001128141.2 | 1033-1132 | AGGCCAACCTGTCCCAAGTGGCCGACCAT CTGGATCACATCAAGGAGGTGGCAGGAGC CAGAGCCGTGGGTTTTGGTGGGGACTTTG ATGGTGTTCCAAG (SEQ ID NO: 55) |
| DPM1* | NM_003859.1 | 461-560 | TATATGGCTGGGATTTGAAAAGAAAAATA ATCAGCCGTGGGGCCAATTTTTTAACTCA GATCTTGCTGAGACCAGGAGCATCTGATT TAACAGGAAGTTT (SEQ ID NO: 56) |
| EIF6** | NM_181466.2 | 435-534 | GCTCAAGGTGGAAGTCTTCAGACAGACAG TGGCCGACCAGGTGCTAGTAGGAAGCTAC TGTGTCTTCAGCAATCAGGGAGGGCTGGT GCATCCCAAGACT (SEQ ID NO: 57) |
| ENO2** | NM_001975.2 | 1855-1954 | GGTTGGTGTGCTGAGGTGTTAGAGAGGGA CCATGTGTCACTTGTGCTTTGCTCTTGTC CCACGTGTCTTCCACTTTGCATATGAGCC GTGAACTGTGCAT (SEQ ID NO: 58) |
| EPB41L4B | NM_018424.3 | 3340-3439 | TTTTTGGCTACTGCAAAAATCTATTCAGC AAGAAGGTATCAGCTGCATACCTTGCACA GTGGAGCTGACTACCTATAAACTCTCCCT AAGGCATTTGTTT (SEQ ID NO: 59) |
| EREG** | NM_001432.2 | 3627-3726 | TGAGAACCAAAGCAACCACAAATGCATAA ATGCATAATTTATGGTCTTCAACCAAGGC CACATAATAACCCAGTTAACTTACTCTTT AACCAGGAATATT (SEQ ID NO: 60) |
| ERRFI1 | NM_018948.3 | 2758-2857 | GTGGCTGCTTCACTTAGATGCAGTGAGAC ACATAGTTGGTGTTCCGATTTTCACATCC TTCCATGTATTTATCTTGAAGAGATAAGC ACAGAAGAGAAGG (SEQ ID NO: 61) |

TABLE 1-continued 200-gene FFPE-based classifier. One asterisk next to the Gene Name
indicates inclusion in the 100-gene FFPE-based classifier and two
asterisks indicates inclusion in the 75-gene FFPE-based classifier.

| Gene Name | Accession | Position | Target Sequence |
|---|---|---|---|
| ESRP1 | XM_005250992.2 | 3370-3469 | TACTTTAACACCTTAAAGGGAGAAGCAAA CATTTCCTTCTTCAGCTGACTGGCAATGG CCCTTTAACTGCAATAGGAAG AAAGGTTTGTGTG (SEQ ID NO: 62) |
| FABP5* | NM_001444.1 | 101-200 | GCTTTGATGAATACATGAAGGAGCTAGGA GTGGGAATAGCTTTGCGAAAAATGGGCGC AATGGCCAAGCCAGATTGTATCATCACTT GTGATGGTAAAAA (SEQ ID NO: 63) |
| FAM105A** | NM_019018.2 | 1352-1451 | TTTTCAGTGATTTCCTCTGAAGCAGCTGC ACTGATACATTTGGGAGTTGGTGGCTTGA CTTTGTCCATAAGGGGCGTGGCCACTTCA CATGATGGCGGGC (SEQ ID NO: 64) |
| FAM122B** | NM_001166599.2 | 3776-3875 | AAATTCAATGGTGGGATAGAATTAGGTCA GGAAATGGAAGTTGTTCCAATGGTGTGAG AACTAGGAGACAAGATGATTCACTTTATT ATTTAAACCAAGC (SEQ ID NO: 65) |
| FAM3D** | NM_138805.2 | 773-872 | GGAAACTCTTCTCTGACTTGGGGAGTTCC TACGCAAAACAACTGGGCTTCCGGGACAG CTGGGTCTTCATAGGAGCCAAAGACCTCA GGGGTAAAAGCCC (SEQ ID NO: 66) |
| FAM84A | NM_145175.2 | 3017-3116 | ACAGCTGTGATTTTGTTGGACAGCAAGTA TTATGGCCAAAGCCAGTTTCTTGGCATTT CAAAAATAATGCAATAAAAACTAGTTGAG GTTAGCTGAGGCT (SEQ ID NO: 67) |
| FARP1* | 227996_at.1 | 67-166 | TCTCTGTTGCCGGATGCTGTCTAGGGCCT GTTAGTTGCTATTTCCTTGCCTCCGCTCC CCTTCCCACTAGCCTTCTAACTACCTTTT ATTCTCGGCTCCA (SEQ ID NO: 68) |
| FBXO34** | NM_152231.1 | 2732-2831 | AAAAAGAAAAGTCAGGCACCCCACCTTAG ACCTCGTATGCTTGATCCTGTGAGATTGA TGTTTGTGGCTGGAGGTGGATTTCATGCC CTGTGGTGTTTAC (SEQ ID NO: 69) |
| FITM2** | 226805_at.1 | 135-234 | TTCATCGTCTGTCAGGTGGAGATGAAGAG AAATGGTGCATGTAAAGTGCTCAGCATCT GTGCTTAGCAGGCCATAGTCTCCCTGCCT CCTTTTTCTTGAG (SEQ ID NO: 70) |
| FOXA2** | NM_021784.4 | 1775-1874 | CCACACAGATACCCCACGTTCTATATAAG GAGGAAAACGGGAAAGAATATAAAGTTAA AAAAAAGCCTCCGGTTTCCACTACTGTGT AGACTCCTGCTTC (SEQ ID NO: 71) |
| FRZB | NM_001463.2 | 1813-1912 | AAATAGGAGCTTAAGAAAGAACATTTTGC CTGATTGAGAAGCACAACTGAAACCAGTA GCCGCTGGGGTGTTAATGGTAGCATTCTT CTTTTGGCAATAC (SEQ ID NO: 72) |
| FUT8** | NM_004480.4 | 3411-3510 | TGAGAAGATCGGAACAGCTCCTTACTCTG AGGAAGTTGATTCTTATTTGATGGTGGTA TTGTGACCACTGAATTCACTCCAGTCAAC AGATTCAGAATGA (SEQ ID NO: 73) |

TABLE 1-continued 200-gene FFPE-based classifier. One asterisk next to the Gene Name
indicates inclusion in the 100-gene FFPE-based classifier and two
asterisks indicates inclusion in the 75-gene FFPE-based classifier.

| Gene Name | Accession | Position | Target Sequence |
|---|---|---|---|
| GALNT5** | 236129_at.1 | 278-377 | AGCTGTCACGTTTGTGAAATCCCTCCAGA CTACATGCATGCTTACCTAACAGTTTGAA ATAGTATTGATCTACTGCTGGTAACCCTG CTTGATGGCAGCA (SEQ ID NO: 74) |
| GALNT8* | NM_017417.1 | 1537-1636 | AAAATGTTTATCCACTCTTGAAGCCACTC CACACCATCGTGGGCTATGGAAGAATGAA AAACCTATTGGATGAAAATGTCTGCTTGG ATCAGGGACCCGT (SEQ ID NO: 75) |
| GFPT1** | NM_001244710.1 | 2615-2714 | TGGTACTTGTTTCACCATACTTCATTCAG ACCAGTGAAAGAGTAGTGCATTTAATTGG AGTATCTAAAGCCAGTGGCAGTGTATGCT CATACTTGGACAG (SEQ ID NO: 76) |
| GGH | NM_003878.2 | 974-1073 | ATGGAAGGATATAAGTATCCAGTATATGG TGTCCAGTGGCATCCAGAGAAAGCACCTT ATGAGTGGAAGAATTTGGATGGCATTTCC CATGCACCTAATG (SEQ ID NO: 77) |
| GNG4** | NM_001098721.1 | 4475-4574 | GGTGTATACCCTACAGAAATGTGTACATG TGTTCATCCAGAGACATGCTCTAAATCTT CACAAAAACACTCTCCATAATAACCCCGA ACAGGAAAGCACC (SEQ ID NO: 78) |
| GPCPD1 | NM_019593.3 | 2731-2830 | ACATGGGTTGACATGCACACAACACCATT TTCATTCAGTATGAACCTTGAGGCTGCTG CCATTTTTCCACTTAACCAAACCAGCCTG AAGGTGAACCTCG (SEQ ID NO: 79) |
| GPR143** | NM_000273.2 | 1285-1384 | AATTGAAATTCACACTGCAAGTGAATCCT GCAACAAAAATGAGGGTGACCCTGCTCTC CCAACCCATGGAGACCTATGAAGGGGATG TGCTGGGGGTCCA (SEQ ID NO: 80) |
| GPR153** | NM_207370.2 | 3781-3880 | GGGGTTTTGCTCTGTGTGTTTCATATCCA ACGGCAATACTTGCAGGGGGACAGAGTCC TCTAAATACTCCAATCCTGCGGTTTTTAC AAACATAAAGGGG (SEQ ID NO: 81) |
| GRM8** | NM_000845.2 | 2886-2985 | GTGGTGACAGCTGCCACCATGCAAAGCAA ACTGATCCAAAAAGGAAATGACAGACCAA ATGGCGAGGTGAAAAGTGAACTCTGTGAG AGTCTTGAAACCA (SEQ ID NO: 82) |
| GTF2A2 | NM_004492.1 | 246-345 | AGTTCTACTTCAGTTTGATAAGGCTATAA ATGCAGCACTGGCTCAGAGGGTCAGGAAC AGAGTCAATTTCAGGGGCTCTCTAAATAC GTACAGATTCTGC (SEQ ID NO: 83) |
| GUCY2C | NM_004963.3 | 3250-3349 | AGGCAGCAGGGATAAGAAGCCAAAAACCC AGACGGGTAGCCAGCTATAAAAAAAGGCAC TCTGGAATACTTGCAGCTGAATACCACAG ACAAGGAGAGCAC (SEQ ID NO: 84) |
| GYG2 | NM_001184704.1 | 2141-2240 | CTCTTGGCTTGGTCTCTACCCTCACTACC TCAGTTCTCAATAACTTAGTGAATCACTG CCCTCCTCAAAGCCATTTCCACTCAGCTC TTTCCAGAGAATT (SEQ ID NO: 85) |

TABLE 1-continued 200-gene FFPE-based classifier. One asterisk next to the Gene Name
indicates inclusion in the 100-gene FFPE-based classifier and two
asterisks indicates inclusion in the 75-gene FFPE-based classifier.

| Gene Name | Accession | Position | Target Sequence |
|---|---|---|---|
| HEPH** | NM_001130860.3 | 4041-4140 | GTATCCTTCTCACAAAGTAGAGACCAAGA GAAAAACTCATTGATTGGGTTTCTACTTC TTTCAAGGACTCAGGAAATTTCACTTTGA ACTGAGGCCAAGT (SEQ ID NO: 86) |
| HES2** | NMO19089.4 | 3878-3977 | TCCACGTGAGTGAGGATAAAGACTGGGCT GCCAAGGAGGACTCCTCATAAACATTGAC AAATTGCTCTGCCCCGCCTGTGATCCCAG ACGACTCCTGCAG (SEQ ID NO: 87) |
| HLA-E | NM_005516.5 | 2124-2223 | ACTGGTGGCTTTATAAGAAGAGGAAAAGA GAACTGAGCTAGCATGCCCAGCCCACAGA GAGCCTCCACTAGAGTGATGCTAAGTGGA AATGTGAGGTGCA (SEQ ID NO: 88) |
| HLX | NM_021958.3 | 1721-1820 | GGGAGTGGTGGGAGCAGCGGCGGCGGCGG CAATAGTTTCAGCTTCAGCAGCGCCAGCA GTCTTAGTAGCAGCAGCACCAGTGCGGGT TGCGCCAGCAGCC (SEQ ID NO: 89) |
| HOXD11 | NM_021192.2 | 1069-1168 | ACCAGCCTGCTCTCCGCAGGCCCACTGTC CTTGGGTTTAATGACGTCTCTTCTCTGTG GAACTTCACGATTCCTTCCCACGGTCAAC TCGGGACCTCCCA (SEQ ID NO: 90) |
| HSPA4L** | NM_014278.2 | 2745-2844 | AATCCTCTGGAGAGATGGAAGTGGACTAA GTCTTAATTTTACCTTCACATTAATTCAA ACCGTGCAAGTAACCACGGGGTCCATCTT TTACATCTGGTAC (SEQ ID NO: 91) |
| HSPA6 | NM_002155.3 | 2019-2118 | GACAGAGTGGCTGCCAAAAACTCGCTGGA GGCCCATGTCTTCCATGTGAAAGGTTCTT TGCAAGAGGAAAGCCTTAGGGACAAGATT CCCGAAGAGGACA (SEQ ID NO: 92) |
| HUNK** | NM_014586.1 | 4727-4826 | GCAGGGTGTATACCTGCGCATTGGGAACT TGCTGGAACCCCTGATGCATTTTCCTTGA GAGCAGGGGTACTTCCGCCTTGCCGTTAG CTTGTGGAGAACG (SEQ ID NO: 93) |
| IFIT3 | NM_001031683.2 | 2136-2235 | TGGTAGCAATAAATGCTTCAGGCCCACAT GATGCTGATTAGTTCTCAGTTTTCATTCA GTTCACAATATAACCACCATTCCTGCCCT CCCTGCCAAGGGT (SEQ ID NO: 94) |
| ILDR1 | NM_001199800.1 | 2106-2205 | TGCATATTTATATAATCTCTGACTTGTAA TGGACCCTGACTGGAATGTGATCCCTCAG GAACTTAGTAGCCTGAGTCTTTCAGTAGA CTACACTGCCCAG (SEQ ID NO: 95) |
| IMMP2L | NM_032549.3 | 985-1084 | CCTGAGTTGCTGGCATTGGGAGGCCAGTT ACTGGAAAGGAATGGAAAAAAGAAGCCTC CAAAAGGGAAAAACTTCTGACAATATGAT GCTGTGCGAGAAA (SEQ ID NO: 96) |
| JADE3 | NM_014735.3 | 4564-4663 | GTAGCCTTTGTCCCTTCATGCCTTTCAAT TCTGAGTGGGAGGAAAAGCAAACATCAAA ACAGTGCTTCAGCCAAATTCCATATGTAA TGCCATTGGGAGA (SEQ ID NO: 97) |

TABLE 1-continued 200-gene FFPE-based classifier. One asterisk next to the Gene Name
indicates inclusion in the 100-gene FFPE-based classifier and two
asterisks indicates inclusion in the 75-gene FFPE-based classifier.

| Gene Name | Accession | Position | Target Sequence |
|---|---|---|---|
| KCNK1 | NM_002245.3 | 1119-1218 | AAATGAGCCTTTTGTGGCCACCCAGTCAT CTGCCTGCGTGGATGGCCCTGCAAACCAT TGAGCGTAGGATTTGTTGCATTATGCTAG AGCACCAGGGTCA (SEQ ID NO: 98) |
| KCTD1 | NM_001258222.1 | 1095-1194 | CAGCCGCAGTTGGTGCTGTGATGGCCGTG AAGTGTCCTGGGCCTCCCGAGGCCTCTGA CAAATAAACAAGCCATGAGTGGTGAGGAC ACAGTCTCCTTAC (SEQ ID NO: 99) |
| KIF2C | NM_006845.3 | 2634-2733 | GGGTTGTCCTGGCTCTGGGGAGAGAGACG GAGCCTTTAGTACAGCTATCTGCTGGCTC TAAACCTTCTACGCCTTTGGGCCGAGCAC TGAATGTCTTGTA (SEQ ID NO: 100) |
| KLK1 | NM_002257.3 | 498-597 | TTTGGCTTCCGGCTGGGGCAGCATCGAAC CAGAGAATTTCTCATTTCCAGATGATCTC CAGTGTGTGGACCTCAAAATCCTGCCTAA TGATGAGTGCAAA (SEQ ID NO: 101) |
| LDLRAD3 | NM_001304263.1 | 3026-3125 | AGCCAGAATGTGTTAGAACTCTGGCTGAA CATTTCATCTCCTGTGAGTCAGAAGGGCT TTATTTCTCCCTTTGATGGGGCCCCTTCT TCTTTCTGGTGCT (SEQ ID NO: 102) |
| LEFTY1** | NM_020997.3 | 1181-1280 | GGCGCCTAGTGTAGCCATCGAGGGACTTG ACTTGTGTGTGTTTCTGAAGTGTTCGAGG GTACCAGGAGAGCTGGCGATGACTGAACT GCTGATGGACAAA (SEQ ID NO:103) |
| LMO4 | NM_006769.3 | 1438-1537 | TTGGTGTATTAAAATGACTGAATATGAAC ATTAAGGACTCCATGAACCTGGGCTAATG GGAGACTGTAGAGAAAATGAAAAAAGATC CACCAGAGGACAT (SEQ ID NO: 104) |
| LNX2*[1] | XM_011534995.1 | 3798-3897 | AAGATACAGCAACAATCATTGCTACTGAC TTGTTCAACCCCTTAGTTACACTGTATGA TCAACATATAACAAGATACAGTGGAATGG CCCATACAGTATA (SEQ ID NO: 105) |
| LRRC16A** | NM_001173977.1 | 4823-4922 | TTGGAGATAAATGAAATAACTGGACACAC ACTCACACAAGTAACACCACAGCAGACCT CGGAGTACTGCTAAGTGTACCTGTGTCAA ATCCGCACAGGAC (SEQ ID NO: 106) |
| MAGED1 | NM_001005333.1 | 2523-2622 | ATTTTGGAGATCCCTGGTCCAGAATTCCA TTTACCTTCTGGGCCAGATACCACCAGAA TGCCCGCTCCAGATTCCCTCAGACCTTTG CCGGTCCCATTAT (SEQ ID NO: 107) |
| MAP2K6 | NM_002758.3 | 1281-1380 | TCTTGGAGACTAAAAAGCAGTGGACTTAA TCGGTTGACCCTACTGTGGATTGGTGGGT TTCGGGGTGAAGCAAGTTCACTACAGCAT CAATAGAAAGTCA (SEQ ID NO: 108) |
| MAPRE1 | NM_012325.2 | 1983-2082 | AGTGAAGGCCATCGTTACCTTGGGATCTG CCAGGCTGGGGTGTTTTCGGTATCTGCTG TTCACAGCTCTCCACTGTAATCCGAATAC |

TABLE 1-continued 200-gene FFPE-based classifier. One asterisk next to the Gene Name
indicates inclusion in the 100-gene FFPE-based classifier and two
asterisks indicates inclusion in the 75-gene FFPE-based classifier.

| Gene Name | Accession | Position | Target Sequence |
|---|---|---|---|
| | | | TTTGCCAGTGCAC<br>(SEQ ID NO: 109) |
| MLLT3** | NM_001286691.1 | 3370-3469 | TTTACTAGAAATTCAGCCGAAAAGAAGAG<br>AAATGAAGAAATACTTCTGGATCCAAAGG<br>TTCGTCACTGGATCAGCCTTAAGAAAGTC<br>TCTATGTGTGCTA<br>(SEQ ID NO: 110) |
| MLPH | NM_001042467.2 | 1966-2065 | GACAGGACAGAGAGACAGAGCAGCCCTGC<br>ACTGTTTTCCCTCCACCACAGCCATCCTG<br>TCCCTCATTGGCTCTGTGCTTTCCACTAT<br>ACACAGTCACCGT<br>(SEQ ID NO: 111) |
| MPP1 | NM_001166460.1 | 1596-1695 | AGTTTTGTGTCAGCTTCCAGCTCTCTGCA<br>GCTATCCTAATTCAGCCAGTAAGGTTCAG<br>TCTTCTTGCTCAGGCTCCTGAAGGGTTGA<br>TTCTCCTGATAGA<br>(SEQ ID NO: 112) |
| MRAP2** | XM_011535401.1 | 1557-1656 | GGTTGTGCTGAAACAGCTCTTCTGAGAAC<br>TTCCAACCACCCATGCTCTAACCTGGAGA<br>CAGCCATCCCCTGCCTCAGAATAAGTACC<br>AATTCGTAGTACA<br>(SEQ ID NO: 113) |
| MT2A | NM_005953.3 | 226-325 | CAGGGCTGCATCTGCAAAGGGGCGTCGGA<br>CAAGTGCAGCTGCTGCGCCTGATGCTGGG<br>ACAGCCCCGCTCCCAGATGTAAAGAACGC<br>GACTTCCACAAAC<br>(SEQ ID NO: 114) |
| MYRIP | NM_001284423.1 | 4445-4544 | GACAAAAATGTGTACTGTGTAAGCCTTGC<br>AAACAAAAAACAACAAAAAAGAAGCAGCA<br>GCAGCAGCCTGCTGTGTGGCATCTGAACT<br>TTTATAAAGGTTT<br>(SEQ ID NO: 115) |
| NCAPH* | NM_015341.3 | 2399-2498 | GCTTATACCCAGGCTGTAGCCAACTACCA<br>ACGTGCCTGTTTGTTTGTTGCTCTTTCCT<br>TCTCTCCATCATAGTCTGGGTGCCAGCGC<br>CCTGAAGCTCCGT<br>(SEQ ID NO: 116) |
| NDFIP2 | NM_001161407.1 | 2177-2276 | ACTCATTTTCAAGTTATGGAAATGTGTTT<br>GTGGCATATAGGACTGTGGGGTCTGTGTG<br>TGTAGTGAGAGTGTGTAGCCACTATTATA<br>ACTGGAATTTAAT<br>(SEQ ID NO: 117) |
| NEDD9** | NM_001142393.1 | 4061-4160 | TCCATAGTCTGTCTCCTCACATCTGTTAG<br>TATTGACACAGCACAGACACCACAAGCCA<br>TCAGGTTCTTCATGGGGCAGGTGAAATAC<br>TTCTACCCCATGG<br>(SEQ ID NO: 118) |
| NOL4L** | NM_080616.4 | 5608-5707 | CCACCTCCGGGGAGGGGCACAGGGCTCCA<br>GATAGTAAGCACTTAAGGCAAACAGTGGA<br>TGGCACCAACTTTTAAAGGTGACTCTATT<br>AATGGCTTCACCT<br>(SEQ ID NO: 119) |
| NR1I2 | NM_003889.3 | 4017-4116 | ATGAGTCTGTAGGAGCAAGGGCACAAACT<br>GCAGCTGTGAGTGCGTGTGTGTGATTTGG<br>TGTAGGTAGGTCTGTTTGCCACTTGATGG<br>GGCCTGGGTTTGT<br>(SEQ ID NO: 120) |
| NUCB2 | NM_005013.2 | 999-1098 | TTACATGATGTCAATAGTGATGGATTCCT<br>GGATGAACAAGAATTAGAAGCCCTATTTA<br>CTAAAGAGTTGGAGAAAGTATATGACCCT<br>AAAAATGAAGAGG<br>(SEQ ID NO: 121) |

TABLE 1-continued 200-gene FFPE-based classifier. One asterisk next to the Gene Name
indicates inclusion in the 100-gene FFPE-based classifier and two
asterisks indicates inclusion in the 75-gene FFPE-based classifier.

| Gene Name | Accession | Position | Target Sequence |
|---|---|---|---|
| OSTM1 | NM_014028.3 | 2541-2640 | ACTTTCTCTGATCTGCTGTGATCCACTGA AAATGTGCTGGGGTTTGTTCTGCTGTCAC TGTTTATGCTGCTGGAACTTAGCACTGTC TTGATTTGAAGCA (SEQ ID NO: 122) |
| PAK6 | NM_001276718.1 | 3753-3852 | GGCCAGAGACAGGAATGTAAGGATTGGCA ACTGTGTTACCTTTCAAGTTTATCTCAAT AACCAGGTCATCAGGGACCCATTGTTCTC TTCAGAACCCTAT (SEQ ID NO: 123) |
| PALB2 | NM_024675.3 | 3551-3650 | GTTCCTGGAAGGTGACGTGAAAGATCACT GTGCAGCAGCAATCTTGACTTCTGGAACA ATTGCCATTTGGGACTTACTTCTCGGTCA GTGTACTGCCCTC (SEQ ID NO: 124) |
| PALLD | NM_001166108.1 | 5451-5550 | GTAAGAACACCAACCAACCAAGGTTTAAG TGATTAATAGGCTTGAGCACCGGGTGGCA GATGTTCTATGCAGTGTGGTTCAAGTTTC TTTGACCGCACTT (SEQ ID NO: 125) |
| PBX1 | NM_001204961.1 | 6321-6420 | TACCTGAACACTTGTACTCTTGAAGTCAC AACAAAATAATGATGAGCTTTTCACATCA CCTTTATGGTTTCAATCCCTAGCTCAAAG CTTCCTGGAATCT (SEQ ID NO: 126) |
| PCMTD2** | NM_001104925.1 | 2361-2460 | GCCTTGTGTGTGGAGAGCTTTCTATCTTA CCAAGTGGTAGGGCTAAAAGAACAACAGC CTTTTTGGTAGTCACATAGCAGAATGATC AGAGTTACATTGC (SEQ ID NO: 127) |
| PCP4 | NM_006198.2 | 156-255 | AGTTCAAGAAGAATTTGACATTGACATGG ATGCACCAGAGACAGAACGTGCAGCGGTG GCCATTCAGTCTCAGTTCAGAAAATTCCA GAAGAAGAAGGCT (SEQ ID NO: 128) |
| PDP1 | NM_001161779.1 | 3871-3970 | TGATCAAGATAGTAGTATTATTACACAAG AAACTTGGTCTGCAGTCTGGAAGCTTGTC TGCTCTATAGAAATGAAAATGCAGCATGA AGTTGACATTGTG (SEQ ID NO: 129) |
| PDZD2 | NM_178140.2 | 11011-11110 | ACCTCTGGCTTACCACATACACTATGCTA AAGTCATCAGCCACTGCTACTACATCTTG CCAGAAGGTTTCCCTCGCCAACAAACAGT TGAAATTTAAGGG (SEQ ID NO: 130) |
| PDZK1IP1 | NM_005764.3 | 237-336 | CTGGGGAACCTTCAGCCCTGGATGCAGGG CCTTATCGCGGTGGCCGTGTTCCTGGTCC TCGTTGCAATCGCCTTTGCAGTCAACCAC TTCTGGTGCCAGG (SEQ ID NO: 131) |
| PIGR | NM_002644.3 | 2303-2402 | ACATCCCTCGGAGGAAAAGAAGAGTTTGT TGCCACCACTGAGAGCACCACAGAGACCA AAGAACCCAAGAAGGCAAAAAGGTCATCC AAGGAGGAAGCCG (SEQ ID NO: 132) |
| PIGU | NM_080476.4 | 1317-1416 | TGGCACCTCTGGATTTATGCAGGAAGTGC CAACTCTAATTTCTTTTATGCCATCACAC TGACCTTCAACGTTGGGCAGATCCTGCTC |

TABLE 1-continued 200-gene FFPE-based classifier. One asterisk next to the Gene Name
indicates inclusion in the 100-gene FFPE-based classifier and two
asterisks indicates inclusion in the 75-gene FFPE-based classifier.

| Gene Name | Accession | Position | Target Sequence |
|---|---|---|---|
| | | | ATCTCTGATTACT<br>(SEQ ID NO: 133) |
| PITX2 | NM_000325.5 | 1707-1806 | TAAAGAAAGGGAGAGAAAGAGAAGCTATA<br>TAGAGAAAAGGAAACCACTGAATCAAAGA<br>GAGAGCTCCTTTGATTTCAAAGGGATGTC<br>CTCAGTGTCTGAC<br>(SEQ ID NO: 134) |
| PLCB1** | NMO15192.3 | 6569-6668 | ATAGAAAGTAGAGCTGTGTATTAAATTAG<br>ACTGTGTCTCTCTGATACCTTTACACTAC<br>TGAGAATAGCATGGTTTTGGCCATGTAAA<br>CCAATTTTCAAAG<br>(SEQ ID NO: 135) |
| PLCH1* | NM_014996.2 | 5794-5893 | CTGATTGAATTACAGACTGCGAACAACGG<br>CTTTCAGAATGAGGGACTTCCATCAGACT<br>CTAATGATAATAGTAGCACAAATTGAAAA<br>CTTCCCCAAAGCT<br>(SEQ ID NO: 136) |
| PNP | NM_000270.2 | 1151-1250 | TTTCTTCTACCAGACCCTTCTGGTGCCAG<br>ATCCTCTTCTCAAAGCTGGGATTACAGGT<br>GTGAGCATAGTGAGACCTTGGCGCTACAA<br>AATAAAGCTGTTC<br>(SEQ ID NO: 137) |
| POLD3 | NM_006591.1 | 2901-3000 | AGCAACCAAGCATGAACTTGATTAAGACC<br>AGAAGTTTGGGAGATGAGTCCTGGCATTA<br>TGTCTAGGACTAAAGCAGTGGCTTTGTAT<br>AGCAAGCTGAGTA<br>(SEQ ID NO: 138) |
| POP1** | NM_001145860.1 | 4129-4228 | CAAGGAGCCCTTTGTAGGACCAGTGTTCT<br>TAGTAGCGCGCTTTGGGCAGTGTGGCTGT<br>GTAGTGCATAGCTACCTCTGCAAGGTGAT<br>AACTAAGCCGGCA<br>(SEQ ID NO: 139) |
| PPP1R14C** | NM_030949.2 | 1581-1680 | CTTCCTTAGAAATAGGTTCTGGTAGCTTC<br>TGTGCCTGGGTAGTATCAGACCAGTGGGA<br>GTAAACCGAGTGTTAAGTGTCAAGGTGAG<br>AAAGCCTCACATT<br>(SEQ ID NO: 140) |
| PPP1R14D | NM_001130143.1 | 721-820 | GAAATGTGGACAAGGAGGGACATTTGCAT<br>ACTCCTACTGTCTGTGTGGTCACAGCTAG<br>TTTCTGTCAGCTGGGCTCTCTGGGAGAAA<br>GCTGGCTGTTGTC<br>(SEQ ID NO: 141) |
| PPP1R3D* | NM_006242.3 | 2942-3041 | TCACTACATTAACATGCAAGAGAGAGAGA<br>AGCCTTGTTACATTTCCTGCTATTTAACA<br>AACTGTCCAATTAGGTCAGCAAGCCTGTT<br>AGGGCCTTCACTG<br>(SEQ ID NO: 142) |
| PPP3CA | NM_000944.4 | 3632-3731 | GTATAAGTGCCCAAGTAATTCACTACAGC<br>CTAAAGCCTTGCCTTTGTAATTTGACTTC<br>TGACATGTTGGCAATCAAAGCATGCACTT<br>GTAACAATGAAAA<br>(SEQ ID NO: 143) |
| PRAP1 | NM_145202.4 | 79-178 | ATGAGGAGGCTCCTCCTGGTCACCAGCCT<br>GGTGGTTGTGCTGCTGTGGGAGGCAGGTG<br>CAGTCCCAGCACCCAAGGTCCCTATCAAG<br>ATGCAAGTCAAAC<br>(SEQ ID NO: 144) |
| PRC1 | NM_199413.2 | 2803-2902 | ATTGGGAGTCTGTTTGTTCCAATGGGTTG<br>AGCTGTCTTTGTCGTGGAGATCTGGAACT<br>TTGCACATGTCACTACTGGGGAGGTGTTC<br>CTGCTCTAGCTTC<br>(SEQ ID NO: 145) |

TABLE 1-continued 200-gene FFPE-based classifier. One asterisk next to the Gene Name
indicates inclusion in the 100-gene FFPE-based classifier and two
asterisks indicates inclusion in the 75-gene FFPE-based classifier.

| Gene Name | Accession | Position | Target Sequence |
|---|---|---|---|
| PRDX5 | NM_012094.4 | 601-700 | GGAAGGAGACAGACTTATTACTAGATGAT TCGCTGGTGTCCATCTTTGGGAATCGACG TCTCAAGAGGTTCTCCATGGTGGTACAGG ATGGCATAGTGAA (SEQ ID NO: 146) |
| PRLR | NM_000949.5 | 11449-11548 | AAGAAAAGGAAAGAGGATGTGGGTCAAAT AAAACACCGCATGGATGTTGATTGGTGAA TACTGGTGTAAGAAAAGGGAGCTCAGGAA TTTTTATTACTGT (SEQ ID NO: 147) |
| PRR15* | NM_175887.2 | 1421-1520 | AGCTTGAACTCTGTAGCCTCTCAAATGAA GAAGGTGGCTGTTATTTAGGACTCTGTGG AAAGCAAATCACAGTGCTGTTTTTAATGC CTGAGAAATGCAC (SEQ ID NO: 148) |
| PTPRO | NM_002848.3 | 4793-4892 | TACTGTCCAAGTTCTTTCTCAAGAAACCA CATCTGGTTCAGAAGAGTGTCAAGTTGGA CTCTTTGAACTCTGTTGCTGTCTGAGCAA TCGTGGTGCCTAG (SEQ ID NO: 149) |
| QPRT** | 242414_at.1 | 138-237 | AAAAGTTAGAAAACAAAACAAAACAGAAG TAAGATAAATAGCCAGAAGACCTTGGCGA CACCACCCGGCCCTGGTAGTT GTAACAATAATAA (SEQ ID NO: 150) |
| RAB27B | NM_004163.4 | 787-886 | ATGAAGCGAATGGAACAGTGTGTGGAGAA GACACAAATCCCTGATACTGTCAATGGTG GAAATTCTGGAAACTTGGATGGGGAAAAG CCACCAGAGAAGA (SEQ ID NO: 151) |
| RAMP1 | NM_005855.3 | 370-469 | CTGGGCTGCTTCTGGCCCAATGCAGAGGT GGACAGGTTCTTCCTGGCAGTGCATGGCC GCTACTTCAGGAGCTGCCCCATCTCAGGC AGGGCCGTGCGGG (SEQ ID NO: 152) |
| RAN | NM_001300796.1 | 1765-1864 | GTAGGGCAGCACAGCAGAGCAGGACATGG ATGAAATACTAGGAATATGCACAGTGGGG CAGTGTGGGGGCTTCTCAGTAATGGAGAA CAGTTGGTGAAAC (SEQ ID NO: 153) |
| RAP1GAP** | NM_001145657.1 | 2925-3024 | CTCTGGGCATGTCTGCTACAAATGGACAA GATTATTTCAGAGGTCACTGAAGACTGTG ATTACATGCACCTGCCTTAGAAGGTAGGA TTTTCTTCCCAGG (SEQ ID NO: 154) |
| RARRES3 | NM_004585.3 | 442-541 | CCCGCTGTAAACAGGTGGAAAAGGCCAAG GTTGAAGTTGGTGTGGCCACGGCGCTTGG AATCCTGGTTGTTGCTGGATGCTCTTTTG CGATTAGGAGATA (SEQ ID NO: 155) |
| RBMS1 | NM_002897.4 | 1629-1728 | TCCATATACCTTTCAACCTAATAAGTAAC TGTGAGATGTACAGAAAGGTGTTCTTACA TGAAGAAGGGTGTGAAGGCTGAACAATCA TGGATTTTTCTGA (SEQ ID NO: 156) |
| REG4** | NM_001159352.1 | 870-969 | AACGAATGCAACAAGCGCCAACACTTCCT GTGCAAGTACCGACCATAGAGCAAGAATC AAGATTCTGCTAACTCCTGCACAGCCCCG |

TABLE 1-continued 200-gene FFPE-based classifier. One asterisk next to the Gene Name
indicates inclusion in the 100-gene FFPE-based classifier and two
asterisks indicates inclusion in the 75-gene FFPE-based classifier.

| Gene Name | Accession | Position | Target Sequence |
|-----------|-----------|----------|-----------------|
| | | | TCCTCTTCCTTTC |
| | | | (SEQ ID NO: 157) |
| RETNLB* | NM_032579.2 | 189-288 | ATGGATAAGAAGATCAAGGATGTTCTCAA |
| | | | CAGTCTAGAGTACAGTCCCTCTCCTATAA |
| | | | GCAAGAAGCTCTCGTGTGCTAGTGTCAAA |
| | | | AGCCAAGGCAGAC |
| | | | (SEQ ID NO: 158) |
| RNF183 | NM_145051.3 | 655-754 | CTCCATCTTTTGGACCAAGCAGTTCCTTT |
| | | | GGGGTGTGGGGTGAGTGCTGTTCCCAGAC |
| | | | AAGAAACCAAACCTTTTTCGGTTGCTGCT |
| | | | GGGTATGGTGACT |
| | | | (SEQ ID NO: 159) |
| RNF43** | NM_001305544.1 | 3814-3913 | GAGTCCCAGAGAGGTAGAAAGGAGGAATT |
| | | | TCTGCTGGACTTTATCTGGGCAGAGGAAG |
| | | | GATGGAATGAAGGTAGAAAAGGCAGAATT |
| | | | ACAGCTGAGCGGG |
| | | | (SEQ ID NO: 160) |
| SAMD5** | NM_001030060.2 | 5961-6060 | TGCCCTGTTCCCCAAGCTTGTCAATGTTT |
| | | | AGAGATACTATTCGGGTTGCTAAAGCCAT |
| | | | TATTCATAGAAAATTTCTGCCCCTACAGA |
| | | | AGTGTGTGCATGG |
| | | | (SEQ ID NO: 161) |
| SEMA5A | NM_003966.2 | 11231-11330 | GCTTCCTGAGAGCTGTCTAGGTCTGTATC |
| | | | CCAGATTGTTGCTTAATGACATCTGACAG |
| | | | ATGCATTGTTTTCTGAAATCAGCTTAAGA |
| | | | CACCAATTGTGGC |
| | | | (SEQ ID NO: 162) |
| SERPINB1** | NM_030666.2 | 817-916 | GGACTAAACCTGAGAATCTCGATTTCATT |
| | | | GAAGTTAATGTCAGCTTGCCCAGGTTCAA |
| | | | ACTGGAAGAGAGTTACACTCTCAACTCCG |
| | | | ACCTCGCCCGCCT |
| | | | (SEQ ID NO: 163) |
| SESN1** | NM_001199933.1 | 2328-2427 | GGATCCTGACACTGGAGGGCAGCTGTCTT |
| | | | GTGCATTACTTGTGTTTCCAGCACCAAAG |
| | | | TTGTGGGACATGTTGCTGTAGACTGCTGC |
| | | | GCAGTCCTGGGTG |
| | | | (SEQ ID NO: 164) |
| SHROOM4** | NM_020717.3 | 7387-7486 | GGAGAGGTGAAAAGATAAAAAGCCTCCTT |
| | | | CAAGGTTAGGTTCAGGTTCTGTTTTCCAT |
| | | | TTAACCTCATGTGCCATAAAGCTGCCCAG |
| | | | GCACACCAGAGCC |
| | | | (SEQ ID NO: 165) |
| SLC25A37** | NM_016612.2 | 1724-1823 | TTTTAAGAGGGTTGAATTCTTCCATCAGG |
| | | | TGAACGAAAAAGGCAACAAAGTAATAAAT |
| | | | CAGTGAATGTGGCCGGCAGCTGTGTTTAG |
| | | | CCCCTCCAGATGG |
| | | | (SEQ ID NO: 166) |
| SLC30A2 | NM_001004434.1 | 2298-2397 | CCGACTCATCGAGACAACATGCCCAGTTA |
| | | | TCAGGGAGTCCTGTGTCACAAGGTCTGTC |
| | | | TCTGCCATTGTAAGCAAGTGCCTTGGGCG |
| | | | AGCTGGCCTCTGC |
| | | | (SEQ ID NO: 167) |
| SLC4A11** | NM_032034.2 | 2956-3055 | CCAGGGTGGGTGGGACTGAGCAGGATGGA |
| | | | TTTTCTTTTGATAAAAGAGTCGATGCCTG |
| | | | AAAGAGAAACCATTTCCTTGATTGTGTAA |
| | | | GGAACTTGCTGGA |
| | | | (SEQ ID NO: 168) |
| SLC9A2 | NM_003048.3 | 2631-2730 | TTGTCACTCTGAAACCTGATGCAACAGTG |
| | | | GAATCCATGTAAAACTCTCTGTGCATCTA |
| | | | AATACTTCTGGAGGGCGACAGATTCATGC |
| | | | CACGGATAAATGA |
| | | | (SEQ ID NO: 169) |

TABLE 1-continued 200-gene FFPE-based classifier. One asterisk next to the Gene Name
indicates inclusion in the 100-gene FFPE-based classifier and two
asterisks indicates inclusion in the 75-gene FFPE-based classifier.

| Gene Name | Accession | Position | Target Sequence |
|---|---|---|---|
| SLCO1B3** | NM_019844.3 | 2596-2695 | GGTAGTTGTAACTGCTAATAAAACCAGTG<br>ACTAGAATATAAGGGAGGTAAAAAGGACA<br>AGATAGATTAATAGCCTAAATAAAGAGAA<br>AAGCCTGATGCCT<br>(SEQ ID NO: 170) |
| SLCO2B1 | NM_001145211.2 | 3194-3293 | GCCTGGGTCTGTGTCACCTGGGGCAGTGT<br>GGATAATGTTTAGTTCTGTGACACTGTTT<br>TTTGGGGGTGGCACCTGGTTCTCCGATGC<br>CTGGGCTGGTGTC<br>(SEQ ID NO: 171) |
| SOCS6 | NM_004232.3 | 1883-1982 | CCAAACAAAATGAAGGATTATTTACAGGA<br>GAAGCACTACTGAAAGATTGAGAACCCTG<br>CATCTTGCACTTTGGGAATAAGAACAAGA<br>GATTGAAATACAG<br>(SEQ ID NO: 172) |
| SPIRE2** | NM_032451.1 | 1817-1916 | CTCTTCTGCAAGAGAGCCGTCTGCACTTC<br>CTGTAGCATAAAGATGAAGATGCCTTCTA<br>AGAAATTTGGACACATCCCTGTCTACACA<br>CTGGGCTTTGAGA<br>(SEQ ID NO: 173) |
| SRPK1 | NM_003137.4 | 4080-4179 | GGAAATGCTTCTCCACCAAATAAGGGCTT<br>TTTCCCCTATTTAAGGAGCCAGATGGATT<br>GAAAGATGTGGAAATAGGCAGCTGTAGAT<br>CTTGATCTTCCAG<br>(SEQ ID NO: 174) |
| ST6GALNAC1 | NM_018414.3 | 2104-2203 | AACACTTGAACCATGGACAAGACTCTCTC<br>AAGATGGCAAATGGCTAATTGAGGTTCTG<br>AAGTTCTTCAGTACATTGCTGTAGGTCCT<br>GAGGCCAGGGATT<br>(SEQ ID NO: 175) |
| STAT2 | NM_005419.3 | 4407-4506 | ATGTTCTCCTGATGTAGCTTGAGATATAA<br>AGGAAAGGCCCTGCACAGGTGGCTGTTTC<br>TTGTCTGTTATGTCAGAGGAACAGTCCTG<br>TTCAGAAAGGGGC<br>(SEQ ID NO: 176) |
| TC2N | NM_152332.4 | 2206-2305 | ACCTGGTATATCAAGTCTCTGTTAGTACT<br>ATTGGCATTTAGAAGACTTTACCATTATT<br>TCAGTGCTAGGCATTATTGATTAGGTCTT<br>GGCTCCACTGTTT<br>(SEQ ID NO: 177) |
| TCN1** | NM_001062.3 | 1006-1105 | ACAAAGACTCTTCTTGCGTCTCTGCTTCA<br>GGTAACTTCAACATCTCCGCTGATGAGCC<br>TATAACTGTGACACCTCCTGACTCACAAT<br>CATATATCTCCGT<br>(SEQ ID NO: 178) |
| TFAP2A** | NM_003220.2 | 2790-2889 | TGGGACCACCTGGTATTCTGTATTTTCAC<br>TGGCCATATTGGAAGCAGTTCTAGTTGCA<br>TTGTATTGAGTTGTGCTGGCAGTAGTTTC<br>CATGCCTGTCAAT<br>(SEQ ID NO: 179) |
| TMEM61 | NM_182532.1 | 881-980 | GTTCAGACTGCACGGGGAGGAAGTTAAAG<br>GCTCCTAGCAGGTCCTGAATCCAGAGACA<br>AAAATGCTGTGCCTTCTCCAGAGTCTTAT<br>GCAGTGCCTGGGA<br>(SEQ ID NO: 180) |
| TMEM64** | NM_001146273.1 | 2531-2630 | TGAGTAACAGTAAAGTTCATTTATATGTC<br>CATACCTAGAAGACCAGTGCAAATACTTT<br>GAGAGCACCTGGGTCTACAGGACATAATT |

TABLE 1-continued 200-gene FFPE-based classifier. One asterisk next to the Gene Name
indicates inclusion in the 100-gene FFPE-based classifier and two
asterisks indicates inclusion in the 75-gene FFPE-based classifier.

| Gene Name | Accession | Position | Target Sequence |
|---|---|---|---|
| | | | GGCATCTAAATCC (SEQ ID NO: 181) |
| TNFRSF11A | NM_001270949.1 | 1941-2040 | CAGTGTGTGTTCATTGTAAACACTTTTGG GAAAGGGCTAAACATGTGAGGCCTGGAGA TAGTTGCTAAGTTGCTAGGAACATGTGGT GGGACTTTCATAT (SEQ ID NO: 182) |
| TNNC2* | NM_003279.2 | 387-486 | AGACGGCTACATCGACCCGGAGGAGCTGG CTGAGATTTTCAGGGCCTCCGGGGAGCAC GTGACGGACGAGGAGATCGAATCTCTGAT GAAAGACGGCGAC (SEQ ID NO: 183) |
| TN54* | XM_005257744.1 | 3979-4078 | CACCCAGCCAGTGGTCGAGCACTGCCCCG CCGCCAAAGTCTGCAGAATGTGAGATGAG GTTCTCAAGGTCACAGGCCCCAGTCCCAG CCTGGGGGCTGGC (SEQ ID NO: 184) |
| TOMM34 | NM_006809.4 | 1437-1536 | AGACCCCAACTCACTGCAGTTCATCTGAA CAACCTGAGCTCCTGGGCCGGGGTGGAAG GAGGGGGATAAACCTAAGGCCCTGATCCA AAGCAGCCTGTTG (SEQ ID NO: 185) |
| TRIM7 | NM_033342.2 | 579-678 | AGGAGGCCAAGGAGCTCTTGGAGTCCAGG CTGAGGGTCTTGAAGAAGGAACTGGAGGA CTGTGAGGTGTTCCGGTCCACGGAAAAGA AGGAGAGCAAGGA (SEQ ID NO: 186) |
| TRNP1* | NM_001013642.2 | 1324-1423 | ATTTTAATAGATGTCATTGCTTCAAGTCT AACGGCGCCGGGAGGCCTGTTTGAGGGAA AACATTAGTTTGAAAAATCCCCGTTCCCT TCATCCACTGCCC (SEQ ID NO: 187) |
| TSPAN6** | NM_001278740.1 | 1792-1891 | TTAATTTCAGTCAGTCAATAGATGGCATC CCTCATCAGGGTTGCCAGATGGTGATAAC AGTGTAAGGCCTTGGGTCTAAGGCATCCA CGACTGGAAGGGA (SEQ ID NO: 188) |
| UGT8* | XM_006714303.2 | 3333-3432 | TACCTAATGTCATTCACTAACATGGAAGA GTTGTGAAAATTCTAGAGTGCTGTAAATC CTTGGCATACACTATGACAAACAACTTCA TTACTCTCCCACC (SEQ ID NO: 189) |
| UPF3A* | NM_023011.3 | 2016-2115 | AGAGTTCACACTATATAAAACCCAACAGC TTCAACTATTGCCCTTTCAACAGTTTTGC CACTGACCGGATAGAAACGGTTTCAGTCT CTGGATGGATGTG (SEQ ID NO: 190) |
| USP14* | NM_005151.3 | 2166-2265 | GGAAGTGTTGCTCTCATTGTGTGACTCAG TGCTGCTGTCCATCCCATGGAAACATGGG CACAATCAAGTATTTGTCCAGCCTATTGC AGGCTTTTCCTGA (SEQ ID NO: 191) |
| UTP15 | NM_032175.2 | 1666-1765 | AGAAACCTTGGGGATGATGGATATGCTTT TTGCCACCATGAGAAGGAAGGAAGGCACT TCTGTGTTGGAACACACATCTGATGGATT TCCAGAGAATAAG (SEQ ID NO: 192) |
| VAV3** | NM_001079874.1 | 2681-2780 | GAATGTTTTGTCTGTTGCCGTCAGCCGAA CTTTGTTATGGAGGGAGCAGCCTCACACA AGCAGAAACACTCCTGTGGATGGTATTGT AGCATGTATTGTT (SEQ ID NO: 193) |

TABLE 1-continued 200-gene FFPE-based classifier. One asterisk next to the Gene Name
indicates inclusion in the 100-gene FFPE-based classifier and two
asterisks indicates inclusion in the 75-gene FFPE-based classifier.

| Gene Name | Accession | Position | Target Sequence |
|---|---|---|---|
| WFDC2 | NM_006103.3 | 165-264 | CGCAAGAGTGCGTCTCGGACAGCGAATGC GCCGACAACCTCAAGTGCTGCAGCGCGGG CTGTGCCACCTTCTGCTCTCTGCCCAATG ATAAGGAGGGTTC (SEQ ID NO: 194) |
| XBP1 | NM_005080.3 | 1595-1694 | TGCCTCCAGTTTTAGGTCCTTTAGTTTGC TTCTGTAAGCAACGGGAACACCTGCTGAG GGGGCTCTTTCCCTCATGTATACTTCAAG TAAGATCAAGAAT (SEQ ID NO: 195) |
| ZCCHC24** | NM_153367.3 | 4394-4493 | CAAAGCCTGGCCTCGCCGCTCGGGAGCTT TGCCATCTGAGCCACGCCTCCTCCAGGCC ATGCTCCTTGAACTTGGAAATGTCAACCG GAGCCCTTACACC (SEQ ID NO: 196) |
| ZDHHC23** | NM_173570.3 | 3171-3270 | GGTTAGTGAAGACAAATGTCTTAAGAGGC TGCGATGTCTAGGTTGGGCTTGTGACTTC TTAGTGGCCTAGCCTTCTTGATGGCACCT TGAAAGTGAACTT (SEQ ID NO: 197) |
| ZG16B** | NM_145252.2 | 405-504 | AAGTCACCCTGCAGCCAGGCGAATACATC ACAAAAGTCTTTGTCGCCTTCCAAGCTTT CCTCCGGGGTATGGTCATGTACACCAGCA AGGACCGCTATTT (SEQ ID NO: 198) |
| ZNF415** | NM_001136038.2 | 1911-2010 | TAATCCATACTGGAAAGAAACCTTACAAA TGTAGTGATTGTGGGAAGTCCTTTAGTGT GCGCCCAAACCTCTTCAGACATCAAATTA TCCATACTAAGGA (SEQ ID NO: 199) |
| ZSCAN18** | NM_001145542.1 | 2231-2330 | GCGTGTGTTTACCTATATGGAGTAGCTCG CAGAGATCACAGAAATGCTTGCAGCCTAA GGCAGGGTTTTCAGACCGTGGGTCCCAGC CCATTTAGTAAAA (SEQ ID NO: 200) |
| ZWINT* | NM_007057.3 | 1125-1224 | GGACTGGTTTGAACACAGGGTGTGCAGAT GGGGAGGGGGTACTGGCCTTGGGCCTCCT ATGATGCAGACATGGTGAATTTAATTCAA GGAGGAGGAGAAT (SEQ ID NO: 201) |

[1]LNX2 is included in the 100-gene classifier but not the 200-gene classifier

III. Methods of Treating Colorectal Cancer

Colorectal cancer (CRC), also known as bowel cancer and colon cancer, is a cancer characterized by neoplasia in the colon, rectum, or vermiform appendix. The symptoms of colorectal cancer depend on the location of tumor in the bowel, and whether it has spread elsewhere in the body (metastasis). The classic warning signs include: worsening constipation, blood in the stool, decrease in stool caliber (thickness), loss of appetite, loss of weight, and nausea or vomiting in someone over 50 years old. While rectal bleeding or anemia are high-risk features in those over the age of 50, other commonly described symptoms including weight loss and change in bowel habit are typically only concerning if associated with bleeding.

Colorectal cancer is the third most commonly diagnosed cancer in the world, but it is more common in developed countries. More than half of the people who die of colorectal cancer live in a developed region of the world.

Most colorectal cancers are due to old age and lifestyle factors with only a small number of cases due to underlying genetic disorders. Greater than 75%-95% of colorectal cancer occurs in people with little or no genetic risk. Some non-genetic risk factors include diet, obesity, smoking, and lack of physical activity. Dietary factors that increase the risk include red and processed meat as well as alcohol. Another risk factor is inflammatory bowel disease, which includes Crohn's disease and ulcerative colitis. Some of the inherited genetic disorders that can cause colorectal cancer include familial adenomatous polyposis and hereditary non-polyposis colon cancer; however, these represent less than 5% of cases. It typically starts as a benign tumor, often in the form of a polyp, which over time becomes cancerous.

Colorectal cancer starts in the lining of the bowel. If left untreated, the cancer can grow into the muscle layers underneath, and then through the bowel wall. Most begin as a small growth on the bowel wall: a colorectal polyp or adenoma. These mushroom-shaped growths are usually benign, but some develop into cancer over time. Localized bowel cancer is usually diagnosed through colonoscopy. The most common form of colon cancer is adenocarcinoma. Other, rarer types include lymphoma, adenosquamous and squamous cell carcinoma.

Colon cancer staging is an estimate of the amount of penetration of a particular cancer. It is performed for diagnostic and research purposes, and to determine the best method of treatment. The systems for staging colorectal cancers depend on the extent of local invasion, the degree of lymph node involvement and whether there is distant metastasis.

Definitive staging can be done after surgery has been performed and pathology reports reviewed or after a colonoscopic polypectomy of a malignant pedunculated polyp with minimal invasion. Preoperative staging of rectal cancers may be done with endoscopic ultrasound.

The most common staging system is the TNM (for tumors/nodes/metastases) system, from the American Joint Committee on Cancer (AJCC). The TNM system assigns a number based on three categories. "T" denotes the degree of invasion of the intestinal wall, "N" the degree of lymph node involvement, and "M" the degree of metastasis. The broader stage of a cancer is usually quoted as a number I, II, III, IV derived from the TNM value grouped by prognosis; a higher number indicates a more advanced cancer and likely a worse outcome.

The treatment depends on the stage of the cancer. When colorectal cancer is caught at early stages (with little spread), it can be curable. For example, invasive cancers that are confined within the wall of the colon (TNM stages I and II) are often curable with surgery. If left untreated, they spread to regional lymph nodes (stage III). Cancer that metastasizes to distant sites (stage IV) is usually not curable.

Colorectal cancer is a disease originating from the epithelial cells lining the colon or rectum of the gastrointestinal tract, most frequently as a result of mutations in the Wnt signaling pathway that artificially increase signaling activity. The mutations can be inherited or acquired. The most commonly mutated gene in all colorectal cancer is the APC gene, which produces the APC protein—a "brake" on the accumulation of β-catenin protein. Without APC, β-catenin accumulates to high levels and translocates into the nucleus, binds to DNA, and activates the transcription of genes that are normally important for stem cell renewal and differentiation but when inappropriately expressed at high levels can cause cancer. While APC is mutated in most colon cancers, some cancers have increased β-catenin because of mutations in β-catenin (CTNNB1) that block its degradation, or they have mutation(s) or other genes with function analogous to APC such as AXIN1, AXIN2, TCF7L2, or NKD1.

Beyond the defects in the Wnt-APC-beta-catenin signaling pathway, other mutations must occur for the cell to become cancerous. The p53 protein, produced by the TP53 gene, normally monitors cell division and kills cells if they have Wnt pathway defects. Eventually, a cell acquires a mutation in the TP53 gene and transforms the tissue from an adenoma into an invasive carcinoma.

Other apoptotic proteins commonly deactivated in colorectal cancers are TGF-β and DCC (Deleted in Colorectal Cancer). TGF-β has a deactivating mutation in at least half of colorectal cancers. Sometimes TGF-β is not deactivated, but a downstream protein named SMAD is. DCC commonly has deletion of its chromosome segment in colorectal cancer.

Surgery remains the primary treatment, while chemotherapy and/or radiotherapy may be recommended depending on the individual patient's staging and other medical factors. As such, it can be a challenge to determine how aggressively to treat a particular patient, especially after surgery.

Surgeries can be categorized into curative, palliative, bypass, fecal diversion, or open-and-close. Curative surgical treatment can be offered if the tumor is localized. Very early cancer that develops within a polyp can often be cured by removing the polyp (i.e., polypectomy) at the time of colonoscopy.

In colon cancer, a more advanced tumor typically requires surgical removal of the section of colon containing the tumor with sufficient margins, and radical en-bloc resection of mesentery and lymph nodes to reduce local recurrence (i.e., colectomy). If possible, the remaining parts of colon are anastomosed to create a functioning colon. In cases when anastomosis is not possible, a stoma (artificial orifice) is created. Curative surgery on rectal cancer includes total mesorectal excision (lower anterior resection) or abdominoperineal excision.

Chemotherapy is used to reduce the likelihood of metastasis developing, shrink tumor size, or slow tumor growth. Chemotherapy is often applied after surgery (adjuvant), before surgery (neoadjuvant), or as the primary therapy (palliative). The treatments listed here have been shown in clinical trials to improve survival and/or reduce mortality rate and have been approved for use by the U.S. Food and Drug Administration. In Stage I colon cancer, no chemotherapy is offered, and surgery is the definitive treatment. The role of chemotherapy in Stage II colon cancer is debatable and is usually not offered unless risk factors are identified. It is also known that the people who carry abnormalities of the mismatch repair genes do not benefit from chemotherapy. For Stage III and Stage IV colon cancer, chemotherapy is typically an integral part of treatment.

If cancer has spread to the lymph nodes or distant organs, which is the case with stage III and stage IV colon cancer respectively, adding chemotherapy agents fluorouracil, capecitabine or oxaliplatin increases life expectancy. If the lymph nodes do not contain cancer, the benefits of chemotherapy are controversial. If the cancer is widely metastatic or unresectable, treatment is then palliative. Typically in this setting, a number of different chemotherapy medications may be used. Chemotherapy drugs for this condition may include capecitabine, fluorouracil, irinotecan, oxaliplatin and UFT. The drugs capecitabine and fluorouracil are interchangeable, with capecitabine being an oral medication while fluorouracil being an intravenous medicine. Some specific regimens used for CRC are FOLFOX, FOLFOXIRI, and FOLFIRI. Antiangiogenic drugs, such as bevacizumab, ramucirumab, afilbercept, and regorafenib, are often added in first line therapy. Another class of drugs used in the second line setting are epidermal growth factor receptor inhibitors, such as cetuximab and panitumumab.

Colorectal cancer patients that have a mutation in the KRAS gene do not respond to therapies that inhibit the epidermal growth factor receptor (EGFR), such as cetuximab and panitumumab. Patients are now tested for the KRAS gene mutation before being offered these EGFR-inhibiting drugs. However, having the normal KRAS version does not guarantee these drugs will benefit the patient.

Immunotherapy with immune checkpoint inhibitors, such was nivolumab and pembrolizumab, has been found to be useful for a type of colorectal cancer with mismatch repair deficiency and microsatellite instability.

IV. Kits and Diagnostics

Kits are envisioned containing diagnostic agents, therapeutic agents, and/or other therapeutic and delivery agents.

The kit may comprise reagents capable of use in determining the expression level of at least a portion of the genes listed in Table 1. For example, reagents of the kit may include at total number of samples, total number of consensus samples, and number used in data set V1 (used for training the classifier) and V2 (used in validating the classifier).

TABLE 2

| Summary of data sets used in training and validating the CMS classifier. | | | | | | |
|---|---|---|---|---|---|---|
| Dataset | Platform | Tissue | Total | Consensus Samples | V1 (train) | V2 (validate) |
| AMC_AJC CII | Affy HG133plus2 | FF | 90 | 80 | 49 | 31 |
| French (GSE33113) | Affy HG133plus2 | FF | 556 | 466 | 273 | 185 |
| NKIAZ (GSE35896) | Affy HG133plus2 | FF | 62 | 51 | 33 | 18 |
| G5E13067 | Affy HG133plus2 | FF | 74 | 57 | 31 | 25 |
| G5E13294 | Affy HG133plus2 | FF | 155 | 124 | 66 | 58 |
| G5E14333 | Affy HG133plus2 | FF | 157 | 129 | 72 | 57 |
| G5E20916 | Affy HG133plus2 | FF | 90 | 45 | 22 | 23 |
| G5E23878 | Affy HG133plus2 | FF | 35 | 24 | 18 | 6 |
| G5E37892 | Affy HG133plus2 | FF | 130 | 107 | 64 | 41 |
| KFSYSCC | Affy HG133plus2 | FF | 307 | 229 | 125 | 102 |
| PETACC3 | Affy ADXCRC | FFPE | 688 | 526 | 315 | 211 |
| TCGA | RNAseq | FF | 573 | 449 | 261 | 189 |
| GSE2109 | Affy HG133plus2 | FF | 293 | 244 | 0 | 239 |
| G5E17536 | Affy HG133plus2 | FF | 177 | 147 | 0 | 144 |
| Total | | | 3396 | 2678 | 1329 | 1329 | least 20, 25, 30, 35, 40, 45, 50, 55, 60, 65, 70, 75, 80, 85, 90, 95, or 100 probes that constitute a Nanostring nCounter codeset, as well as reagents to prepare the target nucleic acids for analysis.

The kit may also comprise a suitable container means, which is a container that will not react with components of the kit, such as an eppendorf tube, a syringe, a bottle, or a tube. The container may be made from sterilizable materials such as plastic or glass.

The kit may further include an instruction sheet that outlines the procedural steps of the methods, such as the same procedures as described herein or are otherwise known to those of ordinary skill.

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Patients and Samples

CRCSC training and validation data sets: CRCSC data sets were used to train and validate the CMS classifier. Samples that were part of the "consensus" set in Guinney et al. (2015) were used for this exercise, meaning that they had "gold standard" CMS status, defined based on agreement among the six different subtyping systems, against which they could be compared to assess classification accuracy. Table 2 shows the data sets used, including tissue type (fresh frozen (FF) or formalin-fixed paraffin embedded (FFPE)), Several subsets of the validation dataset (V2) can also be considered separately to investigate different aspects of the classifiers' performance. Besides assessing classification performance on the entire validation data set (V2), performance for these subsets was also considered:

Out of sample Validation Data (V2o): The validation data set contained one data set (GSE2109) for which none of the samples were in the training data set V1, so performance on this data set consisting of 239 samples is also given to highlight the out-of-sample predictive accuracy.

Affymetrix Validation Data (V2a): A subset of 929 of the V2 samples were Affymetrix data, and these are also summarized to highlight the performance of classifiers in the Affymetrix, FF setting.

Affymetrix Probeset Validation Data (V2ap): A subset of the 929 samples in the Affymetrix validation data set, 713 samples in total, had fRMA probe-level data, making it feasible to assess individual probe sets for strength of signal and use in designing the Nanostring code sets. This subset was assessed to compare single-probe and multiple-probeset Affymetrix quantifications for the best CMS classifier.

RNAseq Validation Data (fCGA): The TCGA data set was the only one comprised of RNAseq data, so predictive performance was also summarized on the 189 TCGA samples in the validation data set V2 to assess performance of the classifier for RNAseq data.

Preprocessing: The data were preprocessed as described in the online methods in Guinney et al. (2015). Briefly, the data sets from the Gene Expression Omnibus were normalized using robust multi-array average (RMA) implemented in the affy package (Gautier et al., 2004), and all private and public Affymetrix data sets were renormalized using single-sample frozen RMA method (McCall et al., 2010) in.frma package of Bioconductor. Level 3 TCGA RNAseq data were downloaded for colon and rectal sites from the TCGA data portal (January 2014). The counts were normalized using RSEM (Li & Dewey, 2011) and then log transformed.

ComBat (Johnson et al., 2007) was used to adjust for batch effects between GA and HiSeq samples.

Outliers were detected and removed from further analysis. A sample was deemed an outlier if it was flagged based on the distribution of gene expression values using the array-QualityMetrics package (Kauffman et al., 2009) and either had a distance greater than 2.5 in the plot of the first two principle components or was flagged based on pairwise distance in the arrayQualityMetrics package.

For the various data sets, representative probe sets were selected for each gene based on consistency from calculating a "correlation of correlations" to a reference data set. ComBat was used to remove data set (batch) effects, and genes were further filtered using a variability and correlation threshold. This resulted in a set of 5,973 genes with expression values for each sample in the combined data set. Quantile normalization was subsequently used using this set of 5,973 genes.

Nanostring Technical Variability Pilot Study: A pilot study to assess the technical reproducibility of the Nanostring assay. FFPE samples from six patients were run on the custom Nanostring platform described below with 472 signature genes and 28 housekeeping genes, normalizing as described below, all in duplicate.

Nanostring Paired FF/FFPE Data Set: Matched FF and FFPE samples were obtained from 78 patients who were part of the CRCSC data set within Guinney et al. (2015), plus FFPE alone for another 7 patients, and FF alone for another 2 patients. All of these samples were part of the CRCSC "consensus samples" that have "gold standard" CMS calls, but none of them were used in the CRCSC training data set V1 used for training the classifier. Matching FF and FFPE samples were obtained from an additional 73 patients who were not part of the CRCSC cohort, and so did not have a gold standard CMS classification. The criteria for patient and sample selection are described below and reflect patients with locoregional colonic adenocarcinoma after adequate clinical staging as per the NCCN guidelines (D'Angelica et al., 2002). For sample selection and processing, the criteria applied by TCGA were implemented as well as additional criteria like tissue block with tumor not facing the block and covered by formalin to lower the likelihood of RNA degradation.

Inclusion and exclusion criteria for patient selection for UH2: Patients were included based on adequate clinical staging, operation at UTMDACC, and pathologic stage III primary colon adenocarcinoma.

Sample/specimen inclusion criteria for UH2: Samples having matched frozen and FFPE samples available were used. In addition, more than one block of tumor needed to be available from resection specimens. Archival blocks with tumor were not exposed on the paraffin block. Tumor cellularity was greater than 60% after microdissection for signet ring or mucinous well differentiated adenocarcinoma. Tumor necrosis was less than 20%.

Histopathologic Review/RNA Extraction and Pre-analytical Quality Control: Fresh frozen and selected FFPE blocks were processed at the Research Histopathology Core Facility to procure Hematoxylin & Eosin (H&E) and unstained slides. Snap frozen samples were cut with frozen section microtome from OCT block and H&E stained sections prepared from each piece of frozen tissue of the tumor. The H&E stained sections were reviewed by an experienced gastrointestinal pathologist. Reviews included tumor cellularity as well as necrosis and area of the tumor with highest cellularity were marked. The part of tumor in the OCT block corresponding to the marked tumor on H&E section was macrodissected and tissue sent to the Bio-specimen Extraction Core (BER) in dry ice. No more than 10 frozen specimens were processed each day by the RHCF. Formalin-fixed paraffin embedded tissue from the selected block was cut to prepare 5 micron thick section on 21 slides. The first and 21st slides were stained and reviewed for tumor cellularity, necrosis and area of the tumor with highest cellularity. The matching area from slides 2 to 22 were macrodissected by BER for nucleic acid extraction.

DNA and RNA was be extracted from frozen samples by AllPrep DNA/RNA minikit (QIAGEN, Netherlands) and from FFPE by AllPrep DNA/RNA FFPE kit (QIAGEN, Netherlands). These kits were selected because prior studies validating the nCounter system used the same kit. The quantity and quality of extracted RNA was measured by the Agilent 6000 Nano Assay and Agilent 6000 pico assay. The calculated RNA concentration, RNA integrity number (RIN), ribosomal ratio and electropherogram with RNA picks for each sample by both methods was stored in a database.

Gene Expression Analysis: The extracted RNA from frozen samples was divided into two and run on the Nanostring nCounter with custom codesets as described below as well as by Affyrnetrix, and the extracted RNA from FFPE samples was run on the Nanostring nCounter with custom codesets.

The design of the customized Nanostring codesets is described below. The nCounter conditions were optimized for these customized codesets after discussion with Nanostring. Both aliquots from the frozen samples and the paraffin samples were analyzed by the nCounter system. A maximum of 2 (12 samples per cartridge) cartridges were run in one experiment to minimize the chances of faded signals.

Preprocessing of Nanostring Data: The Nanostring QA/QC guidelines were followed to decide on the need of repeating the array for a sample. The nCounter gene expressions were first normalized using Nanostring's internal positive and negative controls, as recommended, and then dividing by the geometric mean of the 28 reference genes. Since the set of 472 signature genes were selected to have moderate or high expression values, no issues of low expressing genes were encountered, as documented by some researchers working with the Nanostring nCounter system. As described below, for each sample, quantile normalization was performed to map the Nanostring/FFPE expression values onto the scale of the samples in the CRCSC training data in order to enable direct application of the classifier trained on the large CRCSC data set.

Assessing performance of CMS classifier assay in a CLIA certified laboratory: The Nanostring assay with top 200 genes (CRC CMS-200) including those in CMS-100, was further validated at a CLIA-certified Molecular Diagnostic Laboratory (MDL) to apply this assay as one of integral biomarker for a phase II clinical trial assessing safety and efficacy of dual TGF-β trap: anti-PD-L1 molecule M7824 (EMD-Serono) in CMS4 subtype of metastatic colon cancer. Validation was performed before the assay was used as an integral biomarker. Thirty-five tumor samples were used to validate the assay across 10 runs for total of 120 reactions. All 35 samples were included in the CRCSC study and gold standard CMS was known for these samples. Input for the assay was 250 ng of total RNA extracted from FFPE tumor tissue with 20% or higher tumor cellularity. The design of the codesets was similar to those built for the research laboratory, except the oligonucleotides for codesets were provided to the Nanostring by the Integrated DNA technologies. Accuracy, analytical sensitivity, and analytical specificity were assessed by comparing calls MDL CMS panel with CRCSC Affymetrix reported calls (gold standard as described earlier). Reproducibility was assessed across original run and 3 or more repeat runs without re-extraction of RNA, repeat runs with re-extraction of RNA and by 2 technicians. A positive (CMS 4) control of previously tested CMS4 sample and negative control of previously tested non-CMS4 were run alongside each run. A tumor is classified in to a CMS if the gene expression score (probability of a CMS) for the subtype was >0.58. A tumor with gene expression score>0.45 or <0.58 for any CMS was classified to have mixed CMS.

Assessing performance of CMS classifier as a prognostic marker in stage IV colorectal cancer: Patients with a CMS determination from the Nanostring based gene expression score were pooled from three separate sources, including two clinical trials; a phase II trial assessing safety and efficacy of dual TGF-β trap: anti-PD-L1 molecule M7824 (EMD-Serono) in CMS4 subtype of colon cancer (n=125) and a phase II trial assessing trametinib and durvalumab in microsatellite stable colorectal cancer (n=19) and Assessment of Targeted Therapies Against Colorectal Cancer (AT-TACC Program) Screening Protocol (n=103). ATTACC is a clinical protocol which enrolled patients with stage IV/treatment refractory colorectal cancer for molecular characterization of tumor tissue. The ATTACC samples and the samples from the trametinib/durvalumab study were characterized by CRC CMS-100 assay at the research molecular diagnostic laboratory, while samples from patients enrolled in M7824 clinical trial were characterized by CRC CMS-200 performed at the molecular diagnostic laboratory. Since all three studies were performed in patients with stage IV CRC and high (>90%) concordance between CRC CMS-100 vs. CRC CMS-200, we combined the three data sources to improve our power to detect subtype specific survival differences. Median overall survival was calculated from date of stage IV diagnosis to death or date of last follow up, which was censored. Survival patterns were visualized with Kaplan Meier survival curves and compared using the log-rank test. Graphs were generated using IBM SPSS Statistics 24.

Example 2—Statistics Methods

Development and Validation of CMS Classifier on CRCSC: An analytical workflow was used to build an optimized classifier mainly designed for FF samples using the CRCSC data, upon which the FFPE-based classifier was also based. The goals were to (1) develop an optimized classifier and (2) find out how parsimonious the classifier could be while still yielding acceptable classification accuracy. A more parsimonious classifier with fewer genes has greater potential for validation for clinical use.

Following are the steps that were followed in building and validating this classifier:

Step 1. As described above, the CRCSC data sets were split into a training data set, V1, consisting of 1,329 samples from 12 studies, and a validation data set, V2, including 1,329 samples from 14 studies. The performance of a subset of the validation data that were Affymetrix U133Plus2.0 arrays was also considered, which consisted of 929 Samples from 12 Studies (V2a), a subset of those that had fRMA probe-level data consisting of 713 samples from 10 studies (V2ap), the subset of TCGA validation data to summarize performance for RNAseq data (TCGA), and also summarized results from GSE2109 separately (V2o) to provide a summary of out-of-sample performance since no samples from this study were used in the training data VI.

Step 2. Four-fold cross validation was used on the V1 data set to build classifiers using a number of different modeling strategies and reduced gene lists. Modeling strategies and gene lists are given below. Here, the four-fold cross validation procedure is described in more detail.

Step 2a. The training data set V1 was split into four subsets, containing 332, 332, 332, and 333 samples, respectively, for use in a four-fold cross validation model building strategy.

Step 2b. For each modeling strategy, the model was fit to each of the four 3/4 subsets, optimizing tuning parameters using nested cross validation, and assessed accuracy for predicting the gold standard CMS on the left-out 1/4 subset. Tuning parameters that showed the best accuracy were selected as optimal parameters for each subset.

Step 2c. The predictive accuracy of each modeling strategy was summarized as a function of number of genes, allowing us to both assess which modeling strategy appears to be best and what minimum number of genes are needed for accurate CMS classification.

Step 3. Choosing the best modeling strategy, the classification accuracy was computed in the validation data set V2 as well as the various subsets mentioned above, and the results were again summarized as a function of number of genes in the model.

Classification Modeling Strategies: The following classification modeling strategies were considered:

Linear Discriminant Analysis: A principal component decomposition of the training data sample-by-gene matrix was performed, and then a linear discriminator was built. The sole tuning parameter was the number of principal components kept.

Quadratic Discriminant Analysis: After principal component decomposition, a quadratic discriminator was built and, once again, the only tuning parameter was the number of principal components to keep.

K-Nearest Neighbor: Each test sample was assigned to the most common class among its k-nearest neighbors in training data. Various distance metrics based on kernel densities can be used to find k-nearest neighbors. The Rpackage knn developed by Schleip et al. (2016) was used to fit k-nearest neighbor models. The tuning parameters were k (the number of neighbors) and the kernel used in the distance matric. k from 1 up to 15 was considered, and triangular, rectangular, Epanechnikov, and optimal kernels were considered. See Schleip et al. (2016) for details of the kernels.

Random Forest: The R package random.Forest developed by Breiman (2001) was used to fit random forest models. A random forest classifier aggregates across a number of classification trees fitted to a series of random subsets of the given data set. The procedure proceeds as follows:

1. Draw N bootstrap samples from the original data set.
2. For each bootstrap sample, grow a regression tree. At each node, randomly sample m of the predictors and choose the best split among those variables.
3. Predict the new data by aggregating the predictions across the N trees.

Tuning parameter was predictor size m with N fixed at 500. Ten values of m that were equally spaced from 1 up to the maximum number of predictors were considered.

Rotation Forest: Rotation forests (Rodriguez & Kuncheva, 2006) combine together principal component decompositions and random forests. The steps are:

1. Draw N bootstrap samples from the original data set.
2. For each bootstrap sample, grow a regression tree. Split the predictors into K subsets. For each subset, rotate the predictors by using a principal component decomposition performed on the given bootstrap data and subset of predictors.
3. Predict the new data by aggregating the predictions of the N trees.

Tuning parameter was K with N fixed at 500. Ten values of K that were equally spaced from 1 up to the half of the maximum number of predictors were considered.

Weighted Support Vector Machine (wSVM): The function svm was used in the R package e1071 to fit the support vector machines. The settings Type="C-classification" and scale=F were chosen, and radial, linear, and polynomial kernels and cost functions 0.1, 0.5, 1, 5, 10, 50, 100, 150, and 200 were considered. Pairwise coupling was used to produce probability estimates for each CMS (see Ting-Fan Wu et al., (2004)). In order to take imbalance among CMS in the training set into account, class weights were given as 1/the number of training samples belonging to each class. These weights allowed larger penalty for misclassification in smaller class when optimizing the SVM objective function, with the hope of obtaining a classifier with more even performance across CMS. See Chih-Chung Chang & Chih-Jen Lin (2001) for details on how class weights work.

Distance-weighted Discrimination (DWD): Distance-weighted Discrimination (DWD; Marron et al., 2007) finds a separating hyperplane minimizing the sum of reciprocals of distances from observations to the hyperplane. DWD was originally proposed to overcome the "data filing" issue when n<p in the support vector machine. This method was extended to the multiple-class setting by Huang et al. (2013). The proposed optimization problem in DWD can be reformulated as loss+penalty. The penalty term involves in a parameter that controls the mount of the penalty. This penalty parameter was the sole tuning parameter. Eight different values of the penalty parameters were considered: 100, 200, 400, 800, 1200, 1600, 2000, and 2400.

Ensemble Methods: Ensemble methods were also considered in which the consensus was taken after applying multiple classifiers described above. If one class had the most votes, select it and stop. Otherwise, drop the classifier with the lowest 4-fold CV performance and repeat. Ensembles including the best 3, 4, and 5 classification methods, as determined by 4-fold CV, were considered.

Gene Ranking Strategy: In order to compare classification strategies and evaluate the minimum number of genes for accurate classification, the genes were ordered in decreasing order of their classification importance and each classification strategy was applied for a range of model sizes, ranging from 5,973 genes all the way down to 2 genes. A boosting procedure was designed based on multi-class AdaBoost (Zhu et al., 2009) to order the genes. The basic idea is that samples are repeatedly re-weighted during the algorithm so that the next best gene can focus more on samples that were misclassified at the previous step. The procedure can be viewed as a forward stage-wise additive selection. The boosting procedure proceeds as follows:

1. Given N samples in the data set, initialize the sampling weights $w_1=1$ for i=1, . . . , N.
2. Initialize the outcome gene list A={ }.
3. Initialize the candidate gene list C={1, . . . , G}, where G=5973 is the initial set of genes.
4. From m=1, . . . , G
    a. Fit a weighted multinomial logistic regression for each gene in C.

b. For each gene, compute the weighted misclassification rate $$Err_g = \frac{\sum_{i=1}^{N} w_i I(\text{sample } i \text{ misclassified in model for gene } g)}{\sum_{i=1}^{N} w_i}$$

c. Add the best gene with smallest Err=min($Err_g$) to set A, and remove it from set C.
d. Compute $\alpha$=log{(1−Err)/Err}+log(K−1), where K=4 is the number of classes.
e. Update the weights to weight misclassified samples more heavily
    $w_i = w_i \{\alpha \times I(\text{sample i is misclassified})\}$ with I{•} an indicator function.

This procedure produced a list of genes ranked in descending order of their CMS classification importance. By using the same reduced gene sets for each classification method, a straightforward comparison of which method appears to perform better was gained, to find the minimum gene set size yielding good classification performance, to fairly compare the various methods at any desired model size, and to consider ensemble methods that involve combinations of individual methods.

Details of wSVM classifier: The results below reveal that the best classifier was the wSVM. Here, how to apply this classifier is described in detail. The user calls the wSVM function with an N by P matrix of expression values for P genes for each of N samples with the column names as Entrez IDs, and the function will quantile normalize the data and apply the wSVM to get class predictions. After pairwise coupling, probabilities of each CMS are obtained for sample i, $\pi_{ij}$ such that $$\sum_{j=1}^{4} \pi_{ij} = 1,$$

with $\alpha_i = \max_j \{\pi_{ij}\}$ indicating the highest CMS class probability for that sample, which is considered a measure of CMS classification confidence. There are two possible rules to classify a sample into a CMS group based on these measures:

1. Most Likely CMS: Classify sample i into the most likely CMS, {j: $\pi_{ij}=\max(\pi_{ij})$}, regardless of classification confidence $\alpha_i$. One benefit of this strategy is that it provides a predicted CMS for each sample.
2. Confidence Threshold: Classify sample i into the most likely CMS as long as the classification confidence $\alpha_i$ is above some threshold $\delta$ (e.g. 0.50, 0.80 or 0.90), and otherwise consider indeterminate {Choose CMS j: $\pi_{ij}=\max(\pi_{ij})$ if $\pi_{ij}>\delta$, otherwise CMS indeterminate}. This strategy most closely matches the classification strategy used in the classifiers presented in Guinney et al. (2015).

Design of Custom Nanostring Codesets: Custom Nanostring Code sets were designed using the genes present in the best classifier from the CRCSC data set. As can be seen in the results, the classifier obtained excellent performance even for signatures with as few as 50-100 genes, which is an order of magnitude that would be feasible for a clinical assay. However, for initial Nanostring design, approximately 500 genes were selected, with the expectation that only a subset of these genes would show high FF/FFPE concordance for the reasons mentioned above, leaving us with enough genes with high concordance to use in our Nanostring FFPE classifier.

A custom Nanostring platform was designed with 500 code sets including 472 signature probe sets and 28 reference probe sets. First, the top 500 genes from the boosting procedure were chosen. The code sets were designed for each gene to be located in the genomic region containing the single Affymetrix 133-2 Plus2.0 probe set that was most highly correlated with the fRMA gene-level expression level for each of the top 500 genes, and the best 472 for which the correlation between the probe set and gene-level summaries were at least 0.70 (54% had correlations of at least 0.90) were selected. This is a novel customized approach for choice of probe sets compared with NanoString's usual strategy of selecting code sets for genes themselves, and this approach is more likely to lead to a FFPE classifier recapitulating the accuracy of our Affymetrix-based CRCSC classifier.

The wSVM classifier was retrained using only these specific 472 genes with the CRCSC training data set V1 and applying this classifier to 713 samples in the CRCSC validation data V2 that had fRMA probe-level measurements (V2ap) using only these single-probe measurements mapped to the scale of the gene-level summaries by affine transformation. These results give an upper bound on the performance that can be expected for the Nanostring, FFPE-based classifier built based on code sets designed to match these genes.

Reference Code Sets: The 28 reference code sets were selected from an initial set of 74 candidates were assembled that included the reference probe sets on the Nanostring PanCan array plus the most commonly used reference genes from a thorough survey of all published papers involving Nanostring nCounter expression data in cancer from 2015-2016, selecting those with small variance and evidence of no difference CMS groups (p>0.05 inANOVA) in the preliminary data (Chen et al., 2015; Ligibel et al., 2015; Prat et al., 2016; Veldman-Jones et al., 2015; Wallden et al., 2015).

Nanostring Pilot Study Analysis: For the six samples run in duplicate on the custom Nanostring code set, linear mixed models were fit for each of the 472 signature genes with a random effect per sample, the biological variability $\sigma^2_u$, and technical variability $\sigma^2_e$ were estimated, and then the percent variability explained by biological factors, $PBV=\sigma^2_u/(\sigma^2_u+\sigma^2_e)\times100$, was computed with values near 100% indicating negligibly low levels of technical variability and smaller values indicating substantial technical variability. The coefficient of variation was also calculated for each gene, computed as $CV=\sigma_e/\mu$. Then, the distribution of PBV and CV across genes was summarized by a six-number summary, including minimum, maximum, 25th percentile (Q25), 75th percentile (Q75), median (QSO), and mean.

Development of Nanostring Classifier: Rather than trying to train the CMS classifier anew on our 178 FFPE samples, instead the following novel strategy was used to port the CMS classifier designed for Affymetrix platform on FF samples over to the Nanostring/FFPE setting that efficiently utilizes the vast information available in the CRCSC training and validation data sets.

1. Identify a reduced gene set with high concordance between tissue and platform type. Individual genes with r>0.80 across paired measurements were chosen, computed using patients for which their patient-specific FF/FFPE correlation was greater than 0.75. Note that this custom Nanostring platform was purposefully built to have more codesets (472) than needed for accurate CMS classification so that even after filtering out genes with low Nanostring/Affymetrix and/or FF/FFPE concordance, enough (~100) would be left to have accurate CMS classification for the Nanostring/FFPE setting.

2. Train a new model with the reduced gene set on the CRCSC training data V1, assess accuracy for Affymetrix/FF samples using CRCSC validation data V2 to obtain new wSVM classifier rp.

3. Quantile normalize the Nanostring expression values $$X_{i,g}^{N_{FFPE}}$$

for the chosen gene set for each FFPE sample to the scale of the Affymetrix/FF samples in the CRCSC data set, e.g.

$$X_{i,g}^{*A_{FF}} = f_{1,g}(X_{i,g}^{N_{FFPE}}).$$

4. Apply the wSVM classifier yr from step 2 to the quantile normalized expressions $$X_{i,g}^{*A_{FF}}$$

to obtain a CMS classification and compute the probability for each CMS type $\pi_{ij}$, with $\alpha_i=\max(\pi_{ij})$ being the probability of the CMS with the highest probability.

Classify the subject into a CMS using one of the two rules described above, assigning to the "most likely CMS" with the highest probability or imposing a "confidence threshold" (e.g. $\alpha_i>0.50$, 0.80, or 0.90), defining the sample as "indeterminate" if below the confidence threshold. The classification accuracy of this strategy was assessed on 85 FFPE samples by comparing classification results with the gold standard "consensus" CMS calls from Guinney et al. (2015) for these samples, and to the 73 FFPE samples that were not part of the CRCSC cohort using the Affymetrix FF 4 72 gene classifier results as a pseudo-gold standard.

Sample Quality Assessment: For each FF and FFPE sample, RIN was computed to summarize the RNA quality, and for FFPE samples %200 nt was also computed as an additional QC statistic. These quantities were summarized through box plots and distributional summaries, and correlated them with sample-specific FF/FFPE correlation to assess whether samples with poor FF/FFPE correlation tended to have poor RNA quality, and correlated with CMS classification accuracy to assess how classification accuracy varied across RNA quality.

Example 3—Nanostring FFPE Classifier

Figure 2:
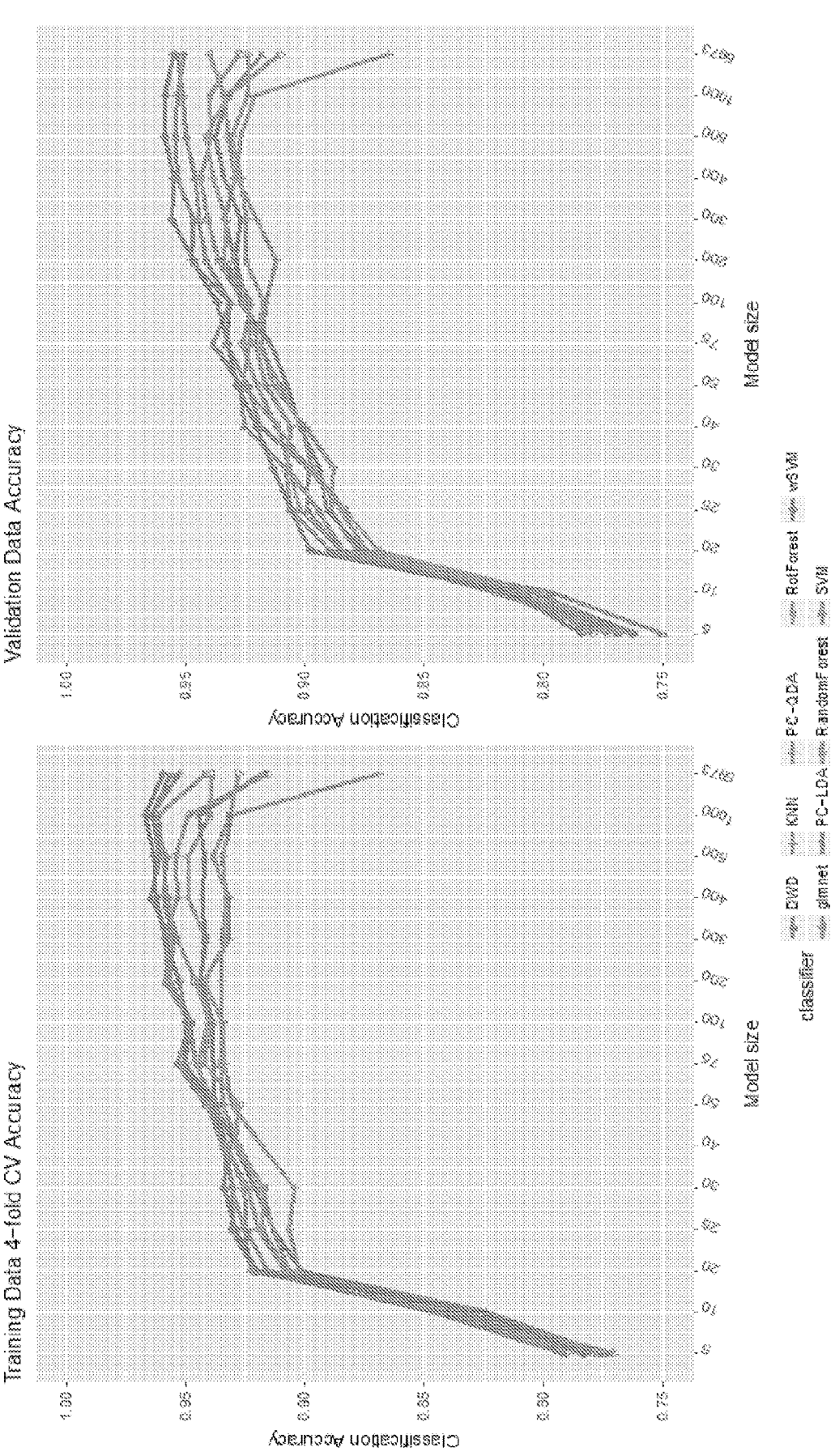
FIG. 2. Classification accuracy for training data V1 (based on 4-fold cross validation; left panel) and the full validation data V2 (right panel) for various methods as function of number of genes.

Comparison of Methods on CRCSC Data Set, 4-fold Cross Validation of Training Data V1: FIG. 2 and Table 3 present the classification accuracy of each proposed method using 4-fold cross validation of the training data set (V1) for models of various size from 5 genes up to the full set of 5,973 genes considered in Guinney et al. (2015), with gene lists determined by Multi-class Adaboost as described above. For all methods, classification was forced into a single CMS ("most likely CMS") and compared with the gold standard "consensus" CMS from Guinney et al. (2015).

All methods performed well, with performance that decayed only slowly with the number of genes. Improved performance was seen with refined gene lists smaller than the original 5,973 genes, with outstanding performance even for smaller models with several methods having 4-class accuracy of >0.94 for the 75 gene model, and >0.90 even for some of the 20-50 gene models.

The wSVM, SVM, and DWD methods appeared to have the best performance both for the full 5,973-gene model as well as the models with smaller gene sizes. Looking at performance by CMS (Tables 4A-7E), CMS3 was consistently the hardest subtype to classify across methods and gene sizes. For example, for the 500-gene model, the classification accuracies for CMS1 (0.959, 0.950, and 0.973 for wSVM, SVM, DWD, respectively), CMS2 (0.974, 0.976, and 0.972, respectively), and CMS4 (0.966, 0.952, and 0.946, respectively) were higher than CMS3 (0.926, 0.920, and 0.938, respectively).

Among these three methods, wSVM was chosen as the classifier moving forward. It was chosen over the SVM because of its more even performance across CMS, with better performance for the difficult CMS3, and over DWD because its ease of application relative to the DWD that requires special software to classify future samples.

TABLE 3

Classification accuracy on training data set V1 using 4-fold cross validation.

| V1 | 5 | 10 | 20 | 25 | 30 | 40 | 50 | 75 | 100 | 200 | 300 | 400 | 500 | 1000 | 5973 |
|---|---|---|---|---|---|---|---|---|---|---|---|---|---|---|---|
| wSVM | 0.783 | 0.827 | 0.920 | 0.929 | 0.934 | 0.933 | 0.938 | 0.950 | 0.950 | 0.953 | 0.959 | 0.962 | 0.963 | 0.967 | 0.959 |
| SVM | 0.792 | 0.847 | 0.921 | 0.931 | 0.93 | 0.935 | 0.941 | 0.950 | 0.947 | 0.956 | 0.955 | 0.959 | 0.958 | 0.965 | 0.953 |
| DWD | 0.775 | 0.824 | 0.916 | 0.925 | 0.926 | 0.933 | 0.941 | 0.953 | 0.948 | 0.959 | 0.956 | 0.965 | 0.961 | 0.964 | 0.956 |
| glmnet | 0.784 | 0.844 | 0.922 | 0.926 | 0.931 | 0.933 | 0.941 | 0.944 | 0.941 | 0.944 | 0.941 | 0.949 | 0.949 | 0.94 | 0.939 |
| PC-LDA | 0.781 | 0.834 | 0.901 | 0.913 | 0.921 | 0.929 | 0.938 | 0.938 | 0.938 | 0.944 | 0.942 | 0.943 | 0.942 | 0.944 | 0.918 |
| PC-QDA | 0.791 | 0.833 | 0.908 | 0.919 | 0.924 | 0.933 | 0.938 | 0.946 | 0.948 | 0.957 | 0.959 | 0.953 | 0.954 | 0.949 | 0.916 |
| RandomForest | 0.771 | 0.837 | 0.907 | 0.913 | 0.918 | 0.928 | 0.935 | 0.935 | 0.935 | 0.942 | 0.932 | 0.932 | 0.938 | 0.932 | 0.928 |
| RotForest | 0.777 | 0.841 | 0.908 | 0.918 | 0.917 | 0.929 | 0.928 | 0.942 | 0.94 | 0.946 | 0.953 | 0.958 | 0.959 | 0.962 | 0.941 |
| KNN | 0.78 | 0.824 | 0.902 | 0.907 | 0.904 | 0.918 | 0.931 | 0.934 | 0.935 | 0.935 | 0.935 | 0.933 | 0.935 | 0.931 | 0.869 |
| Ensemble3 | 0.789 | 0.831 | 0.91 | 0.917 | 0.926 | 0.935 | 0.941 | 0.947 | 0.944 | 0.953 | 0.95 | 0.945 | 0.95 | 0.95 | 0.914 |
| Ensemble4 | 0.788 | 0.831 | 0.912 | 0.916 | 0.926 | 0.937 | 0.941 | 0.949 | 0.946 | 0.953 | 0.949 | 0.946 | 0.95 | 0.951 | 0.922 |
| Ensemble5 | 0.789 | 0.837 | 0.916 | 0.926 | 0.932 | 0.938 | 0.947 | 0.95 | 0.95 | 0.953 | 0.953 | 0.953 | 0.958 | 0.959 | 0.938 |

TABLE 4A

Classification accuracy of CMS1 samples on training data set V1
using 4-fold cross validation as function of number of genes.

| | 5 | 10 | 20 | 25 | 30 | 40 | 50 | 75 | 100 | 200 | 300 | 400 | 500 | 1000 | 5973 |
|---|---|---|---|---|---|---|---|---|---|---|---|---|---|---|---|
| wSVM | 0.718 | 0.777 | 0.927 | 0.918 | 0.941 | 0.945 | 0.95 | 0.945 | 0.95 | 0.941 | 0.945 | 0.968 | 0.959 | 0.973 | 0.973 |
| SVM | 0.691 | 0.777 | 0.905 | 0.918 | 0.927 | 0.932 | 0.95 | 0.945 | 0.941 | 0.945 | 0.936 | 0.955 | 0.95 | 0.973 | 0.968 |
| DWD | 0.709 | 0.795 | 0.905 | 0.923 | 0.909 | 0.941 | 0.955 | 0.95 | 0.95 | 0.955 | 0.95 | 0.968 | 0.973 | 0.973 | 0.968 |
| glmnet | 0.677 | 0.795 | 0.891 | 0.909 | 0.905 | 0.927 | 0.936 | 0.927 | 0.936 | 0.927 | 0.927 | 0.936 | 0.936 | 0.932 | 0.918 |
| PC-LDA | 0.668 | 0.782 | 0.877 | 0.905 | 0.909 | 0.941 | 0.936 | 0.932 | 0.973 | 0.964 | 0.95 | 0.955 | 0.959 | 0.964 | 0.918 |
| PC-QDA | 0.686 | 0.782 | 0.905 | 0.941 | 0.918 | 0.955 | 0.959 | 0.955 | 0.982 | 0.982 | 0.968 | 0.968 | 0.977 | 0.973 | 0.9 |
| RandomForest | 0.668 | 0.764 | 0.859 | 0.891 | 0.882 | 0.905 | 0.909 | 0.886 | 0.918 | 0.927 | 0.909 | 0.905 | 0.918 | 0.909 | 0.895 |
| RotForest | 0.668 | 0.764 | 0.868 | 0.891 | 0.905 | 0.914 | 0.905 | 0.914 | 0.909 | 0.909 | 0.941 | 0.945 | 0.945 | 0.95 | 0.927 |
| KNN | 0.695 | 0.773 | 0.859 | 0.877 | 0.855 | 0.882 | 0.891 | 0.905 | 0.909 | 0.918 | 0.923 | 0.918 | 0.914 | 0.9 | 0.768 |
| Ensemble3 | 0.695 | 0.786 | 0.882 | 0.886 | 0.909 | 0.932 | 0.923 | 0.945 | 0.959 | 0.95 | 0.95 | 0.955 | 0.968 | 0.936 | 0.882 |
| Ensemble4 | 0.691 | 0.786 | 0.882 | 0.886 | 0.914 | 0.941 | 0.927 | 0.95 | 0.964 | 0.95 | 0.945 | 0.959 | 0.968 | 0.941 | 0.914 |
| Ensemble5 | 0.695 | 0.777 | 0.891 | 0.909 | 0.918 | 0.941 | 0.955 | 0.95 | 0.95 | 0.959 | 0.95 | 0.964 | 0.973 | 0.968 | 0.932 |

TABLE 4B

Classification accuracy of CMS1 samples on validation data set as function of number of genes.

| | 5 | 10 | 20 | 25 | 30 | 40 | 50 | 75 | 100 | 200 | 300 | 400 | 500 | 1000 | 5973 |
|---|---|---|---|---|---|---|---|---|---|---|---|---|---|---|---|
| wSVM | 0.716 | 0.793 | 0.875 | 0.862 | 0.866 | 0.901 | 0.905 | 0.931 | 0.914 | 0.927 | 0.957 | 0.94 | 0.94 | 0.944 | 0.931 |
| SVM | 0.664 | 0.793 | 0.866 | 0.871 | 0.875 | 0.901 | 0.905 | 0.931 | 0.914 | 0.94 | 0.948 | 0.948 | 0.944 | 0.935 | 0.94 |
| DWD | 0.69 | 0.776 | 0.858 | 0.862 | 0.879 | 0.897 | 0.901 | 0.918 | 0.905 | 0.927 | 0.94 | 0.953 | 0.944 | 0.944 | 0.953 |
| glmnet | 0.659 | 0.784 | 0.841 | 0.858 | 0.853 | 0.888 | 0.905 | 0.914 | 0.879 | 0.909 | 0.931 | 0.905 | 0.901 | 0.927 | 0.922 |
| PC-LDA | 0.651 | 0.793 | 0.866 | 0.853 | 0.862 | 0.866 | 0.871 | 0.892 | 0.905 | 0.914 | 0.914 | 0.944 | 0.944 | 0.931 | 0.922 |
| PC-QDA | 0.672 | 0.776 | 0.875 | 0.875 | 0.866 | 0.901 | 0.905 | 0.892 | 0.892 | 0.909 | 0.914 | 0.935 | 0.927 | 0.909 | 0.884 |
| RandomForest | 0.677 | 0.759 | 0.858 | 0.862 | 0.879 | 0.866 | 0.892 | 0.897 | 0.892 | 0.909 | 0.901 | 0.909 | 0.909 | 0.897 | 0.918 |
| RotForest | 0.655 | 0.767 | 0.858 | 0.866 | 0.892 | 0.888 | 0.905 | 0.905 | 0.914 | 0.922 | 0.944 | 0.944 | 0.914 | 0.927 | 0.914 |
| KNN | 0.694 | 0.793 | 0.841 | 0.841 | 0.828 | 0.853 | 0.866 | 0.875 | 0.858 | 0.849 | 0.866 | 0.853 | 0.849 | 0.832 | 0.711 |
| Ensemble3 | 0.703 | 0.78 | 0.862 | 0.849 | 0.871 | 0.862 | 0.897 | 0.892 | 0.897 | 0.918 | 0.922 | 0.927 | 0.918 | 0.909 | 0.866 |
| Ensemble4 | 0.703 | 0.776 | 0.866 | 0.853 | 0.879 | 0.862 | 0.897 | 0.892 | 0.897 | 0.922 | 0.922 | 0.931 | 0.918 | 0.914 | 0.892 |
| Ensemble5 | 0.69 | 0.78 | 0.866 | 0.871 | 0.875 | 0.875 | 0.897 | 0.901 | 0.897 | 0.927 | 0.935 | 0.944 | 0.935 | 0.931 | 0.927 |

TABLE 4C

Classification accuracy CMS1 samples with out of sample prediction set as function of number of genes.

| | 5 | 10 | 20 | 25 | 30 | 40 | 50 | 75 | 100 | 200 | 300 | 400 | 500 | 1000 | 5973 |
|---|---|---|---|---|---|---|---|---|---|---|---|---|---|---|---|
| wSVM | 0.694 | 0.776 | 0.837 | 0.837 | 0.878 | 0.918 | 0.878 | 0.959 | 0.939 | 0.939 | 0.98 | 0.98 | 0.98 | 0.959 | 0.918 |
| SVM | 0.612 | 0.816 | 0.796 | 0.857 | 0.878 | 0.918 | 0.898 | 0.98 | 0.918 | 0.98 | 1 | 1 | 0.98 | 0.959 | 0.959 |
| DWD | 0.612 | 0.776 | 0.816 | 0.857 | 0.898 | 0.898 | 0.918 | 0.939 | 0.939 | 0.98 | 1 | 0.98 | 0.98 | 0.98 | 0.98 |
| glmnet | 0.592 | 0.776 | 0.796 | 0.857 | 0.857 | 0.898 | 0.939 | 0.918 | 0.857 | 0.918 | 0.98 | 0.939 | 0.939 | 0.98 | 0.959 |
| PC-LDA | 0.592 | 0.796 | 0.857 | 0.918 | 0.939 | 0.898 | 0.857 | 0.878 | 0.939 | 0.939 | 0.939 | 0.959 | 0.98 | 0.939 | 0.939 |
| PC-QDA | 0.612 | 0.776 | 0.857 | 0.898 | 0.878 | 0.878 | 0.898 | 0.898 | 0.918 | 0.939 | 0.959 | 0.98 | 0.959 | 0.959 | 0.939 |
| RandomForest | 0.673 | 0.735 | 0.878 | 0.898 | 0.898 | 0.878 | 0.939 | 0.959 | 0.959 | 0.959 | 0.98 | 0.98 | 0.98 | 0.98 | 0.98 |
| RotForest | 0.653 | 0.755 | 0.878 | 0.898 | 0.959 | 0.898 | 0.939 | 0.959 | 0.918 | 0.959 | 0.98 | 0.98 | 0.959 | 0.939 | 0.898 |
| KNN | 0.694 | 0.816 | 0.857 | 0.816 | 0.857 | 0.857 | 0.857 | 0.857 | 0.878 | 0.816 | 0.878 | 0.857 | 0.857 | 0.837 | 0.673 |
| Ensemble3 | 0.673 | 0.776 | 0.837 | 0.857 | 0.918 | 0.878 | 0.959 | 0.918 | 0.939 | 0.918 | 1 | 0.98 | 0.98 | 0.98 | 0.918 |
| Ensemble4 | 0.673 | 0.776 | 0.857 | 0.857 | 0.939 | 0.878 | 0.959 | 0.918 | 0.939 | 0.918 | 1 | 0.98 | 0.98 | 0.98 | 0.939 |
| Ensemble5 | 0.653 | 0.776 | 0.857 | 0.878 | 0.918 | 0.878 | 0.939 | 0.918 | 0.918 | 0.918 | 1 | 0.98 | 0.98 | 0.98 | 0.98 |

TABLE 4D

Classification accuracy CMS1 samples with TCGA dataset as function of number of genes.

| | 5 | 10 | 20 | 25 | 30 | 40 | 50 | 75 | 100 | 200 | 300 | 400 | 500 | 1000 | 5973 |
|---|---|---|---|---|---|---|---|---|---|---|---|---|---|---|---|
| wSVM | 0.897 | 0.897 | 1 | 1 | 1 | 1 | 1 | 1 | 1 | 0.966 | 0.966 | 0.966 | 0.966 | 1 | 1 |
| SVM | 0.897 | 0.897 | 1 | 1 | 1 | 1 | 1 | 1 | 1 | 0.966 | 1 | 1 | 1 | 1 | 1 |
| DWD | 0.931 | 0.897 | 1 | 1 | 1 | 1 | 1 | 1 | 1 | 0.966 | 0.931 | 1 | 0.966 | 1 | 1 |
| glmnet | 0.862 | 0.897 | 1 | 1 | 1 | 1 | 1 | 0.966 | 0.966 | 1 | 0.966 | 0.931 | 0.931 | 0.931 | 0.966 |
| PC-LDA | 0.862 | 0.966 | 1 | 1 | 1 | 1 | 1 | 1 | 1 | 1 | 1 | 1 | 1 | 1 | 1 |
| PC-QDA | 0.897 | 0.897 | 1 | 1 | 1 | 1 | 1 | 1 | 1 | 1 | 1 | 1 | 1 | 0.966 | 0.966 |
| RandomForest | 0.862 | 0.897 | 0.966 | 0.966 | 0.966 | 1 | 1 | 0.966 | 0.966 | 0.966 | 0.931 | 0.931 | 0.931 | 0.897 | 0.897 |
| RotForest | 0.897 | 0.897 | 0.966 | 1 | 1 | 1 | 1 | 1 | 1 | 0.966 | 0.966 | 1 | 1 | 1 | 0.966 |
| KNN | 0.793 | 0.931 | 0.966 | 0.966 | 0.931 | 0.897 | 0.966 | 0.966 | 0.931 | 0.931 | 0.931 | 0.931 | 0.966 | 0.931 | 0.862 |
| Ensemble3 | 0.862 | 0.897 | 1 | 1 | 1 | 1 | 1 | 1 | 1 | 1 | 0.931 | 0.966 | 0.966 | 0.931 | 0.966 |
| Ensemble4 | 0.862 | 0.897 | 1 | 1 | 1 | 1 | 1 | 1 | 1 | 1 | 0.931 | 0.966 | 0.966 | 0.931 | 0.966 |
| Ensemble5 | 0.862 | 0.897 | 1 | 1 | 1 | 1 | 1 | 1 | 1 | 1 | 1 | 1 | 0.966 | 0.966 | 0.966 |
| Ensemble5 | 0.642 | 0.801 | 0.852 | 0.881 | 0.881 | 0.909 | 0.915 | 0.943 | 0.92 | 0.949 | 0.955 | 0.955 | 0.949 | 0.932 | 0.955 |

TABLE 4E

Classification accuracy CMS1 samples with Affymetrix set as function of number of genes.

| | 5 | 10 | 20 | 25 | 30 | 40 | 50 | 75 | 100 | 200 | 300 | 400 | 500 | 1000 | 5973 |
|---|---|---|---|---|---|---|---|---|---|---|---|---|---|---|---|
| wSVM | 0.642 | 0.801 | 0.852 | 0.881 | 0.881 | 0.909 | 0.915 | 0.943 | 0.92 | 0.949 | 0.955 | 0.955 | 0.949 | 0.932 | 0.955 |
| SVM | 0.67 | 0.773 | 0.847 | 0.869 | 0.886 | 0.898 | 0.903 | 0.92 | 0.909 | 0.943 | 0.955 | 0.955 | 0.949 | 0.943 | 0.96 |
| DWD | 0.659 | 0.784 | 0.824 | 0.858 | 0.852 | 0.892 | 0.903 | 0.926 | 0.886 | 0.915 | 0.955 | 0.926 | 0.926 | 0.96 | 0.943 |
| glmnet | 0.636 | 0.79 | 0.852 | 0.858 | 0.858 | 0.869 | 0.847 | 0.892 | 0.898 | 0.903 | 0.903 | 0.943 | 0.943 | 0.932 | 0.926 |
| PC-LDA | 0.653 | 0.773 | 0.869 | 0.869 | 0.869 | 0.903 | 0.903 | 0.886 | 0.881 | 0.903 | 0.909 | 0.938 | 0.926 | 0.909 | 0.903 |
| PC-QDA | 0.659 | 0.75 | 0.858 | 0.869 | 0.886 | 0.858 | 0.892 | 0.909 | 0.892 | 0.903 | 0.909 | 0.909 | 0.909 | 0.898 | 0.926 |
| RandomForest | 0.636 | 0.767 | 0.858 | 0.875 | 0.898 | 0.886 | 0.915 | 0.909 | 0.909 | 0.926 | 0.949 | 0.938 | 0.898 | 0.92 | 0.909 |
| RotForest | 0.699 | 0.812 | 0.847 | 0.847 | 0.841 | 0.864 | 0.875 | 0.892 | 0.864 | 0.858 | 0.869 | 0.852 | 0.841 | 0.841 | 0.75 |
| KNN | 0.699 | 0.778 | 0.852 | 0.858 | 0.875 | 0.858 | 0.909 | 0.903 | 0.892 | 0.92 | 0.943 | 0.926 | 0.915 | 0.92 | 0.886 |
| Ensemble3 | 0.699 | 0.778 | 0.858 | 0.864 | 0.886 | 0.858 | 0.909 | 0.903 | 0.892 | 0.926 | 0.943 | 0.932 | 0.915 | 0.926 | 0.898 |
| Ensemble4 | 0.676 | 0.784 | 0.852 | 0.875 | 0.875 | 0.875 | 0.903 | 0.909 | 0.898 | 0.926 | 0.938 | 0.943 | 0.938 | 0.938 | 0.932 |
| Ensemble5 | 0.642 | 0.801 | 0.852 | 0.881 | 0.881 | 0.909 | 0.915 | 0.943 | 0.92 | 0.949 | 0.955 | 0.955 | 0.949 | 0.932 | 0.955 |

TABLE 5A

Classification accuracy of CMS2 samples on training data set V1 using 4-fold cross validation as function of number of genes.

| | 5 | 10 | 20 | 25 | 30 | 40 | 50 | 75 | 100 | 200 | 300 | 400 | 500 | 1000 | 5973 |
|---|---|---|---|---|---|---|---|---|---|---|---|---|---|---|---|
| wSVM | 0.807 | 0.855 | 0.921 | 0.923 | 0.929 | 0.933 | 0.941 | 0.962 | 0.96 | 0.96 | 0.969 | 0.974 | 0.974 | 0.985 | 0.807 |
| SVM | 0.897 | 0.935 | 0.945 | 0.959 | 0.95 | 0.954 | 0.962 | 0.972 | 0.971 | 0.978 | 0.981 | 0.983 | 0.976 | 0.985 | 0.897 |
| DWD | 0.804 | 0.857 | 0.919 | 0.924 | 0.923 | 0.929 | 0.938 | 0.966 | 0.957 | 0.966 | 0.966 | 0.974 | 0.972 | 0.979 | 0.804 |
| glmnet | 0.904 | 0.928 | 0.948 | 0.952 | 0.95 | 0.955 | 0.959 | 0.974 | 0.971 | 0.967 | 0.962 | 0.969 | 0.971 | 0.962 | 0.904 |
| PC-LDA | 0.902 | 0.928 | 0.972 | 0.966 | 0.967 | 0.978 | 0.986 | 0.988 | 0.99 | 0.99 | 0.993 | 0.993 | 0.995 | 0.991 | 0.902 |

TABLE 5A-continued

Classification accuracy of CMS2 samples on training data set V1 using 4-fold cross validation as function of number of genes.

| | 5 | 10 | 20 | 25 | 30 | 40 | 50 | 75 | 100 | 200 | 300 | 400 | 500 | 1000 | 5973 |
|---|---|---|---|---|---|---|---|---|---|---|---|---|---|---|---|
| PC-QDA | 0.898 | 0.919 | 0.952 | 0.95 | 0.957 | 0.964 | 0.974 | 0.976 | 0.971 | 0.983 | 0.985 | 0.985 | 0.981 | 0.978 | 0.898 |
| RandomForest | 0.871 | 0.938 | 0.952 | 0.957 | 0.959 | 0.974 | 0.972 | 0.974 | 0.971 | 0.974 | 0.969 | 0.964 | 0.972 | 0.971 | 0.871 |
| RotForest | 0.885 | 0.95 | 0.96 | 0.962 | 0.964 | 0.962 | 0.971 | 0.981 | 0.981 | 0.978 | 0.993 | 0.985 | 0.988 | 0.991 | 0.885 |
| KNN | 0.902 | 0.931 | 0.978 | 0.969 | 0.974 | 0.979 | 0.988 | 0.99 | 0.979 | 0.981 | 0.99 | 0.993 | 0.99 | 0.988 | 0.902 |
| Ensemble3 | 0.874 | 0.873 | 0.974 | 0.967 | 0.969 | 0.981 | 0.981 | 0.991 | 0.986 | 0.986 | 0.986 | 0.991 | 0.991 | 0.986 | 0.874 |
| Ensemble4 | 0.874 | 0.873 | 0.974 | 0.967 | 0.969 | 0.981 | 0.981 | 0.991 | 0.986 | 0.986 | 0.986 | 0.991 | 0.991 | 0.986 | 0.874 |
| Ensemble5 | 0.867 | 0.909 | 0.971 | 0.969 | 0.969 | 0.972 | 0.988 | 0.986 | 0.985 | 0.985 | 0.99 | 0.991 | 0.991 | 0.993 | 0.867 |

TABLE 5B

Classification accuracy of CMS2 samples on validation data set as function of number of genes.

| | 5 | 10 | 20 | 25 | 30 | 40 | 50 | 75 | 100 | 200 | 300 | 400 | 500 | 1000 | 5973 |
|---|---|---|---|---|---|---|---|---|---|---|---|---|---|---|---|
| wSVM | 0.87 | 0.873 | 0.943 | 0.951 | 0.958 | 0.953 | 0.955 | 0.957 | 0.957 | 0.962 | 0.967 | 0.964 | 0.972 | 0.972 | 0.967 |
| SVM | 0.842 | 0.886 | 0.934 | 0.951 | 0.946 | 0.964 | 0.96 | 0.971 | 0.957 | 0.974 | 0.971 | 0.976 | 0.971 | 0.974 | 0.972 |
| DWD | 0.749 | 0.792 | 0.903 | 0.91 | 0.908 | 0.927 | 0.932 | 0.939 | 0.938 | 0.943 | 0.946 | 0.945 | 0.958 | 0.962 | 0.96 |
| glmnet | 0.87 | 0.877 | 0.932 | 0.941 | 0.943 | 0.95 | 0.957 | 0.96 | 0.962 | 0.964 | 0.953 | 0.964 | 0.969 | 0.967 | 0.977 |
| PC-LDA | 0.877 | 0.886 | 0.95 | 0.964 | 0.953 | 0.969 | 0.965 | 0.967 | 0.981 | 0.979 | 0.981 | 0.981 | 0.983 | 0.984 | 0.977 |
| PC-QDA | 0.891 | 0.88 | 0.927 | 0.936 | 0.958 | 0.96 | 0.962 | 0.969 | 0.965 | 0.967 | 0.967 | 0.967 | 0.972 | 0.972 | 0.951 |
| RandomForest | 0.846 | 0.903 | 0.948 | 0.955 | 0.96 | 0.974 | 0.967 | 0.971 | 0.958 | 0.964 | 0.967 | 0.967 | 0.969 | 0.967 | 0.964 |
| RotForest | 0.889 | 0.912 | 0.943 | 0.955 | 0.965 | 0.96 | 0.967 | 0.972 | 0.969 | 0.967 | 0.977 | 0.969 | 0.967 | 0.976 | 0.969 |
| KNN | 0.87 | 0.906 | 0.96 | 0.962 | 0.974 | 0.981 | 0.981 | 0.972 | 0.974 | 0.977 | 0.984 | 0.988 | 0.988 | 0.983 | 0.976 |
| Ensemble3 | 0.828 | 0.868 | 0.951 | 0.969 | 0.969 | 0.977 | 0.972 | 0.974 | 0.976 | 0.977 | 0.977 | 0.981 | 0.984 | 0.981 | 0.974 |
| Ensemble4 | 0.83 | 0.87 | 0.951 | 0.971 | 0.969 | 0.977 | 0.971 | 0.974 | 0.976 | 0.977 | 0.977 | 0.981 | 0.984 | 0.981 | 0.974 |
| Ensemble5 | 0.854 | 0.873 | 0.951 | 0.967 | 0.967 | 0.971 | 0.976 | 0.976 | 0.972 | 0.977 | 0.981 | 0.981 | 0.983 | 0.981 | 0.981 |

TABLE 5C

Classification accuracy CMS2 samples with out of sample prediction set as function of number of genes.

| V2o | 5 | 10 | 20 | 25 | 30 | 40 | 50 | 75 | 100 | 200 | 300 | 400 | 500 | 1000 | 5973 |
|---|---|---|---|---|---|---|---|---|---|---|---|---|---|---|---|
| wSVM | 0.899 | 0.876 | 0.944 | 0.933 | 0.955 | 0.933 | 0.944 | 0.933 | 0.944 | 0.944 | 0.966 | 0.955 | 0.966 | 0.966 | 0.966 |
| SVM | 0.888 | 0.865 | 0.933 | 0.955 | 0.955 | 0.944 | 0.955 | 0.933 | 0.966 | 0.966 | 0.966 | 0.966 | 0.966 | 0.966 | 0.966 |
| DWD | 0.764 | 0.809 | 0.899 | 0.91 | 0.899 | 0.91 | 0.91 | 0.91 | 0.888 | 0.91 | 0.933 | 0.944 | 0.966 | 0.966 | 0.966 |
| glmnet | 0.91 | 0.888 | 0.921 | 0.91 | 0.933 | 0.921 | 0.921 | 0.955 | 0.944 | 0.955 | 0.933 | 0.933 | 0.944 | 0.989 | 0.989 |
| PC-LDA | 0.91 | 0.888 | 0.966 | 0.978 | 0.966 | 0.989 | 0.944 | 0.989 | 0.978 | 0.978 | 0.978 | 0.989 | 0.989 | 0.989 | 0.978 |
| PC-QDA | 0.933 | 0.888 | 0.944 | 0.944 | 0.989 | 0.978 | 0.966 | 0.989 | 0.966 | 0.978 | 0.978 | 0.989 | 0.989 | 0.989 | 0.966 |
| RandomForest | 0.865 | 0.899 | 0.966 | 0.966 | 0.966 | 0.989 | 0.978 | 0.978 | 0.978 | 0.978 | 0.978 | 0.989 | 0.978 | 0.978 | 0.978 |
| RotForest | 0.899 | 0.921 | 0.966 | 0.966 | 0.966 | 0.966 | 0.978 | 0.989 | 0.966 | 0.966 | 0.978 | 0.966 | 0.966 | 0.989 | 0.989 |
| KNN | 0.865 | 0.899 | 0.966 | 0.966 | 0.989 | 0.989 | 1 | 0.955 | 0.978 | 0.989 | 0.978 | 1 | 0.989 | 1 | 0.966 |
| Ensemble3 | 0.831 | 0.854 | 0.978 | 0.978 | 0.966 | 0.989 | 0.978 | 0.966 | 0.989 | 0.978 | 0.978 | 0.989 | 0.989 | 0.989 | 0.978 |
| Ensemble4 | 0.843 | 0.854 | 0.978 | 0.978 | 0.966 | 0.989 | 0.978 | 0.966 | 0.989 | 0.978 | 0.978 | 0.989 | 0.989 | 0.989 | 0.978 |
| Ensemble5 | 0.899 | 0.865 | 0.978 | 0.978 | 0.978 | 0.978 | 0.978 | 0.978 | 0.978 | 0.978 | 0.978 | 0.989 | 0.989 | 0.989 | 0.989 |

TABLE 5D

Classification accuracy CMS2 samples with TCGA dataset as function of number of genes.

| TCGA | 5 | 10 | 20 | 25 | 30 | 40 | 50 | 75 | 100 | 200 | 300 | 400 | 500 | 1000 | 5973 |
|---|---|---|---|---|---|---|---|---|---|---|---|---|---|---|---|
| wSVM | 0.92 | 0.886 | 0.966 | 0.977 | 0.989 | 0.989 | 0.966 | 0.977 | 0.966 | 0.977 | 0.966 | 0.966 | 0.977 | 0.977 | 0.966 |
| SVM | 0.875 | 0.932 | 0.955 | 0.966 | 0.966 | 0.977 | 0.955 | 0.977 | 0.966 | 0.977 | 0.977 | 0.977 | 0.966 | 0.977 | 0.977 |
| DWD | 0.773 | 0.773 | 0.932 | 0.943 | 0.966 | 0.977 | 0.966 | 0.966 | 0.966 | 0.966 | 0.966 | 0.966 | 0.977 | 0.977 | 0.977 |
| glmnet | 0.909 | 0.875 | 0.966 | 0.966 | 0.977 | 0.989 | 0.966 | 0.966 | 0.966 | 0.943 | 0.955 | 0.966 | 0.955 | 0.955 | 0.989 |
| PC-LDA | 0.932 | 0.909 | 0.955 | 0.989 | 0.955 | 0.989 | 0.989 | 0.989 | 0.989 | 0.989 | 1 | 0.989 | 1 | 1 | 0.966 |
| PC-QDA | 0.92 | 0.943 | 0.966 | 0.955 | 0.966 | 0.966 | 0.977 | 0.977 | 0.977 | 0.966 | 0.966 | 0.966 | 0.955 | 0.966 | 0.932 |
| RandomForest | 0.92 | 0.92 | 0.989 | 0.989 | 0.989 | 0.989 | 0.989 | 0.989 | 0.966 | 0.966 | 0.966 | 0.966 | 0.966 | 0.966 | 0.966 |
| RotForest | 0.955 | 0.898 | 0.977 | 0.977 | 0.989 | 0.989 | 0.989 | 0.989 | 0.977 | 0.989 | 0.989 | 0.989 | 0.989 | 0.989 | 0.989 |
| KNN | 0.909 | 0.943 | 0.966 | 0.966 | 0.966 | 0.989 | 0.977 | 0.977 | 0.977 | 0.977 | 0.966 | 0.977 | 0.977 | 0.977 | 0.989 |
| Ensemble3 | 0.909 | 0.886 | 0.977 | 0.989 | 0.977 | 0.989 | 0.989 | 0.989 | 0.966 | 0.966 | 0.966 | 0.966 | 0.977 | 0.966 | 0.977 |
| Ensemble4 | 0.909 | 0.886 | 0.977 | 0.989 | 0.977 | 0.989 | 0.989 | 0.989 | 0.966 | 0.966 | 0.966 | 0.966 | 0.977 | 0.966 | 0.977 |
| Ensemble5 | 0.909 | 0.886 | 0.977 | 0.977 | 0.977 | 0.989 | 0.989 | 0.977 | 0.966 | 0.966 | 0.966 | 0.966 | 0.966 | 0.966 | 0.977 |

TABLE 5E

Classification accuracy CMS2 samples with Affymentrix dataset as function of number of genes.

| | 5 | 10 | 20 | 25 | 30 | 40 | 50 | 75 | 100 | 200 | 300 | 400 | 500 | 1000 | 5973 |
|---|---|---|---|---|---|---|---|---|---|---|---|---|---|---|---|
| wSVM | 0.88 | 0.875 | 0.936 | 0.941 | 0.949 | 0.939 | 0.946 | 0.949 | 0.949 | 0.952 | 0.962 | 0.954 | 0.964 | 0.964 | 0.962 |
| SVM | 0.855 | 0.883 | 0.929 | 0.946 | 0.944 | 0.959 | 0.962 | 0.969 | 0.952 | 0.969 | 0.964 | 0.972 | 0.967 | 0.969 | 0.964 |
| DWD | 0.765 | 0.804 | 0.906 | 0.901 | 0.893 | 0.908 | 0.916 | 0.929 | 0.921 | 0.929 | 0.934 | 0.929 | 0.944 | 0.949 | 0.952 |
| glmnet | 0.88 | 0.878 | 0.931 | 0.936 | 0.936 | 0.936 | 0.949 | 0.962 | 0.962 | 0.967 | 0.954 | 0.964 | 0.964 | 0.972 | 0.974 |
| PC-LDA | 0.878 | 0.885 | 0.946 | 0.954 | 0.954 | 0.962 | 0.954 | 0.959 | 0.977 | 0.974 | 0.972 | 0.974 | 0.974 | 0.977 | 0.974 |
| PC-QDA | 0.906 | 0.878 | 0.926 | 0.931 | 0.959 | 0.954 | 0.959 | 0.964 | 0.957 | 0.962 | 0.962 | 0.962 | 0.969 | 0.969 | 0.949 |
| RandomForest | 0.849 | 0.898 | 0.936 | 0.946 | 0.957 | 0.964 | 0.959 | 0.964 | 0.959 | 0.962 | 0.962 | 0.962 | 0.962 | 0.959 | 0.957 |
| RotForest | 0.893 | 0.913 | 0.934 | 0.944 | 0.957 | 0.952 | 0.959 | 0.967 | 0.964 | 0.957 | 0.969 | 0.959 | 0.957 | 0.967 | 0.959 |
| KNN | 0.872 | 0.901 | 0.959 | 0.964 | 0.972 | 0.977 | 0.982 | 0.967 | 0.972 | 0.977 | 0.982 | 0.987 | 0.987 | 0.98 | 0.974 |
| Ensemble3 | 0.832 | 0.867 | 0.944 | 0.962 | 0.964 | 0.969 | 0.964 | 0.967 | 0.974 | 0.98 | 0.977 | 0.98 | 0.982 | 0.98 | 0.972 |
| Ensemble4 | 0.834 | 0.867 | 0.944 | 0.962 | 0.964 | 0.969 | 0.964 | 0.967 | 0.974 | 0.98 | 0.977 | 0.98 | 0.982 | 0.98 | 0.972 |
| Ensemble5 | 0.86 | 0.872 | 0.946 | 0.959 | 0.962 | 0.964 | 0.972 | 0.974 | 0.972 | 0.977 | 0.98 | 0.98 | 0.982 | 0.98 | 0.977 |

TABLE 6A

Classification accuracy of CMS 3 samples on training data set V1 using 4-fold cross validation as function of number of genes.

| | 5 | 10 | 20 | 25 | 30 | 40 | 50 | 75 | 100 | 200 | 300 | 400 | 500 | 1000 | 5973 |
|---|---|---|---|---|---|---|---|---|---|---|---|---|---|---|---|
| wSVM | 0.716 | 0.705 | 0.903 | 0.915 | 0.915 | 0.909 | 0.909 | 0.926 | 0.932 | 0.949 | 0.943 | 0.915 | 0.926 | 0.92 | 0.909 |
| SVM | 0.466 | 0.585 | 0.881 | 0.869 | 0.869 | 0.903 | 0.898 | 0.898 | 0.903 | 0.909 | 0.915 | 0.915 | 0.92 | 0.915 | 0.875 |
| DWD | 0.648 | 0.693 | 0.903 | 0.898 | 0.92 | 0.915 | 0.903 | 0.92 | 0.932 | 0.955 | 0.943 | 0.949 | 0.938 | 0.932 | 0.915 |
| glmnet | 0.426 | 0.591 | 0.886 | 0.852 | 0.886 | 0.869 | 0.881 | 0.886 | 0.886 | 0.898 | 0.903 | 0.915 | 0.898 | 0.881 | 0.892 |
| PC-LDA | 0.443 | 0.58 | 0.784 | 0.807 | 0.847 | 0.864 | 0.875 | 0.892 | 0.852 | 0.875 | 0.864 | 0.858 | 0.869 | 0.869 | 0.807 |
| PC-QDA | 0.489 | 0.597 | 0.847 | 0.841 | 0.875 | 0.886 | 0.864 | 0.892 | 0.886 | 0.886 | 0.892 | 0.869 | 0.903 | 0.875 | 0.835 |
| RandomForest | 0.438 | 0.483 | 0.79 | 0.784 | 0.824 | 0.83 | 0.869 | 0.892 | 0.852 | 0.881 | 0.864 | 0.869 | 0.869 | 0.835 | 0.818 |
| RotForest | 0.472 | 0.472 | 0.773 | 0.784 | 0.79 | 0.818 | 0.795 | 0.835 | 0.841 | 0.886 | 0.858 | 0.886 | 0.881 | 0.881 | 0.852 |
| KNN | 0.432 | 0.534 | 0.778 | 0.801 | 0.801 | 0.835 | 0.881 | 0.864 | 0.909 | 0.903 | 0.881 | 0.864 | 0.892 | 0.864 | 0.699 |
| Ensemble3 | 0.545 | 0.693 | 0.79 | 0.818 | 0.847 | 0.852 | 0.869 | 0.886 | 0.875 | 0.898 | 0.886 | 0.858 | 0.881 | 0.886 | 0.784 |
| Ensemble4 | 0.534 | 0.693 | 0.801 | 0.807 | 0.847 | 0.852 | 0.864 | 0.886 | 0.875 | 0.898 | 0.886 | 0.858 | 0.881 | 0.886 | 0.801 |
| Ensemble5 | 0.562 | 0.642 | 0.824 | 0.824 | 0.852 | 0.858 | 0.881 | 0.892 | 0.881 | 0.886 | 0.886 | 0.875 | 0.892 | 0.881 | 0.835 |

35

TABLE 6B

Classification accuracy of CMS 3 samples on validation data set as function of number of genes.

| V2 | 5 | 10 | 20 | 25 | 30 | 40 | 50 | 75 | 100 | 200 | 300 | 400 | 500 | 1000 | 5973 |
|---|---|---|---|---|---|---|---|---|---|---|---|---|---|---|---|
| wSVM | 0.478 | 0.551 | 0.758 | 0.775 | 0.775 | 0.792 | 0.831 | 0.848 | 0.882 | 0.899 | 0.893 | 0.916 | 0.916 | 0.899 | 0.904 |
| SVM | 0.455 | 0.528 | 0.742 | 0.758 | 0.781 | 0.798 | 0.803 | 0.826 | 0.826 | 0.854 | 0.86 | 0.86 | 0.871 | 0.871 | 0.865 |
| DWD | 0.607 | 0.674 | 0.831 | 0.843 | 0.837 | 0.876 | 0.871 | 0.904 | 0.904 | 0.91 | 0.921 | 0.921 | 0.927 | 0.916 | 0.904 |
| glmnet | 0.393 | 0.545 | 0.758 | 0.781 | 0.826 | 0.792 | 0.826 | 0.815 | 0.843 | 0.854 | 0.854 | 0.837 | 0.86 | 0.831 | 0.837 |
| PC-LDA | 0.416 | 0.522 | 0.702 | 0.708 | 0.736 | 0.747 | 0.787 | 0.815 | 0.831 | 0.82 | 0.809 | 0.826 | 0.843 | 0.826 | 0.736 |
| PC-QDA | 0.416 | 0.528 | 0.713 | 0.736 | 0.747 | 0.781 | 0.781 | 0.831 | 0.82 | 0.826 | 0.82 | 0.837 | 0.854 | 0.848 | 0.792 |
| RandomForest | 0.506 | 0.489 | 0.674 | 0.68 | 0.736 | 0.702 | 0.775 | 0.775 | 0.798 | 0.798 | 0.787 | 0.798 | 0.809 | 0.781 | 0.77 |
| RotForest | 0.382 | 0.365 | 0.596 | 0.612 | 0.635 | 0.669 | 0.691 | 0.725 | 0.781 | 0.809 | 0.787 | 0.831 | 0.837 | 0.792 | 0.792 |
| KNN | 0.416 | 0.5 | 0.691 | 0.697 | 0.702 | 0.753 | 0.792 | 0.815 | 0.82 | 0.792 | 0.787 | 0.826 | 0.815 | 0.809 | 0.68 |
| Ensemble3 | 0.517 | 0.584 | 0.691 | 0.708 | 0.702 | 0.753 | 0.775 | 0.803 | 0.831 | 0.826 | 0.815 | 0.837 | 0.837 | 0.815 | 0.758 |
| Ensemble4 | 0.511 | 0.579 | 0.691 | 0.708 | 0.702 | 0.753 | 0.775 | 0.809 | 0.831 | 0.831 | 0.815 | 0.837 | 0.837 | 0.82 | 0.764 |
| Ensemble5 | 0.5 | 0.567 | 0.697 | 0.708 | 0.725 | 0.764 | 0.781 | 0.803 | 0.843 | 0.854 | 0.826 | 0.837 | 0.843 | 0.837 | 0.775 |

TABLE 6C

Classification accuracy CMS3 samples w.th out of sample prediction set as function of number of genes,

| V2o | 5 | 10 | 20 | 25 | 30 | 40 | 50 | 75 | 100 | 200 | 300 | 400 | 500 | 1000 |
|---|---|---|---|---|---|---|---|---|---|---|---|---|---|---|
| wSVM | 0.32 | 0.48 | 0.72 | 0.76 | 0.68 | 0.76 | 0.8 | 0.96 | 0.96 | 0.92 | 0.92 | 0.92 | 0.92 | 0.92 |
| SVM | 0.4 | 0.48 | 0.72 | 0.76 | 0.72 | 0.76 | 0.76 | 0.88 | 0.88 | 0.92 | 0.92 | 0.92 | 0.92 | 0.92 |
| DWD | 0.6 | 0.72 | 0.88 | 0.88 | 0.8 | 0.88 | 0.96 | 0.96 | 0.96 | 0.96 | 0.96 | 0.92 | 0.96 | 0.96 |
| glmnet | 0.32 | 0.48 | 0.76 | 0.76 | 0.8 | 0.72 | 0.84 | 0.8 | 0.88 | 0.96 | 0.92 | 0.92 | 0.92 | 0.88 |

TABLE 6C-continued

Classification accuracy CMS3 samples w.th out of sample prediction set as function of number of genes,

| V2o | 5 | 10 | 20 | 25 | 30 | 40 | 50 | 75 | 100 | 200 | 300 | 400 | 500 | 1000 |
|---|---|---|---|---|---|---|---|---|---|---|---|---|---|---|
| PC-LDA | 0.44 | 0.52 | 0.68 | 0.68 | 0.76 | 0.76 | 0.88 | 0.8 | 0.84 | 0.84 | 0.84 | 0.88 | 0.88 | 0.84 |
| PC-QDA | 0.28 | 0.44 | 0.64 | 0.64 | 0.76 | 0.76 | 0.76 | 0.84 | 0.84 | 0.84 | 0.8 | 0.84 | 0.88 | 0.84 |
| RandomForest | 0.36 | 0.44 | 0.64 | 0.64 | 0.72 | 0.72 | 0.72 | 0.8 | 0.8 | 0.76 | 0.8 | 0.8 | 0.8 | 0.76 |
| RotForest | 0.28 | 0.28 | 0.4 | 0.48 | 0.6 | 0.6 | 0.6 | 0.72 | 0.76 | 0.84 | 0.8 | 0.84 | 0.84 | 0.8 |
| KNN | 0.28 | 0.32 | 0.6 | 0.68 | 0.64 | 0.68 | 0.72 | 0.8 | 0.8 | 0.76 | 0.84 | 0.88 | 0.84 | 0.84 |
| Ensemble3 | 0.36 | 0.52 | 0.64 | 0.72 | 0.64 | 0.72 | 0.72 | 0.76 | 0.8 | 0.8 | 0.84 | 0.88 | 0.84 | 0.84 |
| Ensemble4 | 0.36 | 0.48 | 0.64 | 0.72 | 0.64 | 0.72 | 0.72 | 0.76 | 0.8 | 0.8 | 0.84 | 0.88 | 0.84 | 0.84 |
| Ensemble5 | 0.4 | 0.48 | 0.64 | 0.68 | 0.68 | 0.72 | 0.76 | 0.8 | 0.8 | 0.84 | 0.84 | 0.88 | 0.84 | 0.84 |

TABLE 6D

Classification accuracy CMS 3 samples with TCGA dataset as function of number of genes.

| TCGA | 5 | 10 | 20 | 25 | 30 | 40 | 50 | 75 | 100 | 200 | 300 | 400 | 500 | 1000 | 5973 |
|---|---|---|---|---|---|---|---|---|---|---|---|---|---|---|---|
| wSVM | 0.385 | 0.462 | 0.731 | 0.731 | 0.769 | 0.846 | 0.885 | 0.846 | 0.846 | 0.923 | 0.885 | 0.923 | 0.923 | 0.885 | 0.885 |
| SVM | 0.423 | 0.462 | 0.731 | 0.769 | 0.769 | 0.846 | 0.846 | 0.846 | 0.769 | 0.846 | 0.846 | 0.846 | 0.846 | 0.808 | 0.846 |
| DWD | 0.577 | 0.577 | 0.769 | 0.808 | 0.846 | 0.885 | 0.885 | 0.885 | 0.885 | 0.846 | 0.923 | 0.923 | 0.923 | 0.885 | 0.846 |
| glmnet | 0.308 | 0.5 | 0.731 | 0.769 | 0.808 | 0.808 | 0.846 | 0.808 | 0.808 | 0.808 | 0.846 | 0.769 | 0.808 | 0.692 | 0.808 |
| PC-LDA | 0.423 | 0.5 | 0.692 | 0.654 | 0.615 | 0.692 | 0.769 | 0.731 | 0.769 | 0.769 | 0.769 | 0.808 | 0.808 | 0.731 | 0.731 |
| PC-QDA | 0.385 | 0.5 | 0.654 | 0.692 | 0.692 | 0.654 | 0.731 | 0.692 | 0.731 | 0.692 | 0.731 | 0.769 | 0.808 | 0.769 | 0.769 |
| RandomForest | 0.462 | 0.462 | 0.731 | 0.654 | 0.654 | 0.692 | 0.769 | 0.769 | 0.769 | 0.808 | 0.808 | 0.846 | 0.846 | 0.846 | 0.846 |
| RotForest | 0.346 | 0.5 | 0.538 | 0.538 | 0.577 | 0.692 | 0.769 | 0.731 | 0.731 | 0.692 | 0.808 | 0.885 | 0.846 | 0.808 | 0.654 |
| KNN | 0.462 | 0.423 | 0.654 | 0.731 | 0.731 | 0.808 | 0.846 | 0.846 | 0.846 | 0.769 | 0.731 | 0.808 | 0.769 | 0.769 | 0.731 |
| Ensemble3 | 0.538 | 0.462 | 0.731 | 0.731 | 0.692 | 0.808 | 0.808 | 0.846 | 0.846 | 0.846 | 0.846 | 0.846 | 0.846 | 0.769 | 0.769 |
| Ensemble4 | 0.5 | 0.462 | 0.731 | 0.731 | 0.692 | 0.808 | 0.808 | 0.846 | 0.846 | 0.846 | 0.846 | 0.846 | 0.846 | 0.769 | 0.769 |
| Ensemble5 | 0.462 | 0.5 | 0.731 | 0.692 | 0.692 | 0.808 | 0.808 | 0.769 | 0.808 | 0.846 | 0.885 | 0.846 | 0.846 | 0.808 | 0.846 |

TABLE 6E

Classification accuracy CMS3 samples with Affymetrix dataset as function of number of genes.

| V2a | 5 | 10 | 20 | 25 | 30 | 40 | 50 | 75 | 100 | 200 | 300 | 400 | 500 | 1000 | 5973 |
|---|---|---|---|---|---|---|---|---|---|---|---|---|---|---|---|
| wSVM | 0.5 | 0.576 | 0.754 | 0.788 | 0.788 | 0.822 | 0.847 | 0.898 | 0.932 | 0.932 | 0.924 | 0.949 | 0.949 | 0.932 | 0.924 |
| SVM | 0.483 | 0.534 | 0.746 | 0.771 | 0.797 | 0.831 | 0.831 | 0.864 | 0.881 | 0.898 | 0.907 | 0.924 | 0.924 | 0.924 | 0.89 |
| DWD | 0.644 | 0.695 | 0.856 | 0.873 | 0.856 | 0.898 | 0.915 | 0.924 | 0.941 | 0.941 | 0.941 | 0.949 | 0.949 | 0.949 | 0.924 |
| glmnet | 0.407 | 0.559 | 0.763 | 0.788 | 0.839 | 0.814 | 0.847 | 0.856 | 0.89 | 0.898 | 0.873 | 0.881 | 0.89 | 0.864 | 0.847 |
| PC-LDA | 0.432 | 0.551 | 0.703 | 0.72 | 0.771 | 0.771 | 0.814 | 0.814 | 0.89 | 0.89 | 0.873 | 0.881 | 0.89 | 0.881 | 0.771 |
| PC-QDA | 0.432 | 0.534 | 0.729 | 0.737 | 0.78 | 0.814 | 0.797 | 0.864 | 0.864 | 0.89 | 0.881 | 0.881 | 0.898 | 0.89 | 0.814 |
| RandomForest | 0.5 | 0.5 | 0.653 | 0.678 | 0.754 | 0.737 | 0.797 | 0.788 | 0.831 | 0.831 | 0.805 | 0.822 | 0.805 | 0.797 | 0.78 |
| RotForest | 0.398 | 0.339 | 0.593 | 0.619 | 0.661 | 0.669 | 0.686 | 0.754 | 0.822 | 0.864 | 0.847 | 0.873 | 0.89 | 0.847 | 0.856 |
| KNN | 0.407 | 0.492 | 0.703 | 0.703 | 0.72 | 0.788 | 0.814 | 0.856 | 0.881 | 0.864 | 0.864 | 0.898 | 0.873 | 0.864 | 0.754 |
| Ensemble3 | 0.508 | 0.61 | 0.686 | 0.712 | 0.72 | 0.771 | 0.788 | 0.822 | 0.873 | 0.873 | 0.847 | 0.89 | 0.873 | 0.856 | 0.788 |
| Ensemble4 | 0.508 | 0.602 | 0.686 | 0.712 | 0.72 | 0.771 | 0.788 | 0.831 | 0.873 | 0.881 | 0.847 | 0.89 | 0.873 | 0.864 | 0.797 |
| Ensemble5 | 0.517 | 0.576 | 0.695 | 0.712 | 0.754 | 0.78 | 0.797 | 0.839 | 0.89 | 0.907 | 0.856 | 0.89 | 0.873 | 0.89 | 0.797 |

TABLE 7A

Classification accuracy of CMS 4 samples on training data set V1 using 4-fold cross validation as function of number of genes.

| V1 | 5 | 10 | 20 | 25 | 30 | 40 | 50 | 75 | 100 | 200 | 300 | 400 | 500 | 1000 | 5973 |
|---|---|---|---|---|---|---|---|---|---|---|---|---|---|---|---|
| wSVM | 0.818 | 0.872 | 0.923 | 0.955 | 0.946 | 0.938 | 0.94 | 0.946 | 0.94 | 0.949 | 0.957 | 0.963 | 0.966 | 0.957 | 0.952 |
| SVM | 0.847 | 0.875 | 0.912 | 0.923 | 0.929 | 0.92 | 0.92 | 0.943 | 0.935 | 0.952 | 0.943 | 0.946 | 0.952 | 0.952 | 0.94 |
| DWD | 0.832 | 0.852 | 0.923 | 0.94 | 0.943 | 0.943 | 0.957 | 0.952 | 0.94 | 0.952 | 0.949 | 0.955 | 0.946 | 0.949 | 0.943 |
| glmnet | 0.832 | 0.864 | 0.918 | 0.929 | 0.938 | 0.932 | 0.943 | 0.935 | 0.92 | 0.938 | 0.935 | 0.94 | 0.946 | 0.938 | 0.929 |
| PC-LDA | 0.821 | 0.838 | 0.858 | 0.886 | 0.889 | 0.875 | 0.889 | 0.884 | 0.875 | 0.889 | 0.892 | 0.895 | 0.881 | 0.892 | 0.852 |
| PC-QDA | 0.83 | 0.841 | 0.869 | 0.895 | 0.898 | 0.892 | 0.901 | 0.918 | 0.92 | 0.935 | 0.943 | 0.935 | 0.92 | 0.923 | 0.898 |
| RandomForest | 0.835 | 0.892 | 0.92 | 0.92 | 0.92 | 0.915 | 0.92 | 0.923 | 0.926 | 0.929 | 0.92 | 0.929 | 0.929 | 0.929 | 0.926 |
| RotForest | 0.821 | 0.895 | 0.915 | 0.929 | 0.912 | 0.94 | 0.938 | 0.949 | 0.94 | 0.946 | 0.943 | 0.957 | 0.96 | 0.96 | 0.94 |
| KNN | 0.807 | 0.824 | 0.866 | 0.875 | 0.872 | 0.881 | 0.886 | 0.895 | 0.892 | 0.886 | 0.878 | 0.878 | 0.878 | 0.889 | 0.824 |
| Ensemble3 | 0.83 | 0.858 | 0.884 | 0.903 | 0.903 | 0.901 | 0.92 | 0.906 | 0.901 | 0.926 | 0.92 | 0.906 | 0.906 | 0.932 | 0.878 |

TABLE 7A-continued

Classification accuracy of CMS 4 samples on training data set V1 using 4-fold cross validation as function of number of genes.

| V1 | 5 | 10 | 20 | 25 | 30 | 40 | 50 | 75 | 100 | 200 | 300 | 400 | 500 | 1000 | 5973 |
|---|---|---|---|---|---|---|---|---|---|---|---|---|---|---|---|
| Ensemble4 | 0.832 | 0.861 | 0.884 | 0.906 | 0.903 | 0.903 | 0.92 | 0.909 | 0.903 | 0.926 | 0.92 | 0.906 | 0.906 | 0.932 | 0.878 |
| Ensemble5 | 0.83 | 0.855 | 0.886 | 0.918 | 0.92 | 0.92 | 0.909 | 0.92 | 0.926 | 0.932 | 0.929 | 0.923 | 0.926 | 0.935 | 0.909 |

TABLE 7B

Classification accuracy of CMS 4 samples on validation data set as function of number of genes.

| V2 | 5 | 10 | 20 | 25 | 30 | 40 | 50 | 75 | 100 | 200 | 300 | 400 | 500 | 1000 | 5973 |
|---|---|---|---|---|---|---|---|---|---|---|---|---|---|---|---|
| wSVM | 0.845 | 0.863 | 0.909 | 0.927 | 0.942 | 0.944 | 0.95 | 0.936 | 0.947 | 0.959 | 0.968 | 0.971 | 0.971 | 0.977 | 0.977 |
| SVM | 0.857 | 0.871 | 0.906 | 0.93 | 0.933 | 0.944 | 0.95 | 0.947 | 0.956 | 0.956 | 0.95 | 0.968 | 0.977 | 0.974 | 0.965 |
| DWD | 0.868 | 0.883 | 0.901 | 0.936 | 0.927 | 0.942 | 0.953 | 0.947 | 0.953 | 0.965 | 0.956 | 0.956 | 0.95 | 0.956 | 0.968 |
| glmnet | 0.845 | 0.86 | 0.901 | 0.93 | 0.924 | 0.924 | 0.942 | 0.924 | 0.933 | 0.924 | 0.944 | 0.936 | 0.93 | 0.936 | 0.942 |
| PC-LDA | 0.822 | 0.825 | 0.848 | 0.889 | 0.898 | 0.895 | 0.898 | 0.892 | 0.901 | 0.912 | 0.906 | 0.904 | 0.906 | 0.901 | 0.909 |
| PC-QDA | 0.854 | 0.857 | 0.868 | 0.883 | 0.898 | 0.906 | 0.933 | 0.927 | 0.924 | 0.95 | 0.947 | 0.944 | 0.944 | 0.924 | 0.921 |
| RandomForest | 0.854 | 0.898 | 0.904 | 0.927 | 0.927 | 0.924 | 0.921 | 0.93 | 0.927 | 0.936 | 0.942 | 0.939 | 0.944 | 0.944 | 0.942 |
| RotForest | 0.845 | 0.868 | 0.895 | 0.915 | 0.921 | 0.933 | 0.933 | 0.942 | 0.936 | 0.959 | 0.956 | 0.959 | 0.962 | 0.965 | 0.939 |
| KNN | 0.833 | 0.836 | 0.863 | 0.901 | 0.88 | 0.871 | 0.895 | 0.909 | 0.909 | 0.906 | 0.918 | 0.933 | 0.936 | 0.936 | 0.877 |
| Ensemble3 | 0.857 | 0.86 | 0.868 | 0.909 | 0.904 | 0.892 | 0.924 | 0.912 | 0.927 | 0.927 | 0.93 | 0.939 | 0.944 | 0.944 | 0.906 |
| Ensemble4 | 0.857 | 0.863 | 0.868 | 0.912 | 0.904 | 0.892 | 0.924 | 0.912 | 0.927 | 0.93 | 0.936 | 0.942 | 0.944 | 0.944 | 0.906 |
| Ensemble5 | 0.851 | 0.86 | 0.871 | 0.901 | 0.912 | 0.93 | 0.921 | 0.924 | 0.933 | 0.942 | 0.936 | 0.944 | 0.947 | 0.939 | 0.944 |

TABLE 7C

Classification accuracy CMS 4 samples with out of sample prediction set as function of number of genes.

| V2o | 5 | 10 | 20 | 25 | 30 | 40 | 50 | 75 | 100 | 200 | 300 | 400 | 500 | 1000 | 5973 |
|---|---|---|---|---|---|---|---|---|---|---|---|---|---|---|---|
| wSVM | 0.75 | 0.776 | 0.868 | 0.908 | 0.895 | 0.908 | 0.934 | 0.934 | 0.947 | 0.934 | 0.947 | 0.961 | 0.974 | 0.974 | 0.987 |
| SVM | 0.75 | 0.75 | 0.855 | 0.868 | 0.895 | 0.934 | 0.961 | 0.947 | 0.947 | 0.934 | 0.934 | 0.961 | 0.987 | 0.987 | 0.987 |
| DWD | 0.776 | 0.776 | 0.829 | 0.882 | 0.882 | 0.934 | 0.947 | 0.934 | 0.947 | 0.947 | 0.947 | 0.934 | 0.921 | 0.934 | 0.974 |
| glmnet | 0.75 | 0.763 | 0.842 | 0.882 | 0.895 | 0.868 | 0.934 | 0.868 | 0.882 | 0.882 | 0.921 | 0.908 | 0.868 | 0.908 | 0.921 |
| PC-LDA | 0.724 | 0.697 | 0.816 | 0.882 | 0.895 | 0.895 | 0.855 | 0.868 | 0.868 | 0.895 | 0.868 | 0.868 | 0.895 | 0.882 | 0.882 |
| PC-QDA | 0.737 | 0.737 | 0.803 | 0.842 | 0.895 | 0.868 | 0.868 | 0.882 | 0.895 | 0.934 | 0.921 | 0.934 | 0.921 | 0.908 | 0.895 |
| RandomForest | 0.776 | 0.816 | 0.816 | 0.895 | 0.882 | 0.895 | 0.842 | 0.868 | 0.855 | 0.882 | 0.908 | 0.868 | 0.895 | 0.908 | 0.895 |
| RotForest | 0.737 | 0.776 | 0.868 | 0.908 | 0.895 | 0.908 | 0.908 | 0.934 | 0.921 | 0.934 | 0.934 | 0.934 | 0.947 | 0.947 | 0.908 |
| KNN | 0.737 | 0.75 | 0.803 | 0.934 | 0.908 | 0.895 | 0.895 | 0.921 | 0.895 | 0.882 | 0.908 | 0.908 | 0.934 | 0.921 | 0.842 |
| Ensemble3 | 0.75 | 0.776 | 0.816 | 0.921 | 0.908 | 0.895 | 0.882 | 0.895 | 0.882 | 0.882 | 0.895 | 0.895 | 0.934 | 0.921 | 0.882 |
| Ensemble4 | 0.75 | 0.776 | 0.816 | 0.934 | 0.908 | 0.895 | 0.882 | 0.895 | 0.882 | 0.882 | 0.908 | 0.908 | 0.934 | 0.921 | 0.882 |
| Ensemble5 | 0.75 | 0.75 | 0.816 | 0.921 | 0.908 | 0.921 | 0.868 | 0.882 | 0.908 | 0.908 | 0.908 | 0.921 | 0.934 | 0.921 | 0.921 |

TABLE 7D

Classification accuracy CMS 3 samples with TCGA dataset as function of number of genes.

| TCGA | 5 | 10 | 20 | 25 | 30 | 40 | 50 | 75 | 100 | 200 | 300 | 400 | 500 | 1000 | 5973 |
|---|---|---|---|---|---|---|---|---|---|---|---|---|---|---|---|
| wSVM | 0.826 | 0.848 | 0.913 | 0.891 | 0.935 | 0.891 | 0.913 | 0.913 | 0.935 | 0.978 | 0.978 | 0.978 | 0.957 | 0.978 | 0.957 |
| SVM | 0.826 | 0.848 | 0.913 | 0.957 | 0.913 | 0.891 | 0.913 | 0.913 | 0.935 | 0.935 | 0.935 | 0.935 | 0.957 | 0.957 | 0.935 |
| DWD | 0.87 | 0.891 | 0.913 | 0.957 | 0.935 | 0.913 | 0.913 | 0.935 | 0.935 | 0.957 | 0.935 | 0.957 | 0.935 | 0.957 | 0.957 |
| glmnet | 0.826 | 0.804 | 0.935 | 0.913 | 0.891 | 0.891 | 0.87 | 0.891 | 0.957 | 0.935 | 0.935 | 0.913 | 0.935 | 0.913 | 0.913 |
| PC-LDA | 0.761 | 0.761 | 0.848 | 0.848 | 0.826 | 0.848 | 0.826 | 0.761 | 0.848 | 0.87 | 0.87 | 0.891 | 0.87 | 0.891 | 0.913 |
| PC-QDA | 0.848 | 0.848 | 0.891 | 0.826 | 0.848 | 0.891 | 0.935 | 0.891 | 0.891 | 0.935 | 0.935 | 0.913 | 0.935 | 0.87 | 0.848 |
| RandomForest | 0.848 | 0.826 | 0.826 | 0.848 | 0.826 | 0.848 | 0.87 | 0.848 | 0.87 | 0.87 | 0.87 | 0.891 | 0.891 | 0.891 | 0.87 |
| RotForest | 0.848 | 0.848 | 0.913 | 0.891 | 0.848 | 0.891 | 0.891 | 0.891 | 0.891 | 0.978 | 0.935 | 0.978 | 0.957 | 0.978 | 0.913 |
| KNN | 0.804 | 0.761 | 0.87 | 0.87 | 0.804 | 0.783 | 0.761 | 0.804 | 0.826 | 0.826 | 0.848 | 0.87 | 0.87 | 0.848 | 0.804 |
| Ensemble3 | 0.848 | 0.826 | 0.848 | 0.848 | 0.848 | 0.826 | 0.848 | 0.783 | 0.87 | 0.87 | 0.891 | 0.913 | 0.891 | 0.891 | 0.848 |
| Ensemble4 | 0.848 | 0.848 | 0.848 | 0.848 | 0.848 | 0.826 | 0.848 | 0.783 | 0.87 | 0.87 | 0.891 | 0.913 | 0.891 | 0.891 | 0.848 |
| Ensemble5 | 0.826 | 0.848 | 0.891 | 0.848 | 0.848 | 0.891 | 0.87 | 0.848 | 0.913 | 0.891 | 0.913 | 0.913 | 0.913 | 0.913 | 0.891 |

TABLE 7E

| | | | | | | | | Classification accuracy of CMS 3 samples with Affymetrix data set as function of number of genes. | | | | | | |
|---|---|---|---|---|---|---|---|---|---|---|---|---|---|---|
| V2a | 5 | 10 | 20 | 25 | 30 | 40 | 50 | 75 | 100 | 200 | 300 | 400 | 500 | 1000 | 5973 |
| wSVM | 0.5 | 0.576 | 0.754 | 0.788 | 0.788 | 0.822 | 0.847 | 0.898 | 0.932 | 0.932 | 0.924 | 0.949 | 0.949 | 0.932 | 0.924 |
| SVM | 0.483 | 0.534 | 0.746 | 0.771 | 0.797 | 0.831 | 0.831 | 0.864 | 0.881 | 0.898 | 0.907 | 0.924 | 0.924 | 0.924 | 0.89 |
| DWD | 0.644 | 0.695 | 0.856 | 0.873 | 0.856 | 0.898 | 0.915 | 0.924 | 0.941 | 0.941 | 0.941 | 0.949 | 0.949 | 0.949 | 0.924 |
| glmnet | 0.407 | 0.559 | 0.763 | 0.788 | 0.839 | 0.814 | 0.847 | 0.856 | 0.89 | 0.898 | 0.873 | 0.881 | 0.89 | 0.864 | 0.847 |
| PC-LDA | 0.432 | 0.551 | 0.703 | 0.72 | 0.771 | 0.771 | 0.814 | 0.839 | 0.881 | 0.89 | 0.873 | 0.881 | 0.89 | 0.881 | 0.771 |
| PC-QDA | 0.432 | 0.534 | 0.729 | 0.737 | 0.78 | 0.814 | 0.797 | 0.864 | 0.864 | 0.89 | 0.881 | 0.881 | 0.898 | 0.89 | 0.814 |
| RandomForest | 0.5 | 0.5 | 0.653 | 0.678 | 0.754 | 0.737 | 0.797 | 0.788 | 0.831 | 0.831 | 0.805 | 0.822 | 0.805 | 0.797 | 0.78 |
| RotForest | 0.398 | 0.339 | 0.593 | 0.619 | 0.661 | 0.669 | 0.686 | 0.754 | 0.822 | 0.864 | 0.847 | 0.873 | 0.89 | 0.847 | 0.856 |
| KNN | 0.407 | 0.492 | 0.703 | 0.703 | 0.72 | 0.788 | 0.814 | 0.856 | 0.881 | 0.864 | 0.864 | 0.898 | 0.873 | 0.864 | 0.754 |
| Ensemble3 | 0.508 | 0.61 | 0.686 | 0.712 | 0.72 | 0.771 | 0.788 | 0.822 | 0.873 | 0.873 | 0.847 | 0.89 | 0.873 | 0.856 | 0.788 |
| Ensemble4 | 0.508 | 0.602 | 0.686 | 0.712 | 0.72 | 0.771 | 0.788 | 0.831 | 0.873 | 0.881 | 0.847 | 0.89 | 0.873 | 0.864 | 0.797 |
| Ensemble5 | 0.517 | 0.576 | 0.695 | 0.712 | 0.754 | 0.78 | 0.797 | 0.839 | 0.89 | 0.907 | 0.856 | 0.89 | 0.873 | 0.89 | 0.797 |

Comparison of Methods on CRC Data Set, Validation Data Set V2: The wSVM was selected based on the 4-fold CV performance in the training data V1, and its accuracy was assessed on the independent data set V2, plus the subsets to assess out of sample performance (V2o), RNAseq performance (TCGA), and Affymetrix sample performance (V2a). Tables 8A-D present the classification accuracies for these validation data sets for the wSVM for the various model sizes, and also includes for comparison the validation performance of the other methods considered on V1. FIG. 2 plots the 4-group classification accuracies of each method on the full validation data (V2) as a function of the model size.

The wSVM maintained outstanding performance for the validation data set (V2) that is on par with the 4-fold CV results for V1, with similar accuracies for the 5,973 gene model (0.955 for V2 vs. 0.959 for V1), the 500 gene model (0.959 vs. 0.963), the 75 gene model (0.932 vs. 0.950), and the 20 gene model (0.898 vs. 0.920). Once again, a bump in performance was seen for considering models of size smaller than 5,973, and the wSVM along with SVM and DWD appear to be best in the validation data, as well, supporting the choice to focus on the wSVM classifier.

The performance of the wSVM classifier for the out-of-sample subset (V2o), the RNAseq subset (TCGA), and the Affymetrix subset (V2a), were comparable to the overall validation performance (V2), with the 500 gene model having 4-group classification accuracy of 0.967 for V2o, 0.963 for TCGA, and 0.959 for V2a compared with 0.959 for the entire V2 data set. This suggests that the classifier is robust to platform (Affymetrix vs. RNAseq) and has good out-of-sample performance in the context of the CRCSC data sets.

The validation performance also looks good across CMS (see Tables 4A-7E for 4-group classification accuracy in validation data and its subsets). The 500-gene wSVM has classification accuracies of 0.940, 0.972, 0.916, and 0.971 for CMS1-4, respectively.

Tables 8A-D. Classification accuracy on validation data set, the entire set (V2; Table 8A), out-of-sample prediction (V2o; Table 8B). Affymetrix subset (V2a: Table 8C), and TCGA RNAseq subset (TCGA. Table 8D) for various methods as function of number of genes.

TABLE 8A

| V2 | 5 | 10 | 20 | 25 | 30 | 40 | 50 | 75 | 100 | 200 | 300 | 400 | 500 | 1000 | 5973 |
|---|---|---|---|---|---|---|---|---|---|---|---|---|---|---|---|
| wSVM | 0.784 | 0.813 | 0.898 | 0.906 | 0.913 | 0.920 | 0.929 | 0.932 | 0.937 | 0.947 | 0.956 | 0.955 | 0.959 | 0.959 | 0.955 |
| SVM | 0.763 | 0.818 | 0.889 | 0.906 | 0.908 | 0.926 | 0.927 | 0.938 | 0.932 | 0.947 | 0.947 | 0.953 | 0.954 | 0.953 | 0.95 |
| DWD | 0.750 | 0.797 | 0.885 | 0.899 | 0.898 | 0.919 | 0.924 | 0.933 | 0.932 | 0.941 | 0.944 | 0.946 | 0.950 | 0.951 | 0.953 |
| glmnet | 0.763 | 0.812 | 0.885 | 0.902 | 0.907 | 0.911 | 0.926 | 0.923 | 0.924 | 0.929 | 0.934 | 0.929 | 0.932 | 0.934 | 0.94 |
| PC-LDA | 0.761 | 0.805 | 0.876 | 0.891 | 0.894 | 0.902 | 0.907 | 0.914 | 0.927 | 0.929 | 0.927 | 0.934 | 0.938 | 0.932 | 0.918 |
| PC-QDA | 0.780 | 0.809 | 0.874 | 0.885 | 0.898 | 0.912 | 0.920 | 0.926 | 0.922 | 0.934 | 0.933 | 0.938 | 0.941 | 0.932 | 0.91 |
| RandomForest | 0.773 | 0.821 | 0.884 | 0.895 | 0.907 | 0.906 | 0.916 | 0.921 | 0.917 | 0.925 | 0.925 | 0.927 | 0.931 | 0.924 | 0.924 |
| RotForest | 0.769 | 0.802 | 0.869 | 0.883 | 0.897 | 0.901 | 0.91 | 0.919 | 0.926 | 0.936 | 0.941 | 0.944 | 0.939 | 0.94 | 0.928 |
| KNN | 0.769 | 0.814 | 0.878 | 0.889 | 0.888 | 0.9 | 0.913 | 0.918 | 0.916 | 0.912 | 0.92 | 0.929 | 0.927 | 0.921 | 0.865 |
| Ensemble3 | 0.772 | 0.813 | 0.880 | 0.898 | 0.899 | 0.905 | 0.92 | 0.921 | 0.930 | 0.934 | 0.934 | 0.941 | 0.943 | 0.937 | 0.909 |
| Ensemble4 | 0.772 | 0.813 | 0.880 | 0.90 | 0.901 | 0.905 | 0.919 | 0.922 | 0.930 | 0.936 | 0.935 | 0.943 | 0.943 | 0.938 | 0.914 |
| Ensemble5 | 0.777 | 0.813 | 0.882 | 0.898 | 0.904 | 0.916 | 0.922 | 0.926 | 0.932 | 0.943 | 0.941 | 0.946 | 0.947 | 0.942 | 0.935 |

TABLE 8B

| V2o | 5 | 10 | 20 | 25 | 30 | 40 | 50 | 75 | 100 | 200 | 300 | 400 | 500 | 1000 | 5973 |
|---|---|---|---|---|---|---|---|---|---|---|---|---|---|---|---|
| wSVM | 0.749 | 0.782 | 0.874 | 0.887 | 0.891 | 0.904 | 0.912 | 0.941 | 0.946 | 0.937 | 0.958 | 0.958 | 0.967 | 0.962 | 0.958 |
| SVM | 0.736 | 0.778 | 0.858 | 0.887 | 0.895 | 0.921 | 0.921 | 0.950 | 0.929 | 0.954 | 0.954 | 0.967 | 0.971 | 0.967 | 0.962 |
| DWD | 0.720 | 0.782 | 0.858 | 0.887 | 0.883 | 0.912 | 0.929 | 0.929 | 0.925 | 0.941 | 0.954 | 0.946 | 0.954 | 0.958 | 0.967 |
| glmnet | 0.732 | 0.782 | 0.854 | 0.874 | 0.891 | 0.879 | 0.921 | 0.904 | 0.900 | 0.925 | 0.937 | 0.925 | 0.916 | 0.950 | 0.950 |
| PC-LDA | 0.736 | 0.770 | 0.866 | 0.904 | 0.916 | 0.916 | 0.891 | 0.908 | 0.921 | 0.929 | 0.921 | 0.933 | 0.946 | 0.929 | 0.921 |
| PC-QDA | 0.736 | 0.770 | 0.849 | 0.870 | 0.912 | 0.900 | 0.900 | 0.921 | 0.921 | 0.941 | 0.937 | 0.954 | 0.950 | 0.941 | 0.925 |
| RandomForest | 0.745 | 0.791 | 0.866 | 0.895 | 0.900 | 0.908 | 0.900 | 0.921 | 0.916 | 0.921 | 0.937 | 0.929 | 0.933 | 0.933 | 0.929 |
| RotForest | 0.732 | 0.774 | 0.858 | 0.883 | 0.904 | 0.895 | 0.908 | 0.937 | 0.921 | 0.941 | 0.946 | 0.946 | 0.946 | 0.946 | 0.925 |

TABLE 8B-continued

| V2o | 5 | 10 | 20 | 25 | 30 | 40 | 50 | 75 | 100 | 200 | 300 | 400 | 500 | 1000 | 5973 |
|---|---|---|---|---|---|---|---|---|---|---|---|---|---|---|---|
| KNN | 0.728 | 0.774 | 0.854 | 0.895 | 0.900 | 0.900 | 0.908 | 0.908 | 0.912 | 0.895 | 0.921 | 0.929 | 0.929 | 0.925 | 0.845 |
| Ensemble3 | 0.724 | 0.778 | 0.862 | 0.908 | 0.904 | 0.908 | 0.916 | 0.912 | 0.925 | 0.916 | 0.941 | 0.946 | 0.954 | 0.950 | 0.916 |
| Ensemble4 | 0.728 | 0.774 | 0.866 | 0.912 | 0.908 | 0.908 | 0.916 | 0.912 | 0.925 | 0.916 | 0.946 | 0.950 | 0.954 | 0.950 | 0.921 |
| Ensemble5 | 0.749 | 0.770 | 0.866 | 0.908 | 0.912 | 0.912 | 0.912 | 0.916 | 0.925 | 0.929 | 0.946 | 0.954 | 0.954 | 0.950 | 0.950 |

TABLE 8C

| V2a | 5 | 10 | 20 | 25 | 30 | 40 | 50 | 75 | 100 | 200 | 300 | 400 | 500 | 1000 | 5973 |
|---|---|---|---|---|---|---|---|---|---|---|---|---|---|---|---|
| wSVM | 0.793 | 0.822 | 0.898 | 0.911 | 0.913 | 0.922 | 0.930 | 0.943 | 0.941 | 0.944 | 0.959 | 0.955 | 0.959 | 0.959 | 0.958 |
| SVM | 0.773 | 0.823 | 0.890 | 0.910 | 0.914 | 0.933 | 0.936 | 0.948 | 0.938 | 0.953 | 0.950 | 0.962 | 0.960 | 0.958 | 0.955 |
| DWD | 0.763 | 0.809 | 0.891 | 0.901 | 0.897 | 0.916 | 0.926 | 0.934 | 0.931 | 0.942 | 0.943 | 0.942 | 0.945 | 0.948 | 0.954 |
| glmnet | 0.775 | 0.820 | 0.885 | 0.903 | 0.907 | 0.913 | 0.929 | 0.935 | 0.930 | 0.938 | 0.940 | 0.938 | 0.936 | 0.946 | 0.943 |
| PC-LDA | 0.769 | 0.815 | 0.879 | 0.897 | 0.905 | 0.909 | 0.906 | 0.922 | 0.932 | 0.938 | 0.932 | 0.938 | 0.941 | 0.936 | 0.925 |
| PC-QDA | 0.787 | 0.812 | 0.879 | 0.888 | 0.909 | 0.920 | 0.925 | 0.930 | 0.924 | 0.939 | 0.939 | 0.944 | 0.945 | 0.939 | 0.920 |
| RandomForest | 0.775 | 0.826 | 0.879 | 0.895 | 0.914 | 0.910 | 0.916 | 0.926 | 0.924 | 0.930 | 0.931 | 0.930 | 0.929 | 0.926 | 0.927 |
| RotForest | 0.771 | 0.804 | 0.870 | 0.885 | 0.903 | 0.902 | 0.912 | 0.927 | 0.930 | 0.938 | 0.945 | 0.942 | 0.936 | 0.941 | 0.933 |
| KNN | 0.774 | 0.820 | 0.885 | 0.898 | 0.900 | 0.914 | 0.926 | 0.931 | 0.929 | 0.928 | 0.935 | 0.939 | 0.936 | 0.932 | 0.888 |
| Ensemble3 | 0.775 | 0.822 | 0.881 | 0.902 | 0.907 | 0.911 | 0.924 | 0.930 | 0.936 | 0.943 | 0.945 | 0.947 | 0.948 | 0.947 | 0.920 |
| Ensemble4 | 0.776 | 0.821 | 0.882 | 0.904 | 0.910 | 0.911 | 0.924 | 0.931 | 0.936 | 0.945 | 0.946 | 0.949 | 0.948 | 0.949 | 0.924 |
| Ensemble5 | 0.784 | 0.818 | 0.882 | 0.903 | 0.912 | 0.917 | 0.927 | 0.936 | 0.939 | 0.950 | 0.945 | 0.953 | 0.952 | 0.952 | 0.940 |

TABLE 8D

| TCGA | 5 | 10 | 20 | 25 | 30 | 40 | 50 | 75 | 100 | 200 | 300 | 400 | 500 | 1000 | 5973 |
|---|---|---|---|---|---|---|---|---|---|---|---|---|---|---|---|
| wSVM | 0.820 | 0.820 | 0.926 | 0.926 | 0.947 | 0.947 | 0.947 | 0.947 | 0.947 | 0.968 | 0.958 | 0.963 | 0.963 | 0.968 | 0.958 |
| SVM | 0.804 | 0.841 | 0.921 | 0.942 | 0.931 | 0.942 | 0.937 | 0.947 | 0.937 | 0.947 | 0.952 | 0.952 | 0.952 | 0.952 | 0.952 |
| DWD | 0.794 | 0.794 | 0.915 | 0.937 | 0.947 | 0.952 | 0.947 | 0.952 | 0.952 | 0.947 | 0.947 | 0.963 | 0.958 | 0.963 | 0.958 |
| glmnet | 0.799 | 0.810 | 0.931 | 0.931 | 0.937 | 0.942 | 0.931 | 0.926 | 0.942 | 0.931 | 0.937 | 0.921 | 0.926 | 0.905 | 0.942 |
| PC-LDA | 0.810 | 0.825 | 0.899 | 0.910 | 0.884 | 0.915 | 0.921 | 0.899 | 0.926 | 0.931 | 0.937 | 0.942 | 0.942 | 0.937 | 0.926 |
| PC-QDA | 0.825 | 0.852 | 0.910 | 0.894 | 0.905 | 0.910 | 0.937 | 0.921 | 0.926 | 0.926 | 0.931 | 0.931 | 0.937 | 0.915 | 0.894 |
| RandomForest | 0.831 | 0.831 | 0.910 | 0.905 | 0.899 | 0.915 | 0.931 | 0.921 | 0.915 | 0.921 | 0.915 | 0.926 | 0.926 | 0.921 | 0.915 |
| RotForest | 0.836 | 0.831 | 0.899 | 0.899 | 0.899 | 0.926 | 0.937 | 0.931 | 0.926 | 0.942 | 0.947 | 0.974 | 0.963 | 0.963 | 0.921 |
| KNN | 0.804 | 0.825 | 0.899 | 0.91 | 0.889 | 0.899 | 0.905 | 0.915 | 0.915 | 0.899 | 0.905 | 0.921 | 0.921 | 0.910 | 0.889 |
| Ensemble3 | 0.836 | 0.815 | 0.915 | 0.921 | 0.910 | 0.926 | 0.931 | 0.921 | 0.931 | 0.931 | 0.926 | 0.937 | 0.937 | 0.915 | 0.915 |
| Ensemble4 | 0.831 | 0.820 | 0.915 | 0.921 | 0.910 | 0.926 | 0.931 | 0.921 | 0.931 | 0.931 | 0.926 | 0.937 | 0.937 | 0.915 | 0.915 |
| Ensemble5 | 0.820 | 0.825 | 0.926 | 0.910 | 0.910 | 0.942 | 0.937 | 0.921 | 0.937 | 0.937 | 0.947 | 0.942 | 0.937 | 0.931 | 0.937 |

Characterizing Performance of 472-gene wSVM Classifier: As described in the methods, the wSVM classifier with 472 genes was chosen to move forward in the context of FFPE samples using the Nanostring platform. This classifier yielded an overall 96.3% classification accuracy in the Affymetrix subset of V2, with 96.6%, 96.7%, 93.2%, and 97.1% accuracy for CMS1, CMS2, CMS3, and CMS4, respectively, in this subset. The CMS structure in this gene set is remarkably persistent, being highly consistent in the training (V1) and validation (V2ap, Affymetrix subset with fRMA probe-level data) data sets (see heat maps in FIG. 1).

Comparison with classifiers in Guinney et al. (2015): Guinney et al. (2015) presented two CMS classifiers: a random forest classifier (RF) using 5,973 genes and a "single sample" classifier (SSP) based on nearest centroid predictor applied using 693 genes. The paper reported classification results for a set of 3,104 samples with "gold standard" consensus CMS class, but these included both training and validation samples and are based on the approach of not forcing a single CMS call for each samples, but only providing classifications for samples with high confidence, defined as posterior probability>0.50 for RF and high correlation (>0.15) with nearest centroid and correlation much less (at least 0.06) for the next closest centroid for SSP, respectively. This criteria left 429/3104 "undetermined" for RF and 666/3104 "undetermined" for SSP. To obtain a more fair comparison with our classifier, our 472-gene wSVM classifier was compared to RF and SSP on the validation data set V2 containing 1,329 samples in two ways: (1) forcing CMS calls on all samples for each method, and (2) calling CMS only for samples with "high confidence," using the criteria in Guinney et al. (2015) for RF and SSP, and maximum class probability $\alpha_i > 0.80$ for the wSVM. Results are presented in Table 9. The wSVM yielded higher classification accuracy than the RF or SSP when forcing CMS calls for all samples. When only calling CMS when confidence is high, the wSVM classifies slightly more samples with high confidence (1186/1329=0.892 vs. 1177/1329=0.886 for RF and 1148/1329=0.864 for SSP) yet also has higher classification accuracy (0.981 vs. 0.968 for RF and 0.970 for SSP). Note that the RF and SSP were trained using all data (including V1 and V2), while our wSVM was only trained on V1, so these V2 results are technically independent validation samples for the wSVM but not RF and SSP. Altogether, the wSVM, although using fewer genes, yields improved classification accuracy relative to the RF and SSP in Guinney et al. (2015) for the CRCSC validation data set V2.

TABLE 9

Comparison of Classifiers. Comparison of random forest (RF) and single sample predictors (SSP) in Guinney et al. (2015) with the wSVM classifier with 472 genes, either forcing a single CMS call for each sample (all calls) or only when classified with high confidence (high probability).

| | | RF | SSP | wSVM |
|---|---|---|---|---|
| All calls | Number of samples | 1329 | 1329 | 1329 |
| | Predictive accuracy | 0.942 | 0.932 | 0.959 |
| High confidence | Number of samples | 1177 | 1148 | 1186 |
| | Proportion classified | 0.886 | 0.864 | 0.892 |
| | Predictive accuracy | 0.968 | 0.970 | 0.981 |

Figure 3:
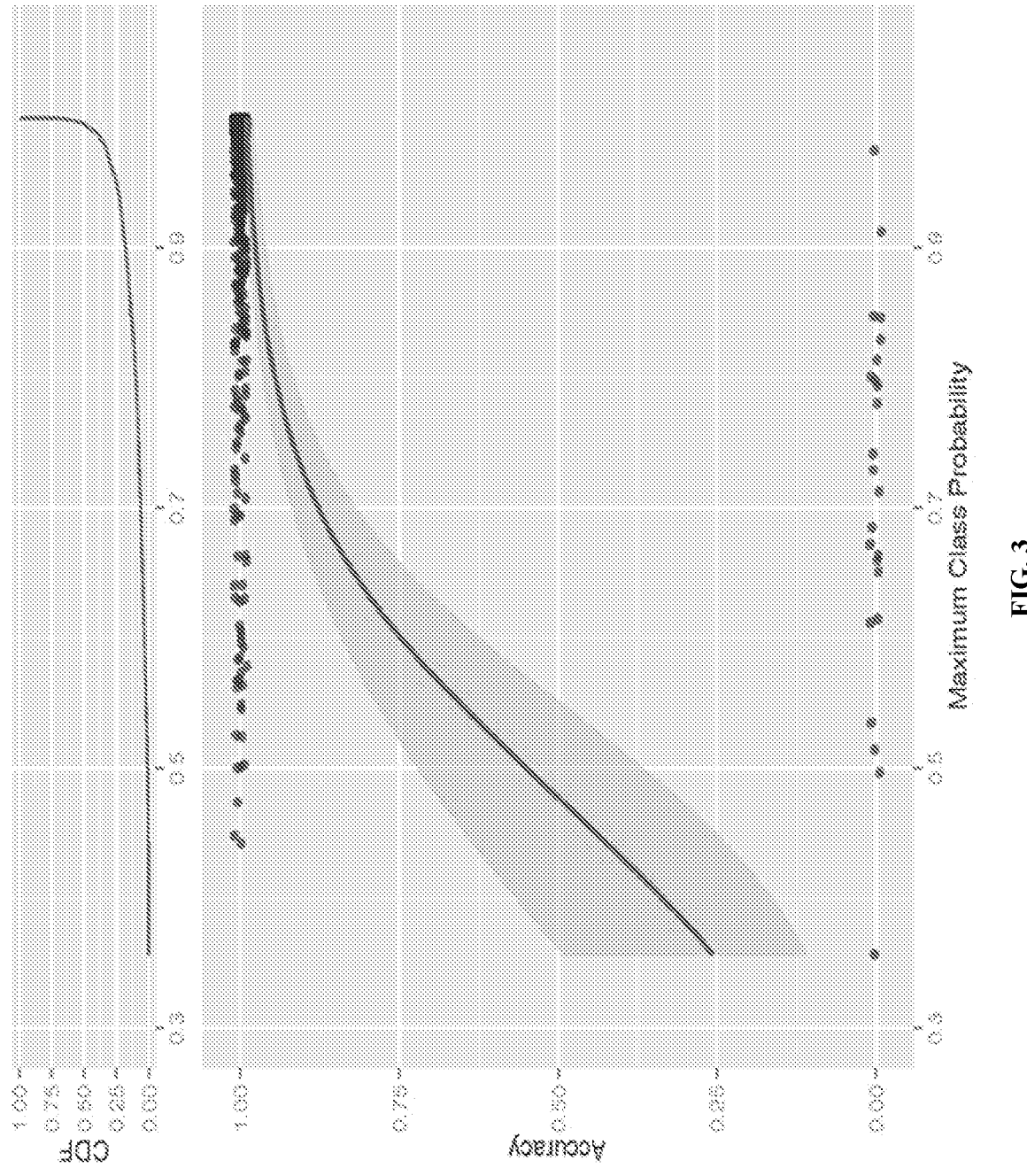
FIG. 3. Classification Confidence of Affymetrix Validation Samples vs. Classification Accuracy of 472-gene wSVM classifier: Distribution of classification confidence $(\alpha_i)$ across 713 validation samples (top), and classification accuracy (1=correct, 0=incorrect) as a function of classification confidence $(\alpha_i)$, with fitted loess curve and 95% confidence interval.

Performance by Confidence: The top panel of FIG. 3 plots the distribution of maximum class probabilities $\alpha_i$ (i.e.

fications (>98.8% accuracy), suggesting that samples classified into a CMS with high confidence by our 472-gene wSVM classifier were virtually always correct in the validation data. Table 10 shows all of the misclassified samples along with the corresponding wSVM class probabilities ($\pi_{ij}$) for each CMS, classification confidence ($\alpha_i$), and an indication of whether this sample could be considered a "CMS mixture" (i.e. $\pi_{ij} > 0.20$ for multiple CMS) and if the "gold standard" was a part of that mixture. Most of the "misclassified samples" had lower classification confidence $\alpha_i$, and many had evidence of being CMS mixtures, with the "gold standard" CMS being a component of the mixtures.

TABLE 10

Validation samples misclassified by 472-gene wSVM classifier: Gold standard CMS, predicted CMS, the class probabilities $\pi_{ij}$ for each CMS (probability for gold standard in bold), and maximum probability $\alpha_i$ for validation samples (V1ap) misclassified by 472-gene wSVM. Note that in many cases, the gold standard CMS, while not highest, has high probability, and in many of these cases there is evidence of a CMS mixture, given multiple CMS with non-negligible (>0.20) probabilities, and if that mixture includes the "gold standard" CMS.

| Gold Standard "Consensus" CMS | Predicted CMS (wSVM-472) | CMS Class probabilities $\pi_{ij}$ | | | | CMS Confidence $\alpha_i =$ max ($\pi_{ij}$) | CMS Mixture multiple $\pi_{ij} > 0.20$ | Include gold standard? |
|---|---|---|---|---|---|---|---|---|
| | | CMS1 | CMS2 | CMS3 | CMS4 | | | |
| CMS4 | CMS1 | 0.36 | 0.27 | 0.02 | 0.35 | 0.36 | yes | yes |
| CMS3 | CMS2 | 0.01 | 0.50 | 0.36 | 0.13 | 0.50 | yes | yes |
| CMS4 | CMS2 | 0.00 | 0.51 | 0.00 | 0.48 | 0.51 | yes | yes |
| CMS2 | CMS1 | 0.53 | 0.40 | 0.05 | 0.01 | 0.53 | yes | yes |
| CMS4 | CMS2 | 0.00 | 0.61 | 0.03 | 0.36 | 0.61 | yes | yes |
| CMS1 | CMS3 | 0.38 | 0.00 | 0.61 | 0.00 | 0.61 | yes | yes |
| CMS4 | CMS1 | 0.65 | 0.00 | 0.00 | 0.35 | 0.65 | yes | yes |
| CMS2 | CMS4 | 0.01 | 0.32 | 0.01 | 0.66 | 0.66 | yes | yes |
| CMS1 | CMS4 | 0.25 | 0.03 | 0.06 | 0.66 | 0.66 | yes | yes |
| CMS3 | CMS2 | 0.00 | 0.67 | 0.33 | 0.00 | 0.67 | yes | yes |
| CMS2 | CMS3 | 0.01 | 0.29 | 0.69 | 0.01 | 0.69 | yes | yes |
| CMS2 | CMS4 | 0.00 | 0.29 | 0.00 | 0.71 | 0.71 | yes | yes |
| CMS4 | CMS2 | 0.00 | 0.73 | 0.00 | 0.27 | 0.73 | yes | yes |
| CMS1 | CMS3 | 0.19 | 0.07 | 0.74 | 0.00 | 0.74 | no | no |
| CMS4 | CMS1 | 0.78 | 0.00 | 0.00 | 0.22 | 0.78 | yes | yes |
| CMS4 | CMS1 | 0.79 | 0.00 | 0.00 | 0.21 | 0.79 | yes | yes |
| CMS3 | CMS1 | 0.80 | 0.09 | 0.11 | 0.00 | 0.80 | no | no |
| CMS3 | CMS1 | 0.80 | 0.01 | 0.19 | 0.00 | 0.80 | no | no |
| CMS2 | CMS4 | 0.00 | 0.18 | 0.00 | 0.81 | 0.81 | no | no |
| CMS2 | CMS3 | 0.03 | 0.13 | 0.83 | 0.02 | 0.83 | no | no |
| CMS3 | CMS2 | 0.03 | 0.85 | 0.13 | 0.00 | 0.85 | no | no |
| CMS1 | CMS3 | 0.15 | 0.00 | 0.85 | 0.00 | 0.85 | no | no |
| CMS3 | CMS1 | 0.91 | 0.00 | 0.08 | 0.00 | 0.91 | no | no |
| CMS1 | CMS3 | 0.02 | 0.00 | 0.97 | 0.01 | 0.97 | no | no | classification confidence) for the 472-gene wSVM on the 713 Affymetrix validation samples with fRMA probe-level values (V2ap), and the bottom panel plots the classification accuracy (1=correct, 0=incorrect) vs. the maximum class probability of the 472-gene wSVM classifier along with a loess fit of the predictive accuracy as a function of a. From the top, 75%-80% of samples had classification confidence of $\alpha_i > 0.90$, and among these there were only two misclassifications (>99.6% accuracy), and >90% of samples had a classification confidence of $\alpha_i > 0.80$, with only 8 misclassi- Performance of 472-gene CRCSC Classifier Based on Single Affymetrix Probe: As mentioned above, the Nanostring assay was designed based on a 472-gene signature, with code sets chosen to match the single Affymetrix probe for each gene best recapitulating the gene-level expressions. After quantifying expression of these genes based on these single probes and applying quantile normalization to these quantifications, the wSVM classifier was retrained for data set V1 to yield a single-probe Affymetrix FF-based classifier, and then assessed for its performance on CRCSC validation data V2ap. Good accuracy was observed in the CRCSC validation data when forcing each sample to have a single CMS class (89.0%), and for the validation samples with high classification confidence ($\pi_i > 90\%$), the accuracy was even better (97.4%). The use of a single probe per gene was sufficient to obtain good CMS classification results in the setting of Affymetrix data on batch-corrected FF samples.

Pilot study of Technical Variability: Table 11 contains the 6-number summary (minimum, maximum, Q25, Q75, mean, median) for percent biological variability (PBV) and coefficient of variation (CV) across the 472 signature genes on the Nanostring array for the 6 FFPE samples run in duplicate on the Nanostring assay. The technical replicate variability was negligible relative to biological variability, with half of the genes with >95.9% biological variability and 75% of the genes having >86.8% biological. The median CV was <0.04, with range of 0.00-0.24 and interquartile range of 0.01-0.07, further demonstrating excellent technical reproducibility within runs.

TABLE 11

Nanostring Pilot Study. Summary of percent of biological variability (PBV) and coefficient of variation (CV) across the 472 signature genes on Nanostring assay from 6 duplicate FFPE samples.

|  | Min | Q25 | Median | Mean | Q75 | Max |
|---|---|---|---|---|---|---|
| PBV | 0 | 86.84 | 95.92 | 87.76 | 98.96 | 100 |
| CV | 0 | 0.013 | 0.038 | 0.049 | 0.072 | 0.241 |

Nanostring, FFPE Classifier: As mentioned above, the strategy for building the Nanostring FFPE-based classifier was to first find a subset of the 472 genes with high FF/FFPE correlation, and then train the wSVM classifier in the CRCSC training data set V1, using quantile normalization over this reduced gene set. The performance of this classifier was validated on the 85 FFPE samples from the CRCSC cohort and the 73 FFPE samples not from the CRCSC cohort after applying sample-specific quantile normalization. Note that since the classifier is trained on the CRCSC training data set V1, and the genes selected not based on classification accuracy but based on FF/FFPE correlation, the subsequent classification accuracies of the 158 FFPE samples serve as validation measurements and are appropriate to directly compute without using cross-validation.

Figure 4A:
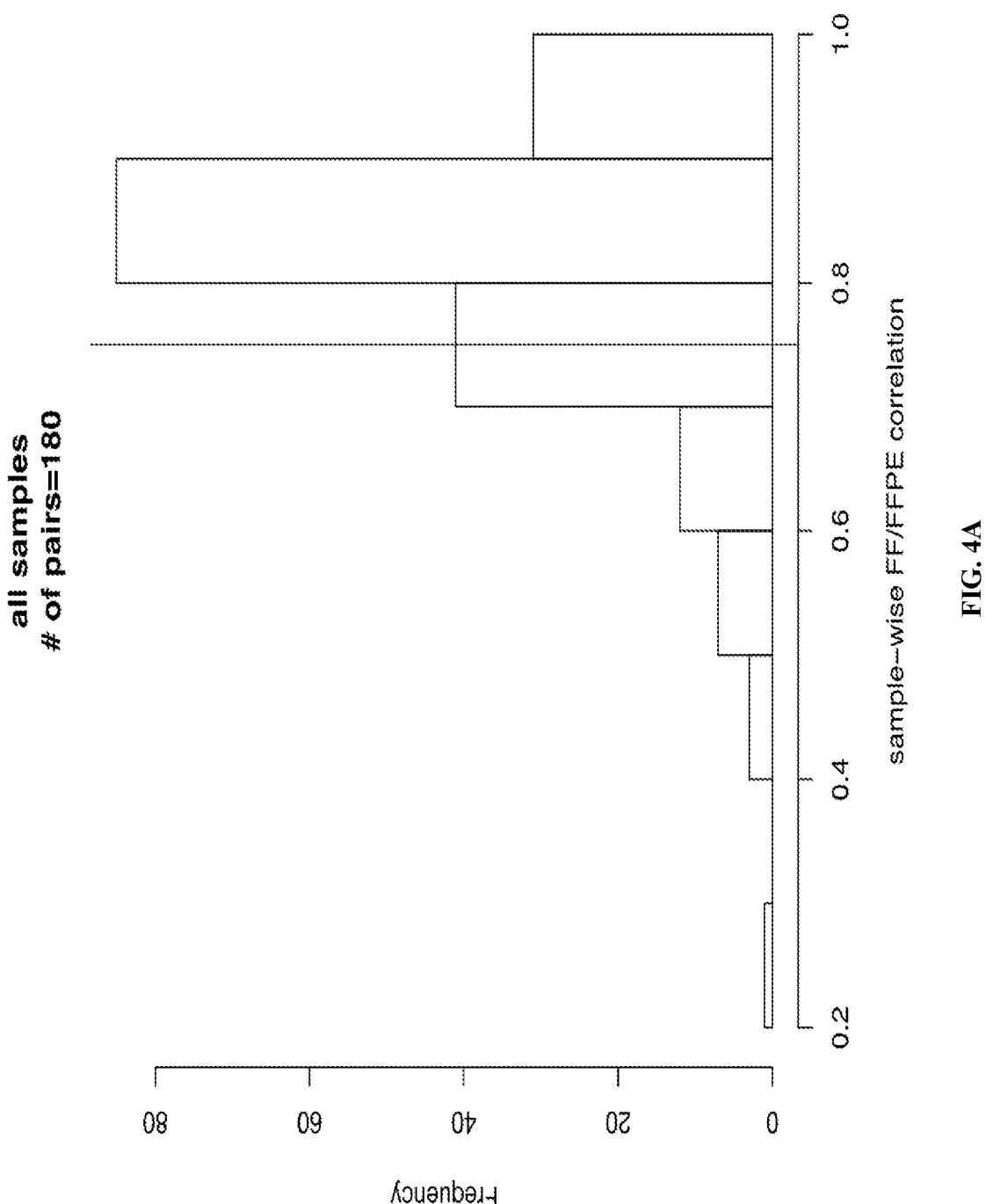
FIGS. 4A&B. Sample-wise and Gene-wise correlation of FF/FFPE paired Samples.
Figure 5A:
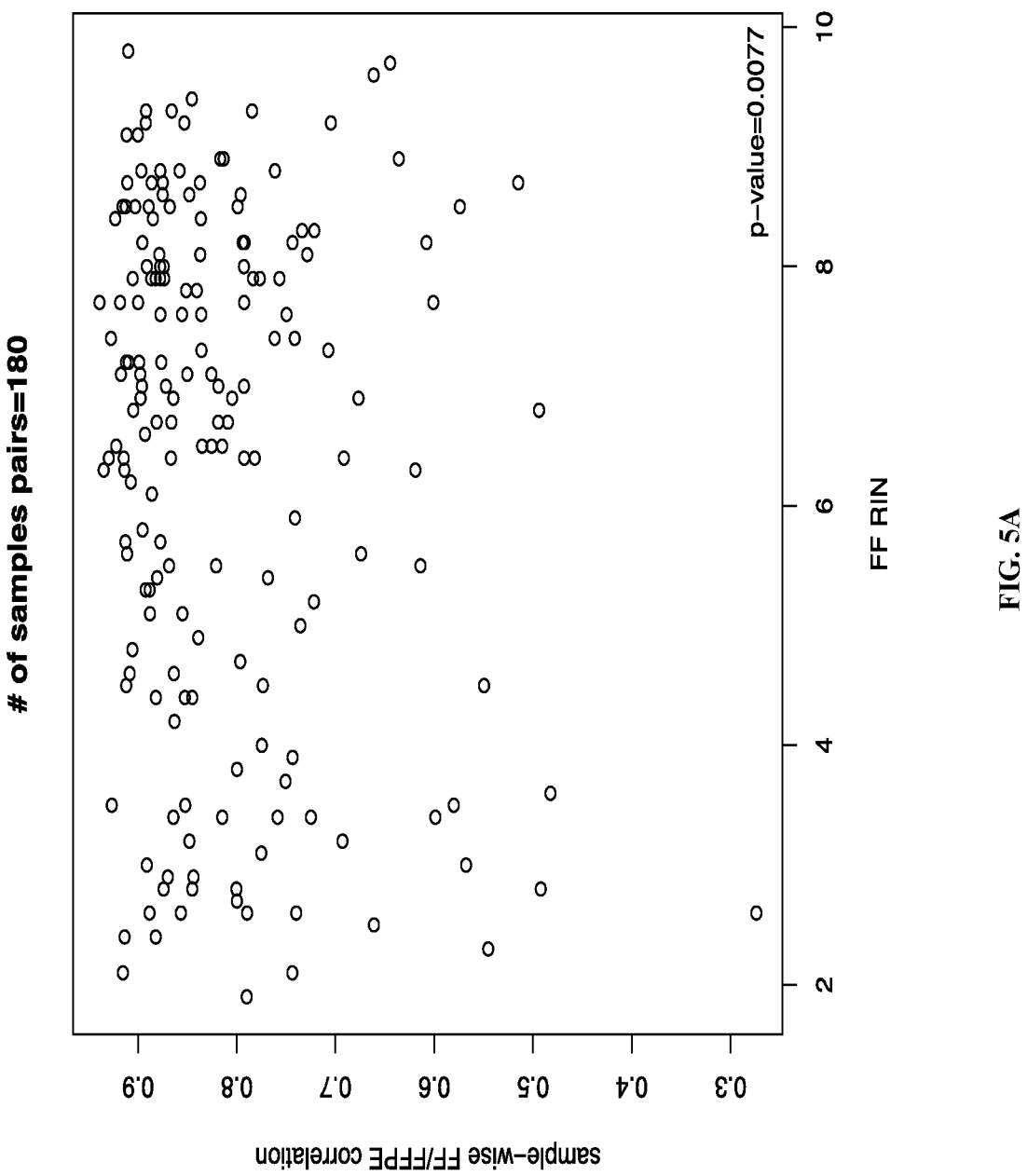
FIGS. 5A&B. Association of Sample-wise FF/FFPE with RNA Quality: Scatterplot of gene-specific Spearman correlation of FF/FFPE vs. RNA quality of FF samples (FIG. 5A, based on RIN) and FFPE samples (FIG. 5B, based on % with 200 nt).
Figure 5B:
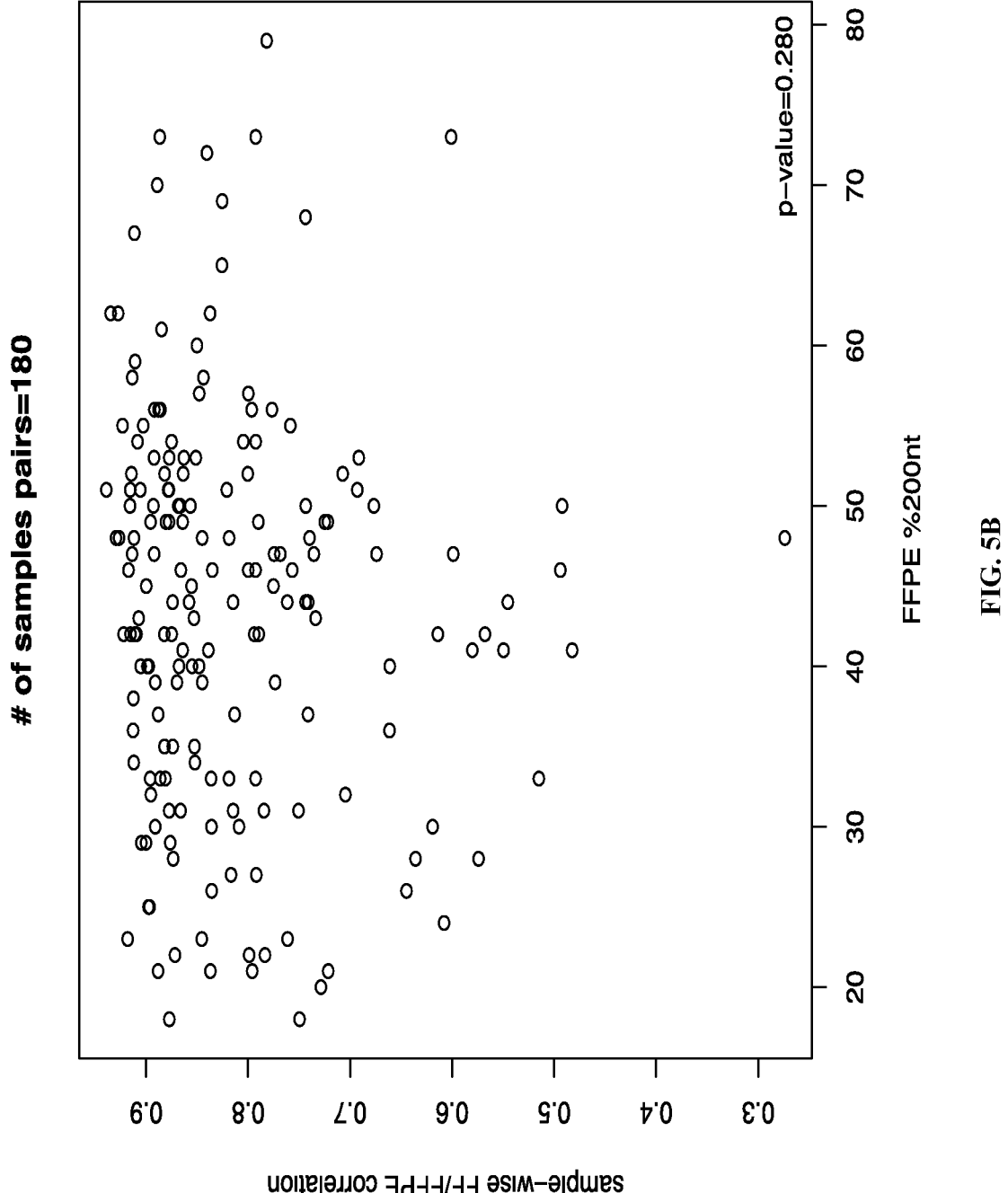

Correlation of FF/FFPE: Sample-specific Spearman correlation of paired FF/FFPE samples was first computed across the 472 CMS genes on the Nanostring assay. FIG. 4A contains a histogram of these correlations, and Table 12 contains a summary of this distribution across all samples, as well as split out by the two batches (85 CRCSC samples and 73 non-CRCSC samples). For most samples, the FF/FFPE correlation is very high, but for a small subset it is lower. Samples with low sample-wise FF/FFPE correlation tended to have poorer RNA quality for their FF samples (p=0.0077), but there was little association with FFPE RNA quality (p=0.28 with %200 nt) (FIGS. 5A&B).

TABLE 12

Summary of sample-wise FF/FFPE Spearman Correlations. Summary of sample-wise paired FF/FFPE correlations across 472 CMS genes for batch 1 containing CRCSC samples (top), batch 2 containing non-CRCSC samples (middle), and all samples (bottom).

|  | Q05 | Q25 | Median | Q75 | Q95 | R > 0.75 |
|---|---|---|---|---|---|---|
| Batch 1, N = 76 (CRCSC) | 0.616 | 0.791 | 0.838 | 0.887 | 0.913 | 0.816 |
| Batch 2, N = 104 (non-CRCSC) | 0.552 | 0.758 | 0.854 | 0.892 | 0.921 | 0.769 |
| All Samples | 0.580 | 0.774 | 0.849 | 0.890 | 0.916 | 0.789 |

Figure 4B:
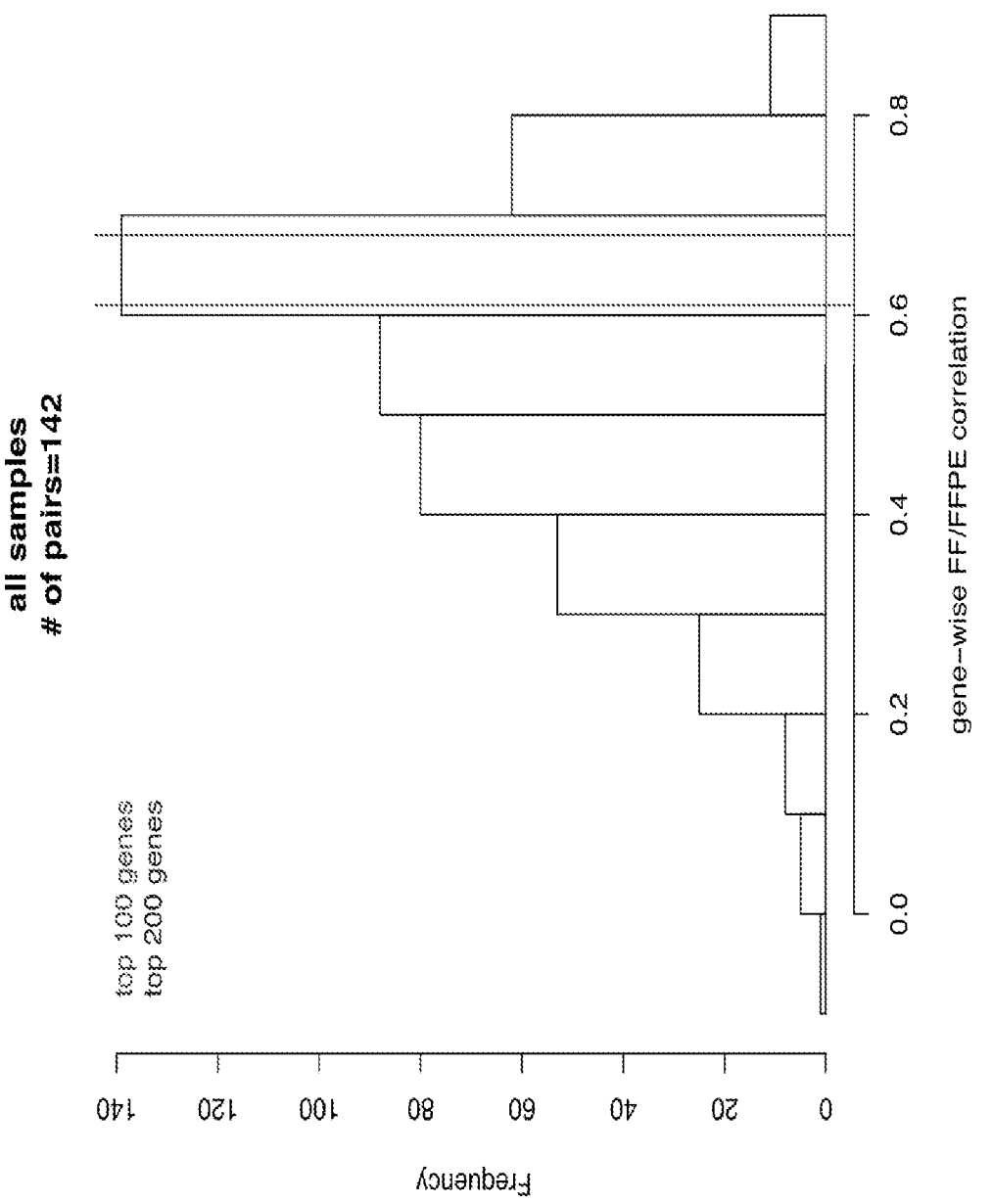
FIG. 4B—Histogram of gene-wise Spearman correlation of paired FF/FFPE values based on samples with sample-wise correlation>0.75, with thresholds to determine the top 100 and top 200 genes indicated by red and blue vertical lines, respectively.
Figure 6:
FIG. 6. Sample-wise and Gene-wise correlation of FF/FFPE paired Samples: Scatterplot of gene-specific Spearman correlation of FF/FFPE computed separately for first batch (CRCSC samples N=85) and second batch (non-CRCSC samples N=73), in terms of FF/FFPE correlation computed across all samples. Note the high level of agreement across batches, that genes with high FF/FFPE correlations for one batch tended to also have high FF/FFPE correlation in the other batch, suggesting high FF/FFPE correlation is a characteristic of the gene/probe set.

To select a subset of genes with high FF/FFPE correlation to use with our CMS classifier, gene-specific Spearman correlations were computed for all 472 CMS genes for paired FF/FFPE samples across all subjects with FF/FFPE correlations of at least 0.75. FIG. 4B contains a histogram of these correlations, and the top rows of Table 13 summarize this distribution, both overall and split out by the two batches. There is a sizable number of genes with reasonably high FF/FFPE correlation (>0.60), and some genes with very low correlation for which the paired FFPE and FF measurements are strongly discordant. The top 100 genes in terms of FF/FFPE correlation were selected, and the bottom rows of Table 13 summarize the distributions for these genes overall and split out by batches. FIG. 6 plots the Spearman correlations of all 472 Nanostring genes in batch 1 vs. batch 2, with the overall top 100 plotted in red, the next 100 plotted in blue, and the rest in black. Note the high level of agreement across batches, that genes with high FF/FFPE correlations for one batch tended to also have high FF/FFPE correlation in the other batch, and genes with very poor agreement in one batch also had poor agreement in the other batch. This suggests that, as hypothesized, high FF/FFPE correlation is a characteristic of the gene/probe set, and thus it is important to focus on subsets of genes with high FF/FFPE correlation in order to accurately classify FFPE samples. The top 100 genes in terms of FF/FFPE correlation were chosen for the FFPE, Nanostring-based classifier.

TABLE 13

Summary of gene-wise FF/FFPE Spearman Correlations. Summary of gene-wise
paired FF/FFPE Spearman Correlations for all 472 genes (top) and top 100 genes (bottom),
computed using samples with sample-wise FF/FFPE correlation of at least 0.75, summarized
by batch and overall.

| Gene Set | | Q05 | Q25 | Median | Q75 | Q95 |
|---|---|---|---|---|---|---|
| All 472 | Batch 1, N = 76 (CRCSC) | 0.204 | 0.367 | 0.510 | 0.613 | 0.717 |
| | Batch 2, N = 104 (non-CRCSC) | 0.290 | 0.505 | 0.630 | 0.730 | 0.825 |
| | All Samples | 0.254 | 0.435 | 0.577 | 0.669 | 0.767 |
| Top 100 | Batch 1, N = 76 (CRCSC) | 0.538 | 0.616 | 0.660 | 0.714 | 0.782 |
| | Batch 2, N = 104 (non-CRCSC) | 0.633 | 0.722 | 0.772 | 0.815 | 0.845 |
| | All Samples | 0.634 | 0.683 | 0.730 | 0.766 | 0.809 |

Nanostring FFPE Classifier Performance: Choosing this subset of 100/472=21.2% of the genes with strong evidence of high FF/FFPE correlation, the wSVM classifier was retrained on the CRCSC training data set V1, doing subject-specific quantile normalization across this set of 100 genes. This 100-gene wSVM classifier was then directly applied to the 158 FFPE samples run on the Nanostring platform after quantile normalization to transform the Nanostring expressions onto the scale of the CRCSC data. Classification accuracy is given in the second columns of Tables 14A-D, comparing with the gold standard CMS for CRCSC subjects (N=85) and comparing to the 472 gene classifier applied to Affymetrix runs on matched FF samples for patients in the non-CRCSC cohort (N=73). In the latter case, the Affymetrix-FF runs were considered to be pseudo-gold standard given the exceptional performance for the 472 gene FF classifier applied to Affymetrix samples reported above.

Figure 7A:
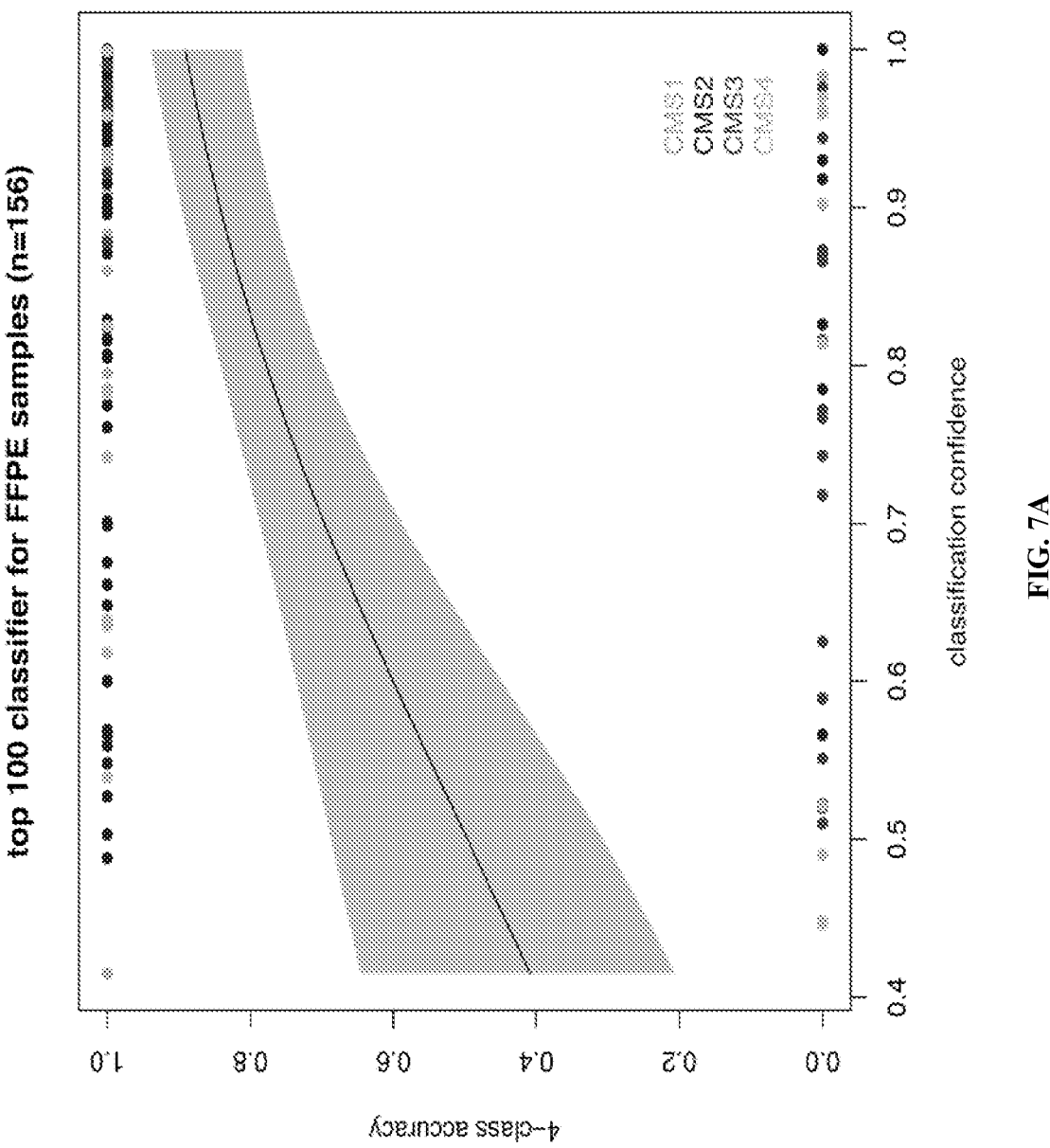
FIGS. 7A-D. Nanostring CMS Classifier Performance. Performance of Nanostring 100 gene CMS classifier applied to FFPE samples (FIGS. 7A&C) and FF samples (FIGS. 7B&D). FIGS. A&B plot 4-class accuracy vs. classification confidence, with the dots marking individual samples either correctly (1.0) or incorrectly (0.0), with color indicating correct CMS. The line contains a generalized additive model (GAM) fit to these data with 95% pointwise confidence bands and demonstrates that samples classified with greater confidence were more likely to be correctly classified. FIGS. C&D plot 4-class accuracy vs. RNA quality, defined as %200 nt (FFPE) or RIN (FF). Note that there is little if any association of CMS accuracy with RNA quality, suggesting that the performance of classifier is robust to RNA quality in this study.
Figure 7B:
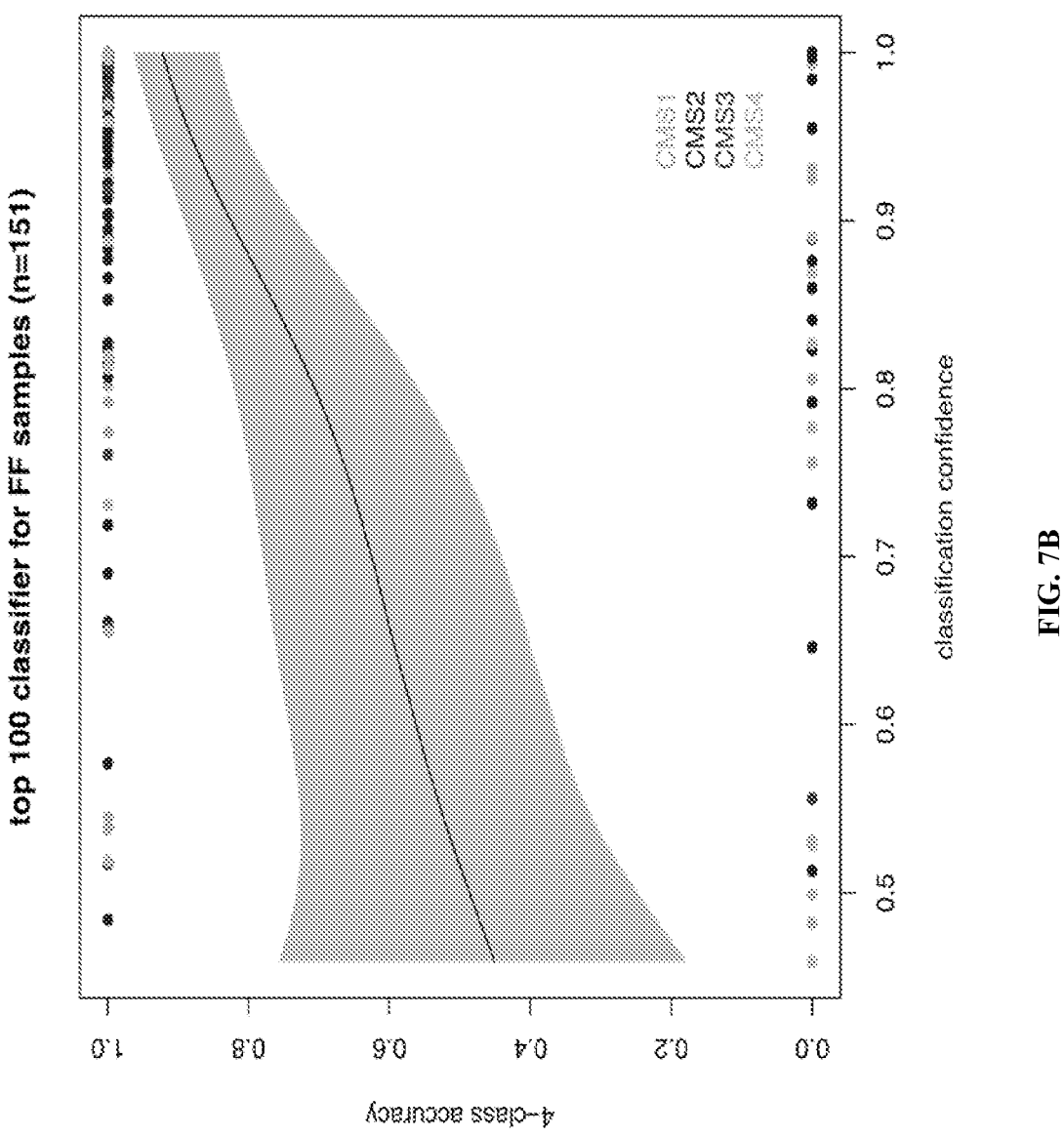
Figure 7C:
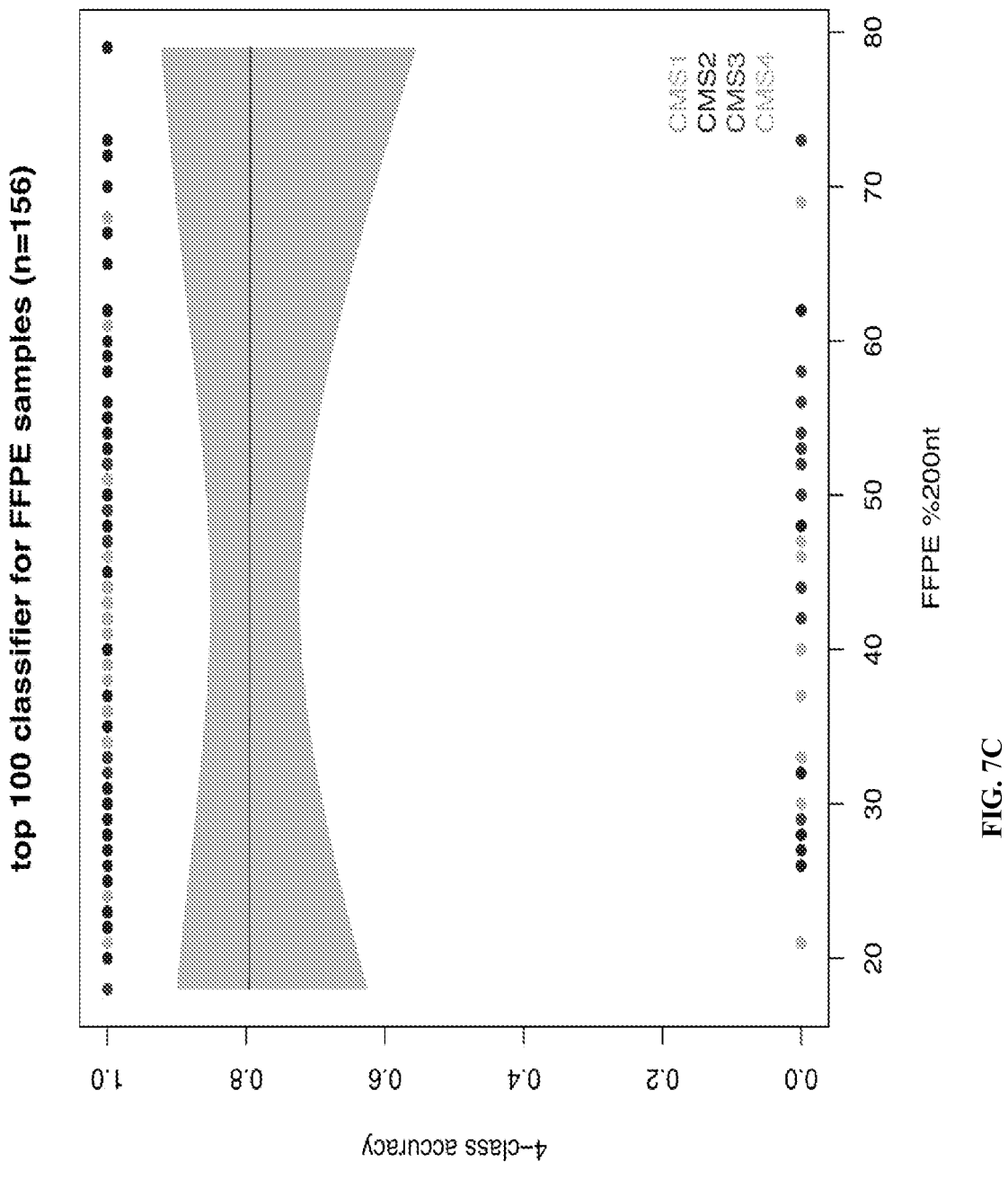
Figure 7D:
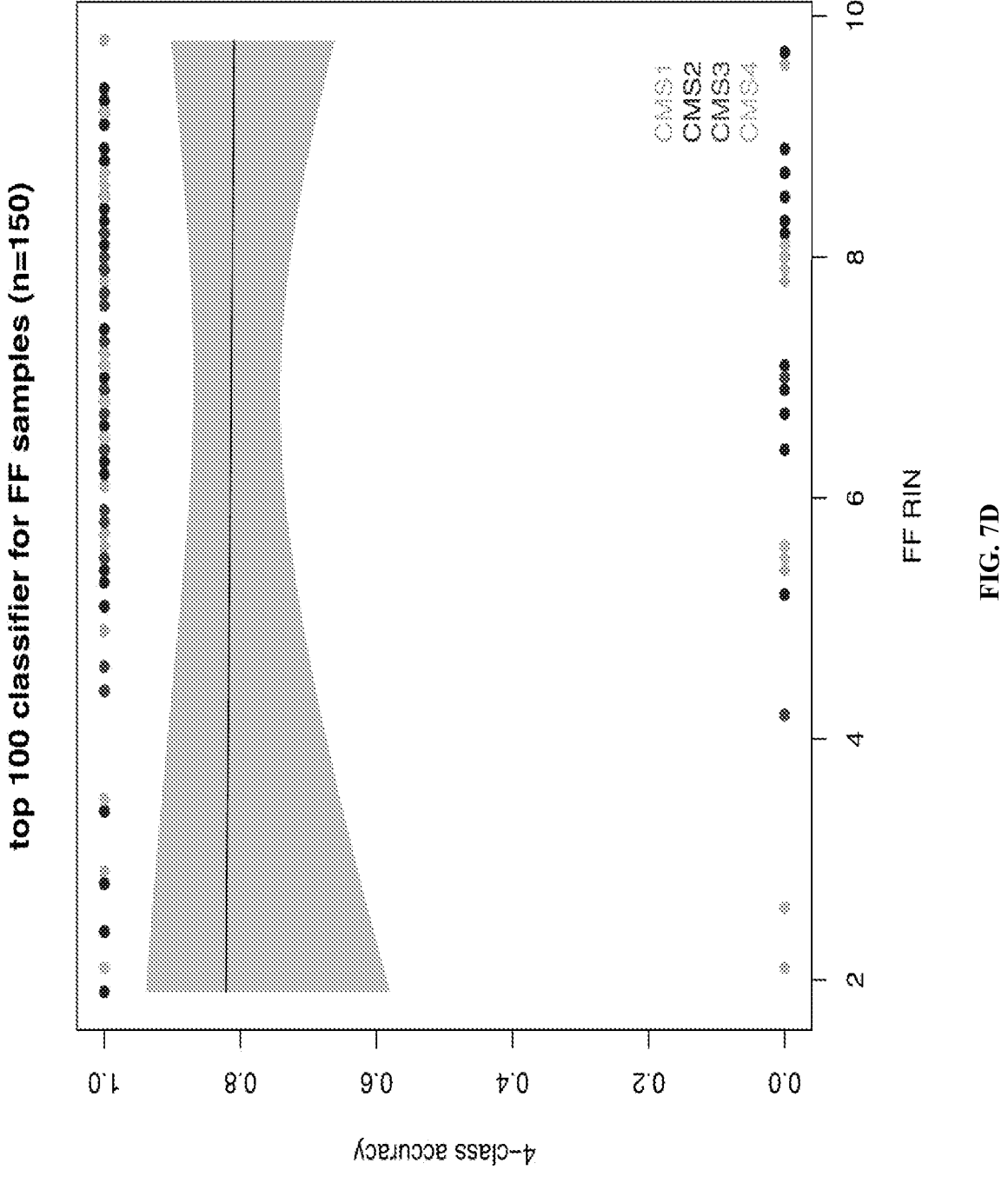

The 100 gene model applied to FFPE samples had 4-group accuracy of 0.797 (126/158), with 0.812 (69/85) for CRCSC samples and 0.781 (57/73) for non-CRCSC samples. For samples classified with high confidence ($\alpha_i > 0.80$ or 0.90), the performance was better with 4-group accuracy of 0.858 and 0.889, respectively. Applied to the FF samples, this 100-gene model had 4-group classification accuracy of 0.804 (123/153), with 0.738 (59/80) for CRCSC samples and 0.877 (64/73) for non-CRCSC samples, with 4-class accuracy of 0.868 and 0.924 for samples classified with high confidence $\pi_i = 0.80$ or 0.90, respectively. FIGS. 7A&B plot the 4-class accuracy vs. confidence level $\pi_i$ for FFPE and FF samples, demonstrating that samples classified with high confidence were more likely to be accurately classified. FIGS. 7C&D plot the 4-class accuracy vs. RNA quality, defined by %200 nt (FFPE) or RIN (FF), demonstrating that there is little if any association of CMS accuracy with RNA quality, suggesting that the performance of classifier is robust to RNA quality in this study. These results together suggest that the 100-gene Nanostring-based classifier performs reasonably well for either FFPE or FF samples.

Tables 14A-D. CMS Classifier Accuracy: 4-class accuracy of CMS classifiers, along with number (proportion) of samples classified to each CMS. The accuracy for the classifier with the top 100 genes was assessed in terms of FF/FFPE correlation for FFPE and FF, computed based on Nanostring measurements for FFPE and FF (Nano FFPE-100, Nano FF-100) and based on Affymetrix measurements for FF in the Affy CRCSC validation data set (V2a, Affy FF-100), and for the full 472 gene classifier applied to FF samples run on the Nanostring platform (Nano FF-472) and FF samples run on Affymetrix in the Affymetrix CRCSC validation data set (Affy FF-472). Performance is summarized overall (Table 14A) and for subsets of samples with high classification confidence (a, >0.50 (Table 14B), 0.80 (Table 14C), or 0.90 (Table 14D)).

TABLE 14A

| No threshold | 4-class accuracy | Distribution of predicted CMS | | | |
|---|---|---|---|---|---|
| | | CMS1 | CMS2 | CMS3 | CMS4 |
| Nano FFPE-100 | 0.797 | 38 (0.24) | 88 (0.56) | 9 (0.06) | 23 (0.15) |
| Nano FF-100 | 0.804 | 34 (0.22) | 72 (0.47) | 31 (0.20) | 16 (0.10) |
| Nano FF-472 | 0.810 | 40 (0.26) | 64 (0.42) | 20 (0.13) | 29 (0.19) |
| Affy FF-100* | 0.892 | 222 (0.17) | 597 (0.45) | 176 (0.13) | 334 (0.25) |
| Affy FF-472* | 0.953 | 232 (0.18) | 572 (0.43) | 173 (0.13) | 352 (0.27) |

TABLE 14B

| P > 0.50 | 4-class accuracy | Distribution of predicted CMS | | | | |
|---|---|---|---|---|---|---|
| | | CMS1 | CMS2 | CMS3 | CMS4 | unclassified |
| Nano FFPE-100 | 0.808 | 36 (0.23) | 85 (0.54) | 8 (0.05) | 22 (0.14) | 5 (0.03) |
| Nano FF-100 | 0.823 | 34 (0.22) | 71 (0.46) | 28 (0.18) | 19 (0.12) | 4 (0.03) |
| Nano FF-472 | 0.819 | 38 (0.25) | 60 (0.40) | 19 (0.13) | 27 (0.18) | 7 (0.05) |
| Affy FF-100* | 0.897 | 218 (0.16) | 590 (0.44) | 172 (0.13) | 329 (0.25) | 20 (0.02) |
| Affy FF-472* | 0.954 | 231 (0.17) | 569 (0.43) | 170 (0.13) | 348 (0.26) | 11 (0.01) |

TABLE 14C

| P > 0.80 | 4-class accuracy | Distribution of predicted CMS | | | | |
|---|---|---|---|---|---|---|
| | | CMS1 | CMS2 | CMS3 | CMS4 | unclassified |
| Nano FFPE-100 | 0.858 | 29 (0.19) | 65 (0.42) | 8 (0.05) | 11 (0.07) | 43 (0.28) |
| Nano FF-100 | 0.868 | 29 (0.19) | 64 (0.42) | 19 (0.13) | 9 (0.06) | 30 (0.20) |
| Nano FF-472 | 0.851 | 38 (0.25) | 60 (0.40) | 19 (0.13) | 27 (0.18) | 7 (0.05) |
| Affy FF-100* | 0.960 | 162 (0.12) | 479 (0.36) | 120 (0.09) | 248 (0.19) | 320 (0.24) |
| Affy FF-472* | 0.982 | 190 (0.14) | 530 (0.40) | 146 (0.11) | 313 (0.24) | 150 (0.11) |

TABLE 14D

| P > 0.90 | 4-class accuracy | Distribution of predicted CMS | | | | |
|---|---|---|---|---|---|---|
| | | CMS1 | CMS2 | CMS3 | CMS4 | unclassified |
| Nano FFPE-100 | 0.889 | 25 (0.16) | 51 (0.33) | 7 (0.04) | 7 (0.04) | 66 (0.42) |
| Nano FF-100 | 0.924 | 20 (0.13) | 51 (0.34) | 16 (0.11) | 5 (0.03) | 59 (0.39) |
| Nano FF-472 | 0.883 | 30 (0.20) | 42 (0.28) | 12 (0.08) | 20 (0.13) | 48 (0.32) |
| Affy FF-100* | 0.980 | 131 (0.10) | 418 (0.31) | 103 (0.08) | 199 (0.15) | 478 (0.36) |
| Affy FF-472* | 0.998 | 169 (0.13) | 498 (0.38) | 123 (0.09) | 288 (0.22) | 251 (0.19) |

Validation of the CMS Assay at the research molecular diagnostic laboratory: The CRC CMS-100 assay was 100% reproducible in predicting a CMS subtype across different runs (12 samples=48 runs), between two laboratory personnel (12 samples) and with different RNA input concentration (n=6). The reproducibility between biopsy and resection was 91% with 15 of 17 patients had same CMS subtype between matched biopsy and resection specimens (Table 15).

TABLE 15

Validation of CMS assay at the research molecular diagnostic laboratory

| | Colon Resection | | | | | | | | | |
|---|---|---|---|---|---|---|---|---|---|---|
| | | | | | Run 5 | | | | | |
| Sample ID | Run 1 | Run 2 | Run 3 | Run 4 | RNA input (500 ng) | RNA input (250 ng) | RNA input (100 ng) | RNA input (50 ng) | Separate Run by Technician #2 | Matching Colonoscopic Biopsy |
| MTDL 207 | 2 | 2 | 2 | 2 | 2 | 2 | 2 | 2 | 2 | 2 |
| MTDL 228 | 1 | 1 | 1 | 1 | 1 | 1 | 1 | 1 | 1 | |
| MTDL 214 | 2 | 2 | 2 | 2 | 2 | 2 | 2 | 2 | 2 | 2 |
| MTDL999 | | | | | 1 | 1 | 1 | 1 | | 1 |
| MTDL202 | | | | | 2 | 2 | 2 | 2 | | 2 |
| MTDL234 | | | | | 2 | 2 | 2 | 2 | | 2 |
| MTDL 1148 | 4 | 4 | 4 | 4 | | | | | 4 | |
| MTDL 232 | 1 | 1 | 1 | 1 | | | | | 1 | |
| MTDL 77 | 2 | 2 | 2 | 2 | | | | | 2 | |
| MTDL 997 | 4 | 4 | 4 | 4 | | | | | 4 | |
| MTDL 192 | 2 | 2 | 2 | 2 | | | | | 2 | 2 |
| MTDL 76 | M | M | M | M | | | | | M | |
| MTDL 411 | 2 | 2 | 2 | 2 | | | | | 2 | 2 |
| MTDL 1001 | 4 | 4 | 4 | 4 | | | | | 4 | |
| MTDL 72 | 1 | 1 | 1 | 1 | | | | | 1 | |
| MTDL 87 | 2 | | | | | | | | | 2 |
| MTDL 211 | 2 | | | | | | | | | 2 |
| MTDL 221 | 2 | | | | | | | | | 2 |
| MTDL 83 | 1 | | | | | | | | | 1 |
| MTDL 982 | 2 | | | | | | | | | 2 |
| MTDL 993 | 1 | | | | | | | | | 1 |
| MTDL 941 | 1 | | | | | | | | | 1 |
| MTDL 998 | 4 | | | | | | | | | 4 |
| MTDL 954 | 4 | | | | | | | | | M |
| MTDL 226 | 2 | | | | | | | | | 4 |

83
84

Figure 8:
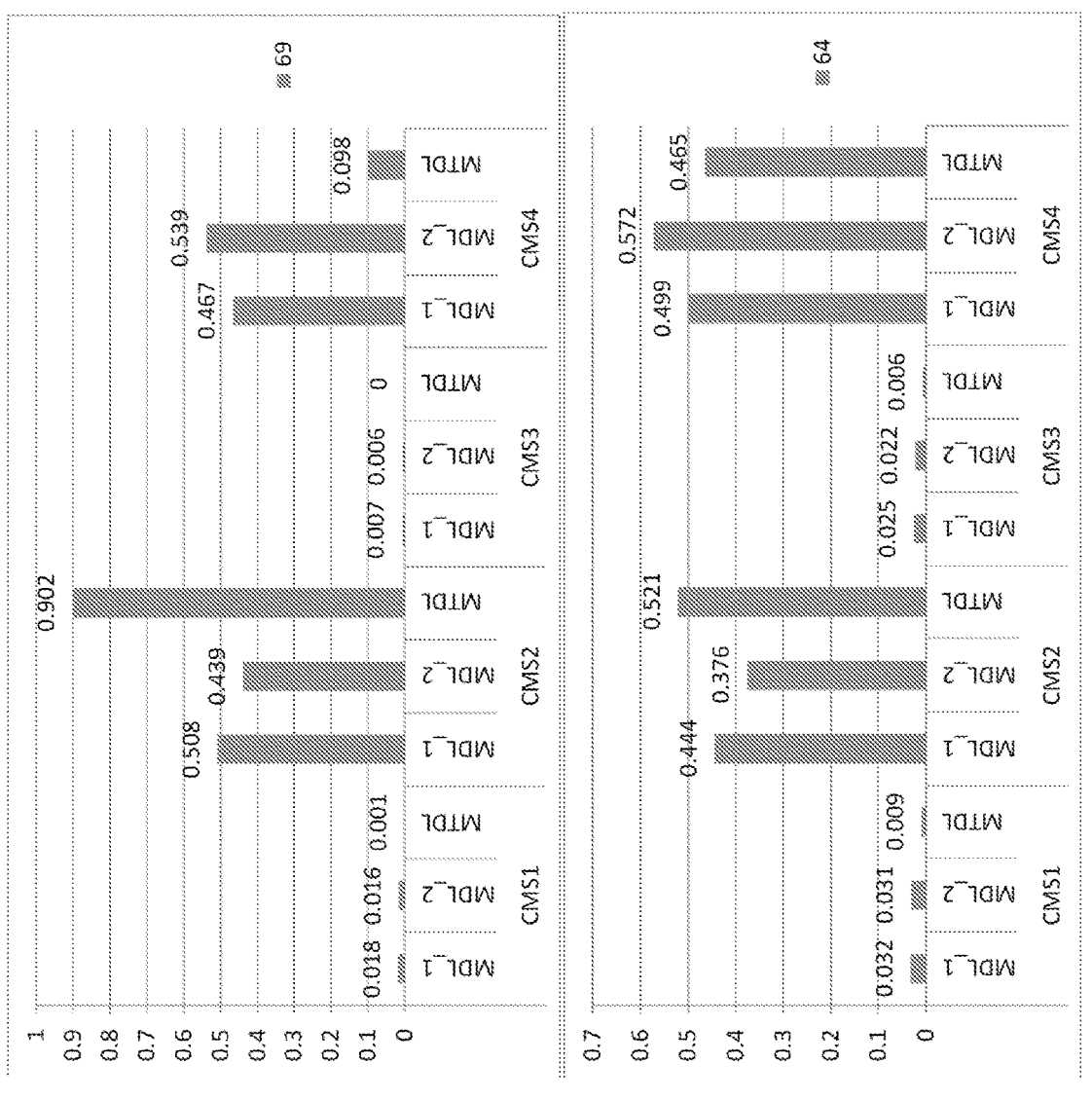
FIG. 8. Performance of CRC CMS-200 in CLIA-certified Molecular Diagnostic Laboratory. The reproducibility of the assay was determined by review of CMS calls for 24 samples that were run across 11 runs generating 120 separate reactions. One hundred and thirteen of 120 (94%) had expected results and correct CMS call. The average standard deviation of the gene expression score across all CMS was ±0.012. The average standard deviation across CMS1 was ±0.004, CMS 2 was ±0.022, CMS 3 was ±0.001 and CMS 4 was ±0.023.
Figure 9:
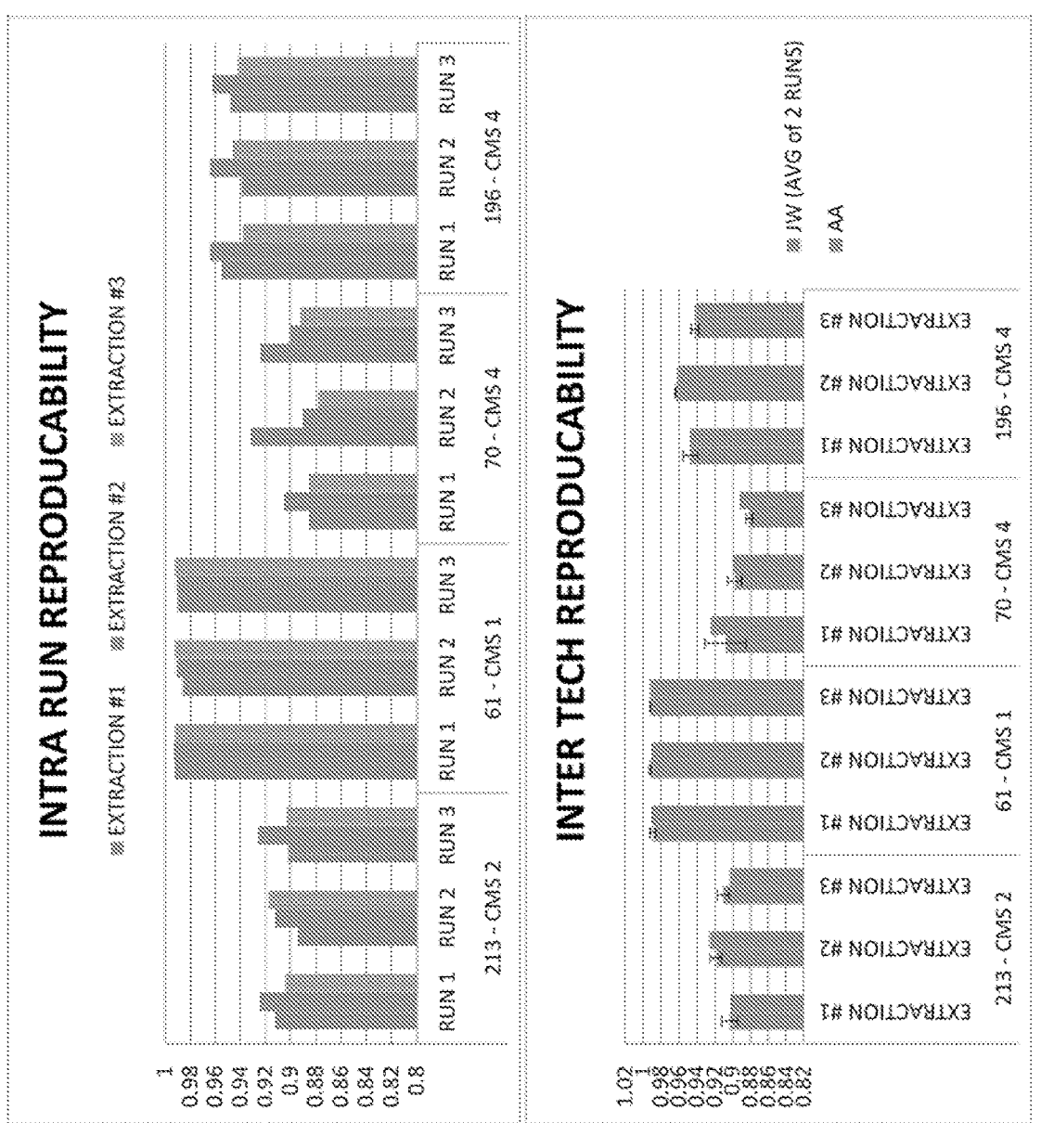
FIG. 9. Inter run reproducibility and inter tech reproducibility.

Performance of CRC CMS-200 in CLIA-certified Molecular Diagnostic Laboratory: Thirty-two out of 35 samples were accurately assigned the CMS subtype from the initial results as compared to the gold standard results (CRCSC subtype). The 3 discordant cases were not included in the overall accuracy as all had probability for a CMS subtype was in borderline range (>0.43<0.57). These samples were considered to have "mixed consensus" molecular subtypes and were reported as such. The reproducibility of the assay was determined by review of CMS calls for 24 samples that were run across 11 runs generating 120 separate reactions. One hundred and thirteen of 120 (94%) had expected results and correct CMS call. The average standard deviation of the gene expression score across all CMS was ±0.012. The average standard deviation across CMS1 was ±0.004, CMS 2 was ±0.022, CMS 3 was ±0.001 and CMS 4 was ±0.023. Seven replicates from 2 unique samples varied from expected results. The reruns of 2 misclassified samples demonstrated nearly equally higher probability of CMS2 and CMS4, indicating more of mixed subtype (FIG. 8). Inter run reproducibility was assessed from 3 separate extractions from 4 unique patient samples for a total of 12 cases. These 12 cases were run across 3 separate NanoString Runs and by 2 technologists. There was 100% concordance for the CMS classification among all 3 runs with an average standard deviation of ±0.002 for the gene expression score. The inter tech reproducibility was 100% for the CMS classification between both technicians with an average standard deviation of ±0.002 for the CMS subtype probability. Intra run reproducibility was assessed among 4 samples run in triplicate on a single Nanostring run. There was 100% concordance for the CMS classification among all 3 runs with an average standard deviation of ±0.012 for the CMS subtype probability (FIG. 9).

Figure 10:
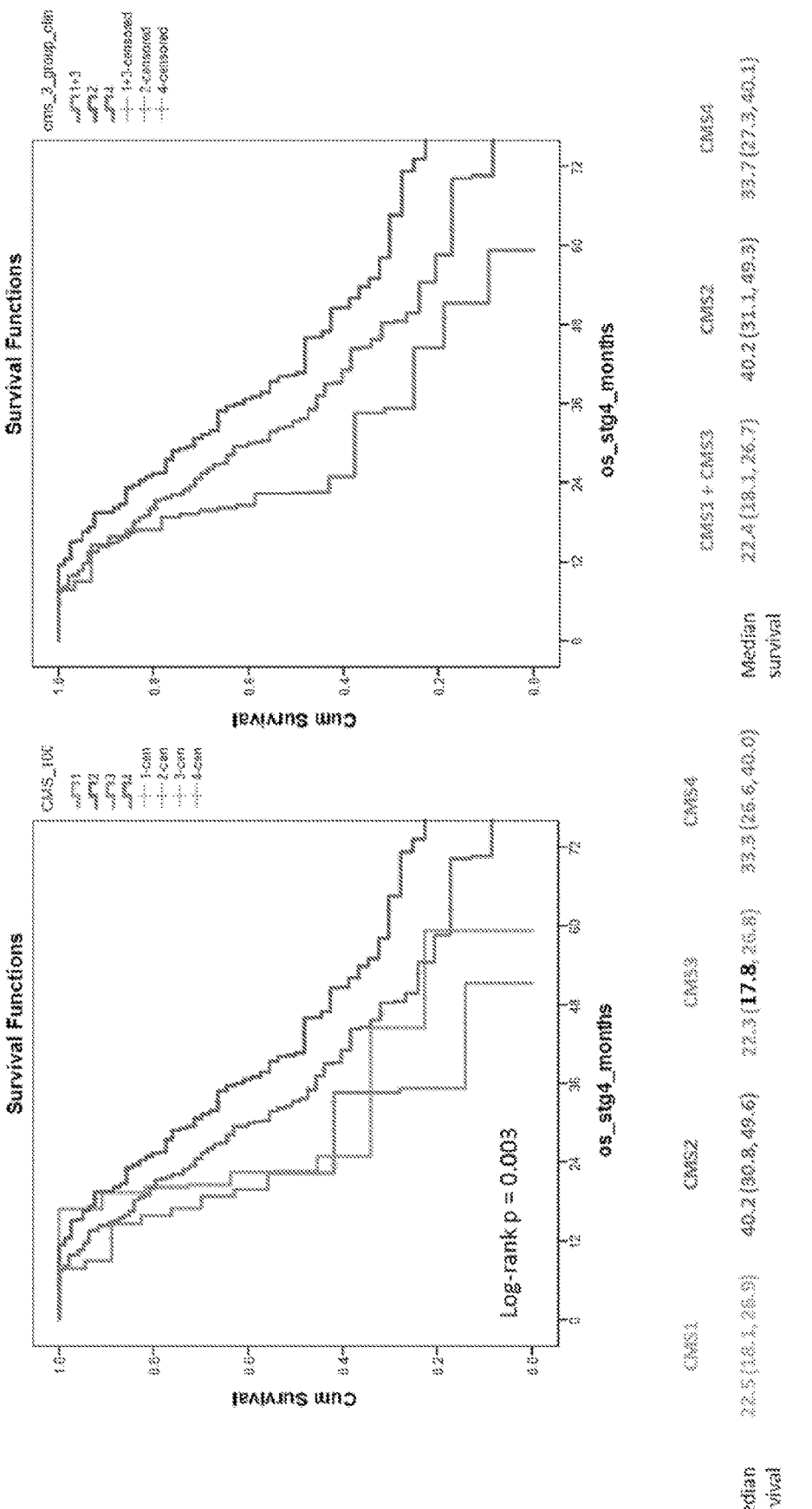
FIG. 10. CMS subtype and overall survival in stage IV colorectal cancer.

Prognostic Relevance of CMS by the Nanostring CMS Classifier: Table 16 shows clinicopathologic features and frequency of CMSs in patient enrolled in the phase II clinical trial or the ATTACC protocol. Using the Nanostring gene classifier, significant differences in overall survival were able to be identified by CMS. Specifically, patients with a CMS2 tumor had the best survival with a median of 40.2 months from stage IV diagnosis (95% CI: 30.8, 49.6), patients with a CMS1 or CMS3 tumor had the poorest survival after a stage IV diagnosis with median survival times of 22.5 (95% CI: 18.1, 26.9) or 22.3 (95% CI: 17.8, 26.8) months, respectively. Patients with a CMS4 tumor had a survival pattern that was in between that of CMS2 and CMS1 or CMS3 with a median survival time of 33.3 months (95% CI: 26.6, 40.0) (FIG. 10).

TABLE 16

| Patient Characteristics of the cohorts utilized to correlate CMS subtype and overall survival (N = 247) | |
| --- | --- |
| Mean Age at Initial Diagnosis (SD) | 51.0 (11.2) |
| Mean Age at Stage IV Diagnosis (SD) | 51.5 (11.3) |
| Sex | |
| Male | 131 (53.0) |
| Female | 116 (47.0) |
| Race/Ethnicity | |
| NH White | 182 (73.7) |
| NH African American | 20 (8.1) |
| Hispanic | 19 (7.7) |
| NH Asian | 18 (7.3) |
| Other/Unknown | 8 (3.2) |

TABLE 16-continued

| Patient Characteristics of the cohorts utilized to correlate CMS subtype and overall survival (N = 247) | |
| --- | --- |
| Stage at Initial Diagnosis | |
| I | 3 (1.2) |
| II | 17 (6.9) |
| III | 68 (27.5) |
| IV | 155 (62.8) |
| Missing | 4 (1.6) |
| Consensus Molecular Subtype | |
| 1, Immune | 10 (4.1) |
| 2, Canonical | 82 (33.2) |
| 3, Metabolic | 18 (7.3) |
| 4, Mesenchymal | 98 (39.7) |
| Mixed | 39 (15.8) |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Akhter et al., Differential expression of Toll-like receptor (TLR) and B cell receptor (BCR) signaling molecules in primary diffuse large B-cell lymphoma of the central nervous system, *J. Neurooncol.*, 121(2):289-296, 2015.

Allegra et al., Bevacizumab in stage II-III colon cancer: 5-year update of the National Surgical Adjuvant Breast and Bowel Project C-08 trial, *J. Clin. Oncol.*, 31(3):359-364, 2013.

Al-Mulla. Microarray-based CGH and copy number analysis of FFPE samples, *Methods Mol. Biol.*, 724:131-145, 2011.

Barr et al., Bypassing cellular EGF receptor dependence through epithelial-to-mesenchymal-like transitions, *Clin. Exp. Metastasis*, 25(6):685-93, 2008.

Budinska et al., Gene expression patterns unveil a new level of molecular heterogeneity in colorectal cancer, *J. Pathol.*, 231(1):63-76, 2013.

Cantor, Sample size calculations for Cohen's Kappa, Psychological Methods, 1:150-153, 1996.

Chen et al., Prognostic Fifteen-Gene Signature for Early Stage Pancreatic Ductal Adenocarcinoma, *PLoS One*, 10(8):e0133562, 2015.

D'Angelica et al., Staging laparoscopy for potentially resectable noncolorectal, nonneuroendocrine liver metastases, *Ann. Surg. Oncol.*, 9(2):204-209, 2002.

De Sousa et al., Poor-prognosis colon cancer is defined by a molecularly distinct subtype and develops from serrated precursor lesions, *Nat. Med.*, 19(5):614-618, 2013.

Dienstmann et al., Consensus molecular subtypes and the evolution of precision medicine in colorectal cancer, *Nat. Rev. Cancer*, 17(2):79-92, 2017.

Dietel et al., Predictive molecular path 1 ology and its role in targeted cancer therapy: a review focussing on clinical relevance, *Cancer Gene Ther.*, 20(4):211-221, 2013.

Forreryd et al., Evaluation of high throughput gene expression platforms using a genomic biomarker signature for prediction of skin sensitization, *BMC Genomics*, 15:379, 2014.

Gautier et al. 2004 Bioinformatics 307-315.

Goel, Evolving role of gene expression signatures as biomarkers in early-stage colon cancer, *J. Gastrointest. Cancer*, 45(4):399-404, 2014.

Goldstein, Partition resampling and extrapolation averaging: approximation methods for quantifying gene expression in large numbers of short oligonucleotide arrays, *Bioinformatics*, 22(19):2364-2372, 2006.

Guinney et al., The consensus molecular subtypes of colorectal cancer, *Nat. Med.*, 21(11):1350-1356, 2015.

Jacobs, Data analysis considerations for detecting copy number changes in formalin-fixed, paraffin-embedded tissues, Cold Spring Harb. *Protoc.*, 2012(11): 1203-1209, 2012a.

Jacobs, Sample processing considerations for detecting copy number changes in formalin-fixed, paraffin-embedded tissues, Cold Spring Harb. *Protoc.*, 2012(11):1195-1202, 2012b.

Johnson, Li and Rabinovic Biostatistics 2007 118-12.

Kauffman, Gentleman and Huber, 2009 Bioinformatics 415-416.

Kelley & Venook, Prognostic and predictive markers in stage II colon cancer: is there a role for gene expression profiling?, *Clin. Colorectal Cancer*, 10(2):73-80, 2011.

Kennedy et al., Development and independent validation of a prognostic assay for stage II colon cancer using formalin-fixed paraffin-embedded tissue, *J. Clin. Oncol.*, 29(35):4620-4626, 2011.

Kurniali et al., Management of locally advanced and metastatic colon cancer in elderly patients. *World J. Gastroenterol.*, 20(8):1910-22, 2014.

Lenz et al. 2017 Abstract 3511, Impact of consensus molecular subtyping (CMS) on overall survival (OS) and progression free survival (PFS) in patients (pts) with metastatic colorectal cancer (mCRC): Analysis of CALGB/SWOG 80405 (Alliance), ASCO 2017.

Li and Dewey BMC Bioinformatics 2011 312-323.

Ligibel et al., Body Mass Index, PAM50 Subtype, and Outcomes in Node-Positive Breast Cancer: CALGB 9741 (Alliance), *J. Natl. Cancer Inst.*, 107(9), 2015.

Maes et al., Analysis of the formalin-fixed paraffin-embedded tissue proteome: pitfalls, challenges, and future prospectives, *Amino Acids*, 45(2):205-218, 2013.

Marisa et al., 2017 Abstract 3509 ASCO 2017.

Marisa et al., Gene expression classification of colon cancer into molecular subtypes: characterization, validation, and prognostic value, *PLoS Med.*, 10(5):e1001453, 2013.

McCall, Bolstad, and Irizarry 2010 Biostatistics 242-253.

Meng et al., Comparison of microRNA deep sequencing of matched formalin-fixed paraffin-embedded and fresh frozen cancer tissues, *PLoS One*, 8(5):e64393, 2013.

Missiaglia et al., Distal and proximal colon cancers differ in terms of molecular, pathological, and clinical features, *Ann. Oncol.*, 25(10):1995-2001, 2014.

Mittempergher et al., Gene expression profiles from formalin fixed paraffin embedded breast cancer tissue are largely comparable to fresh frozen matched tissue, *PLoS One*, 6(2):e17163, 2011.

Naoi et al., Comparison of efficacy of 95-gene and 21-gene classifier (Oncotype DX) for prediction of recurrence in ER-positive and node-negative breast cancer patients, *Breast Cancer Res. Treat.*, 140(2):299-306, 2013.

Nguyen et al., Quantitative assessment of the use of modified nucleoside triphosphates in expression profiling: differential effects on signal intensities and impacts on expression ratios, *BMC Biotechnol.*, 2:14, 2002.

Pinto et al., Comprehensive assessment of array-based platforms and calling algorithms for detection of copy number variants, *Nat. Biotechnol.*, 29(6):512-520, 2011.

Potluri et al., Genomic DNA extraction methods using formalin-fixed paraffin-embedded tissue, *Anal. Biochem.*, 486:17-23, 2015.

Prat et al., Prediction of Response to Neoadjuvant Chemotherapy Using Core Needle Biopsy Samples with the Prosigna Assay, *Clin. Cancer Res.*, 22(3):560-566, 2016.

Renfro et al., ACCENT-based web calculators to predict recurrence and overall survival in stage III colon cancer, *J. Natl. Cancer Inst.*, 106(12), 2014.

Roepman et al., Colorectal cancer intrinsic subtypes predict chemotherapy benefit, deficient mismatch repair and epithelial-to-mesenchymal transition, *Int. J. Cancer*, 134(3): 552-562, 2014.

Sadanandam et al., A colorectal cancer classification system that associates cellular phenotype and responses to therapy, *Nat. Med.*, 19(5):619-625, 2013.

Schlicker et al., Subtypes of primary colorectal tumors correlate with response to targeted treatment in colorectal cell lines, *BMC Med. Genomics*, 5:66, 2012.

Sriram et al., Genomic medicine in non-small cell lung cancer: paving the path to personalized care, *Respirology*, 16(2):257-263, 2011.

Stintzing et al. 2017 Abstract 3510 ASCO 2017.

Sveen et al., Colorectal cancer consensus molecular subtypes translated to preclinical models uncover potentially targetable cancer cell dependencies, *Clin. Cancer Res.*, 24:794-806, 2017.

Taieb et al., Oxaliplatin, fluorouracil, and leucovorin with or without cetuximab in patients with resected stage III colon cancer (PETACC-8): an open-label, randomised phase 3 trial, *Lancet Oncol.*, 15 (8): 862-73, 2014.

Tian et al., A robust genomic signature for the detection of colorectal cancer patients with microsatellite instability phenotype and high mutation frequency, *J. Pathol.*, 228(4):586-595, 2012.

Veldman-Jones et al., Reproducible, Quantitative, and Flexible Molecular Subtyping of Clinical DLBCL Samples Using the NanoString nCounter System, *Clin. Cancer Res.*, 21(10):2367-78, 2015a.

Veldman-Jones et al., Evaluating Robustness and Sensitivity of the NanoString Technologies nCounter Platform to Enable Multiplexed Gene Expression Analysis of Clinical Samples, *Cancer Res.*, 75(13):2587-2593, 2015b.

Wallden et al., Development and verification of the PAM50-based Prosigna breast cancer gene signature assay, *BMC Med. Genomics*, 8:54, 2015.

Wood et al., Using next-generation sequencing for high resolution multiplex analysis of copy number variation from nanogram quantities of DNA from formalin-fixed paraffin-embedded specimens, *Nucleic Acids Res.*, 38(14):e151, 2010.

Wright et al., A gene expression-based method to diagnose clinically distinct subgroups of diffuse large B cell lymphoma, *Proc. Natl. Acad. Sci. USA*, 100(17):9991-9996, 2003.

Wu et al., Probability estimates for multi-class classification by pairwise coupling, *J. Machine Learning Res.*, 5:975-1005, 2004.

Xue et al., Diffuse large B-cell lymphoma: sub-classification by massive parallel quantitative RT-PCR, *Lab. Invest.*, 95(1):113-120, 2015.

Yaffee et al., Review of systemic therapies for locally advanced and metastatic rectal cancer, *J. Gastrointest. Oncol.*, 6(2):185-200, 2015.

What is claimed is:

1. A method of treating a patient having colorectal cancer, the method comprising:

(i) classifying a cancer status of a subject having colorectal cancer by:

(a) obtaining a tumor sample from the subject;

(b) measuring expression levels of a plurality of genes in the tumor sample, wherein the plurality of genes comprises at least 20 genes selected from the group consisting of ACSL5, ADGRG6, AGR2, ANKRD27, ANP32B, APOL1, ARHGAP10, ARHGAP32, ARID3A, ASF1B, ASPH, ASRGL1, ATP10B, ATP9A, BCL2L15, BCL6, BST2, C20orf196, C3orf14, CA8, CAB39L, CACNAID, CCDC109B, CCNO, CDC42EP2, CDC42EP5, CDCA2, CDCA7, CDHR1, CEBPA, CENPE, CEP192, CKAP2, CPNE1, CREB3L1, CRYM, CSGALNACT2, CYTH3, DACT1, DAPK2, DEPDC1, DIDO1, DOCK5, DPM1, EIF6, ENO2, EPB41L4B, ERRFI1, ESRP1, FABP5, FAM105A, FAM122B, FAM3D, FAM84A, FARP1, FBXO34, FITM2, FOXA2, FRZB, FUT8, GALNT5, GALNT8, GFPT1, GGH, GNG4, GPCPD1, GPR143, GPR153, GRM8, GTF2A2, GUCY2C, GYG2, HEPH, HES2, HLA-E, HLX, HOXD11, HSPA4L, HSPA6, HUNK, IFIT3, ILDR1, IMMP2L, JADE3, KCNK1, KCTD1, KIF2C, KLK1, LDLRAD3, LEFTY1, LM04, LNX21, LRRC16A, MAGED1, MAP2K6, MAPRE1, MLLT3, MLPH, MPP1, MRAP2, MT2A, MYRIP, NCAPH, NDFIP2, NEDD9, NOL4L, NR112, NUCB2, OSTM1, PAK6, PALB2, PALLD, PBX1, PCMTD2, PCP4, PDP1, PDZD2, PDZKIIP1, PIGR, PIGU, PITX2, PLCB1, PLCH1, PNP, POLD3, POP1, PPPIR14C, PPP1R14D, PPP1R3D, PPP3CA, PRAP1, PRC1, PRDX5, PRLR, PRR15, RAPIGAP, RARRES3, RBMS1, RETNLB, RNF183, RNF43, SAMD5, SEMASA, SERPINB1, SESN1, SHROOM4, SLC25A37, SLC30A2, SLC4A11, SLC9A2, SLCO1B3, SLCO2B1, SOCS6, SPIRE2, SRPK1, ST6GALNAC1, STAT2, TC2N, TFAP2A, TMEM61, TMEM64, TNFRSF11A, TNNC2, TNS4, TOMM34, TRIM7,

US 12,626,784 B2

149

TRNP1, TSPAN6, UGT8, UPF3A, USP14, UTP15, WFDC2, XBP1, ZCCHC24, ZDHHC23, ZG16B, ZNF415, ZSCAN18, and ZWINT;

(c) generating an expression profile based on a comparison between the expression level of the plurality of genes in the sample from the subject and a corresponding expression level obtained from a reference sample derived from a different subject having a known cancer status; and (d) categorizing the cancer status of the subject based on the expression profile; and (ii) administering an anti-cancer therapy to the subject based on the cancer status.

2. The method of claim 1, wherein step (c) comprises applying a weighted support vector machine to the expression level of the plurality of genes.

3. The method of claim 1, wherein the plurality of genes comprises at least 75 genes selected from Table 1.

4. The method of claim 1, wherein the plurality of genes comprises at least 80, 85, 90, 95, 100, 105, 110, 115, 120, 125, 130, 135, 140, 145, 150, 155, 160, 165, 170, 175, 180, 185, 190, or 195 genes selected from Table 1.

5. The method of claim 1, wherein the plurality of genes comprises all 200 genes selected from Table 1.

6. The method of claim 1, wherein the plurality of genes comprises the 75-gene classifier from Table 1.

7. The method of claim 1, wherein the plurality of genes comprises the 100-gene classifier from Table 1.

8. The method of claim 1, wherein the cancer status is categorized as consensus molecular subtype 1 (CMS1), consensus molecular subtype 2 (CMS2), consensus molecular subtype 3 (CMS3), or consensus molecular subtype 4 (CMS4).

9. The method of claim 1, wherein expression level of the plurality of genes is measured by detecting a level of mRNA transcribed from the plurality of genes.

10. The method of claim 1, wherein the expression level of the plurality of genes is measured by detecting a level of polypeptide encoded by the plurality of genes.

11. The method of claim 1, wherein the sample is a formalin-fixed, paraffin-embedded sample.

12. The method of claim 1, wherein the sample is a fresh frozen sample.

13. The method of claim 1, wherein the anti-cancer therapy is a chemotherapy, a radiation therapy, a hormonal therapy, a targeted therapy, an immunotherapy or a surgical therapy.

14. The method of claim 1, wherein if the subject is determined to have a CMS1 cancer, then administering HSP90 inhibitors, bevacizumab, atorvastatin, 2-methoxyestradiol, indibulin, tipifarnib, or disulfiram.

15. The method of claim 1, wherein if the subject is determined to have a CMS2 cancer, then administering cetuximab, an EGFR inhibitor, or a HER2 inhibitor.

16. The method of claim 1, wherein if the subject is determined to have a CMS3 cancer, then administering cetuximab, an EGFR inhibitor, or a HER2 inhibitor.

17. The method of claim 1, wherein if the subject is determined to have a CMS4 cancer, then administering HSP90 inhibitors, bevacizumab, atorvastatin, 2-methoxyestradiol, indibulin, tipifarnib, or disulfiram.

* * * * *